United States Patent
Rosen et al.

(10) Patent No.: US 12,377,622 B2
(45) Date of Patent: Aug. 5, 2025

(54) SYSTEMS AND METHODS FOR VERGENCE MATCHING WITH AN OPTICAL PROFILE AND USING REFRACTIVE INDEX WRITING

(71) Applicant: AMO Groningen B.V., Groningen (NL)

(72) Inventors: Robert Rosen, Groningen (NL); Franck Emmanuel Gounou, Groningen (NL); Carmen Canovas Vidal, Groningen (NL); Aixa Alarcon Heredia, Groningen (NL)

(73) Assignee: AMO Groningen B.V. (NL)

( * ) Notice: Subject to any disclaimer, the term of this patent is extended or adjusted under 35 U.S.C. 154(b) by 296 days.

(21) Appl. No.: 16/837,972

(22) Filed: Apr. 1, 2020

(65) Prior Publication Data

US 2020/0315783 A1  Oct. 8, 2020

Related U.S. Application Data

(60) Provisional application No. 62/830,328, filed on Apr. 5, 2019.

(51) Int. Cl.
| | | |
|---|---|---|
| *A61F 9/008* | (2006.01) | |
| *A61F 2/16* | (2006.01) | |
| *B29D 11/00* | (2006.01) | |
| *A61F 2/48* | (2006.01) | |

(52) U.S. Cl.
CPC ...... *B29D 11/00461* (2013.01); *A61F 2/1627* (2013.01); *A61F 9/00834* (2013.01); *A61F 2/16* (2013.01); *A61F 2/482* (2021.08)

(58) Field of Classification Search
CPC .......... A61F 2/1627; A61F 2/482; A61F 2/16; A61F 9/00834; A61F 2/1632; B29D 11/00461

See application file for complete search history.

(56) References Cited

U.S. PATENT DOCUMENTS

| | | |
|---|---|---|
| 2,250,597 A | 7/1941 | Moulton |
| 3,542,535 A | 11/1970 | Hensler et al. |
| 3,610,924 A | 10/1971 | Sinai |
| 4,039,827 A | 8/1977 | Zdrok et al. |
| 4,061,486 A | 12/1977 | Jahn |
| 4,073,579 A | 2/1978 | Deeg et al. |
| 4,300,818 A | 11/1981 | Schachar |
| 4,477,158 A | 10/1984 | Pollock et al. |
| 4,540,672 A | 9/1985 | Boudot et al. |

(Continued)

FOREIGN PATENT DOCUMENTS

| | | |
|---|---|---|
| AU | 711538 B2 | 10/1999 |
| AU | 712186 B2 | 10/1999 |

(Continued)

OTHER PUBLICATIONS

Thurman S.T., "Method of Obtaining Wavefront Slope Data From Through-focus Point Spread Function Measurements," Journal of the Optical Society of America, Jan. 2011, vol. 28(1), pp. 1-7.

(Continued)

*Primary Examiner* — Jacqueline Woznicki

(57) ABSTRACT

Systems and methods for improving vision of a subject implanted with an intraocular lens (IOL). In some embodiments, a method includes vergence matching for an intraocular lens (IOL) having an optical profile induced by refractive index writing.

7 Claims, 28 Drawing Sheets

(56) References Cited

U.S. PATENT DOCUMENTS

| | | |
|---|---|---|
| 4,611,892 A | 9/1986 | Kawashima et al. |
| 4,650,845 A | 3/1987 | Hegel |
| 4,691,715 A | 9/1987 | Tanne |
| 4,720,286 A | 1/1988 | Bailey et al. |
| 4,856,889 A | 8/1989 | Guilino et al. |
| 4,985,472 A | 1/1991 | Aosai et al. |
| 5,015,523 A | 5/1991 | Kawashima et al. |
| 5,066,301 A | 11/1991 | Wiley |
| 5,074,942 A | 12/1991 | Kearns et al. |
| 5,116,111 A | 5/1992 | Simpson et al. |
| 5,172,143 A | 12/1992 | Baude et al. |
| 5,196,026 A | 3/1993 | Barrett et al. |
| 5,229,797 A | 7/1993 | Futhey et al. |
| 5,233,007 A | 8/1993 | Yang |
| 5,296,305 A | 3/1994 | Baude et al. |
| 5,319,007 A | 6/1994 | Bright |
| 5,357,024 A | 10/1994 | Leclaire |
| 5,424,339 A | 6/1995 | Zanka et al. |
| 5,460,627 A | 10/1995 | O'Donnell, Jr. |
| 5,476,515 A | 12/1995 | Kelman et al. |
| 5,521,656 A | 5/1996 | Portney |
| 5,541,278 A | 7/1996 | Raleigh et al. |
| 5,648,402 A | 7/1997 | Nunez et al. |
| 5,694,195 A | 12/1997 | Engardio et al. |
| 5,728,156 A | 3/1998 | Gupta et al. |
| 5,762,836 A | 6/1998 | Bos et al. |
| 5,830,578 A | 11/1998 | Ono et al. |
| 5,873,931 A | 2/1999 | Scholz et al. |
| 5,891,931 A | 4/1999 | Leboeuf et al. |
| 5,908,876 A | 6/1999 | Fujii et al. |
| 5,910,537 A | 6/1999 | Feingold et al. |
| 5,928,663 A | 7/1999 | Peyman |
| 5,973,192 A | 10/1999 | Woodbury et al. |
| 6,075,652 A | 6/2000 | Ono et al. |
| 6,086,204 A | 7/2000 | Magnante |
| 6,099,123 A | 8/2000 | Engardio et al. |
| 6,139,146 A | 10/2000 | Zhang |
| 6,248,285 B1 | 6/2001 | Henry et al. |
| 6,256,152 B1 | 7/2001 | Coldrey et al. |
| 6,270,698 B1 | 8/2001 | Pope |
| 6,300,464 B2 | 10/2001 | Morijiri et al. |
| 6,313,187 B2 | 11/2001 | Leboeuf et al. |
| 6,313,316 B1 | 11/2001 | Kitahara et al. |
| 6,339,505 B1 | 1/2002 | Bates |
| 6,450,642 B1 | 9/2002 | Jethmalani et al. |
| 6,454,408 B1 | 9/2002 | Morris et al. |
| 6,464,484 B1 | 10/2002 | Powers et al. |
| 6,478,792 B1 | 11/2002 | Hansel |
| 6,528,005 B2 | 3/2003 | Amagai et al. |
| 6,655,946 B2 | 12/2003 | Foreman et al. |
| 6,676,398 B2 | 1/2004 | Foreman et al. |
| 6,676,399 B1 | 1/2004 | Foreman |
| 6,695,880 B1 | 2/2004 | Roffman et al. |
| 6,699,953 B2 | 3/2004 | Oshikiri et al. |
| 6,706,894 B2 | 3/2004 | Okubo et al. |
| 6,723,260 B1 | 4/2004 | Powers et al. |
| 6,746,632 B2 | 6/2004 | Houston et al. |
| 6,747,090 B2 | 6/2004 | De Groot et al. |
| 6,749,632 B2 | 6/2004 | Sandstedt et al. |
| 6,749,779 B2 | 6/2004 | Soane et al. |
| 6,758,663 B2 | 7/2004 | Foreman et al. |
| 6,770,735 B2 | 8/2004 | Tanaka et al. |
| 6,776,934 B2 | 8/2004 | Lai |
| 6,790,022 B1 | 9/2004 | Foreman |
| 6,790,024 B2 | 9/2004 | Foreman |
| 6,793,340 B1 | 9/2004 | Morris et al. |
| 6,808,381 B2 | 10/2004 | Foreman et al. |
| 6,840,619 B2 | 1/2005 | Dreher |
| 6,851,804 B2 | 2/2005 | Jethmalani et al. |
| 6,852,793 B2 | 2/2005 | Salamone et al. |
| 6,863,518 B2 | 3/2005 | Powers |
| 6,863,848 B2 | 3/2005 | Engardio et al. |
| 6,875,005 B2 | 4/2005 | Foreman |
| 6,893,245 B2 | 5/2005 | Foreman et al. |
| 6,899,831 B1 | 5/2005 | Foreman |
| 6,923,802 B2 | 8/2005 | Williams et al. |
| 6,942,924 B2 | 9/2005 | He et al. |
| 6,962,669 B2 | 11/2005 | Foreman et al. |
| 6,964,479 B2 | 11/2005 | Buazza et al. |
| 7,001,374 B2 | 2/2006 | Peyman |
| 7,004,740 B2 | 2/2006 | Foreman |
| 7,009,024 B2 | 3/2006 | Salamone et al. |
| 7,009,031 B2 | 3/2006 | Yoshimura et al. |
| 7,025,910 B2 | 4/2006 | Lattis et al. |
| 7,044,429 B1 | 5/2006 | Foreman et al. |
| 7,045,081 B2 | 5/2006 | Foreman et al. |
| 7,052,262 B2 | 5/2006 | Foreman et al. |
| 7,060,095 B2 | 6/2006 | Ho et al. |
| 7,060,208 B2 | 6/2006 | Foreman et al. |
| 7,066,597 B2 | 6/2006 | Miller et al. |
| 7,066,955 B2 | 6/2006 | Lowery |
| 7,081,272 B2 | 7/2006 | Sasaki et al. |
| 7,083,404 B2 | 8/2006 | Foreman et al. |
| 7,083,851 B2 | 8/2006 | Faris |
| 7,090,349 B2 | 8/2006 | Perrott et al. |
| 7,104,648 B2 | 9/2006 | Dahi et al. |
| 7,124,995 B2 | 10/2006 | Foreman et al. |
| 7,169,874 B2 | 1/2007 | Salamone et al. |
| 7,172,285 B1 | 2/2007 | Altmann et al. |
| 7,186,266 B2 | 3/2007 | Peyman |
| 7,207,998 B2 | 4/2007 | Feingold |
| 7,217,778 B2 | 5/2007 | Verbruggen et al. |
| 7,234,810 B2 | 6/2007 | Warden et al. |
| 7,239,451 B2 | 7/2007 | Suzuki et al. |
| 7,279,538 B2 | 10/2007 | Lai et al. |
| 7,293,871 B2 | 11/2007 | Dreher et al. |
| 7,297,160 B2 | 11/2007 | Salamone et al. |
| 7,301,705 B2 | 11/2007 | Yoshimura et al. |
| 7,341,345 B2 | 3/2008 | Azar et al. |
| 7,393,101 B2 | 7/2008 | Blum et al. |
| 7,399,524 B2 | 7/2008 | Suzuki et al. |
| 7,423,108 B2 | 9/2008 | Kunzler et al. |
| 7,423,801 B2 | 9/2008 | Kaufman et al. |
| 7,446,157 B2 | 11/2008 | Mentak et al. |
| 7,452,074 B2 | 11/2008 | Kumar et al. |
| 7,457,507 B2 | 11/2008 | Kuramoto et al. |
| 7,499,221 B2 | 3/2009 | Nishioka |
| 7,507,358 B2 | 3/2009 | Morris et al. |
| 7,563,827 B2 | 7/2009 | Koyama et al. |
| 7,576,920 B2 | 8/2009 | Downing et al. |
| 7,598,196 B2 | 10/2009 | Friz et al. |
| 7,632,904 B2 | 12/2009 | Salamone et al. |
| 7,701,641 B2 | 4/2010 | Dreher et al. |
| 7,708,402 B2 | 5/2010 | Ribak |
| 7,714,090 B2 | 5/2010 | Iwamoto et al. |
| 7,735,998 B2 | 6/2010 | Volk |
| 7,767,779 B2 | 8/2010 | Jallouli et al. |
| 7,782,537 B2 | 8/2010 | Naito et al. |
| 7,789,910 B2 | 9/2010 | Knox et al. |
| 7,806,526 B2 | 10/2010 | Bourdoncle et al. |
| 7,808,707 B2 | 10/2010 | Cano et al. |
| 7,854,508 B2 | 12/2010 | Nakajima et al. |
| 7,857,848 B2 | 12/2010 | Mentak |
| 7,878,649 B2 | 2/2011 | Archambeau et al. |
| 7,883,540 B2 | 2/2011 | Niwa et al. |
| 7,901,787 B2 | 3/2011 | Miyakawa |
| 7,922,325 B2 | 4/2011 | Toda et al. |
| 7,926,940 B2 | 4/2011 | Blum et al. |
| 7,931,371 B2 | 4/2011 | Dai |
| 7,935,212 B2 | 5/2011 | Jiang et al. |
| 7,950,398 B2 | 5/2011 | Schroeder et al. |
| 7,959,284 B2 | 6/2011 | Lai |
| 7,959,286 B2 | 6/2011 | Plummer |
| 7,968,204 B2 | 6/2011 | Koh et al. |
| 7,992,997 B2 | 8/2011 | Varnas |
| 8,003,022 B2 | 8/2011 | Diggins et al. |
| 8,034,262 B2 | 10/2011 | Lai et al. |
| 8,043,370 B2 | 10/2011 | Bretthauer et al. |
| 8,052,278 B2 | 11/2011 | Bovet et al. |
| 8,109,999 B2 | 2/2012 | Hampp |
| 8,113,651 B2 | 2/2012 | Blum et al. |
| 8,153,248 B2 | 4/2012 | Naito |
| 8,158,712 B2 | 4/2012 | Your |
| 8,167,427 B2 | 5/2012 | Guillon et al. |

(56) References Cited

U.S. PATENT DOCUMENTS

| | | |
|---|---|---|
| 8,169,716 B2 | 5/2012 | Zalevsky et al. |
| 8,172,397 B2 | 5/2012 | Ballet et al. |
| 8,216,309 B2 | 7/2012 | Azar |
| 8,231,217 B2 | 7/2012 | Ballet et al. |
| 8,240,849 B2 | 8/2012 | Widman et al. |
| 8,262,646 B2 | 9/2012 | Frey et al. |
| 8,292,952 B2 | 10/2012 | Bille |
| 8,329,763 B2 | 12/2012 | Werner |
| 8,361,353 B2 | 1/2013 | Brait et al. |
| 8,403,483 B2 | 3/2013 | Klink et al. |
| 8,404,797 B2 | 3/2013 | Kawabe et al. |
| 8,454,862 B2 | 6/2013 | Andino et al. |
| 8,470,948 B2 | 6/2013 | Stiegman |
| 8,486,055 B2 | 7/2013 | Knox et al. |
| 8,517,534 B2 | 8/2013 | Sone et al. |
| 8,523,354 B2 | 9/2013 | Haddock et al. |
| 8,529,059 B2 | 9/2013 | Suzuki |
| 8,570,485 B2 | 10/2013 | Ye et al. |
| 8,586,664 B2 | 11/2013 | Buhler et al. |
| 8,611,010 B2 | 12/2013 | Radcliffe et al. |
| 8,636,358 B2 | 1/2014 | Binder |
| 8,681,428 B1 | 3/2014 | Brown |
| 8,715,345 B2 | 5/2014 | Deboer et al. |
| 8,759,414 B2 | 6/2014 | Muller-Lierheim et al. |
| 8,778,450 B2 | 7/2014 | Zuyi et al. |
| 8,789,943 B2 | 7/2014 | Sverdrup et al. |
| 8,789,944 B2 | 7/2014 | Nishimoto et al. |
| 8,801,177 B2 | 8/2014 | Archambeau et al. |
| 8,815,378 B2 | 8/2014 | Gueneau et al. |
| 8,815,388 B2 | 8/2014 | Yamazaki et al. |
| 8,834,757 B2 | 9/2014 | Auciello et al. |
| 8,842,370 B2 | 9/2014 | Jethmalani et al. |
| 8,846,140 B2 | 9/2014 | Roisin et al. |
| 8,895,233 B2 | 11/2014 | McLeod |
| 8,901,190 B2 | 12/2014 | Smith et al. |
| 8,902,487 B2 | 12/2014 | Ohnishi |
| 8,933,143 B2 | 1/2015 | Boydston et al. |
| 8,944,594 B2 | 2/2015 | McLeod et al. |
| 8,980,431 B2 | 3/2015 | Mori et al. |
| 9,012,566 B2 | 4/2015 | Buhler et al. |
| 9,019,614 B2 | 4/2015 | Devaul |
| 9,052,436 B2 | 6/2015 | Jang et al. |
| 9,074,040 B2 | 7/2015 | Turshani et al. |
| 9,107,746 B2 | 8/2015 | Sahler et al. |
| 9,119,710 B2 | 9/2015 | Grubbs et al. |
| 9,144,491 B2 | 9/2015 | Knox et al. |
| 9,146,407 B2 | 9/2015 | Clarke et al. |
| 9,150,694 B2 | 10/2015 | Aoki et al. |
| 9,155,614 B2 | 10/2015 | Blum et al. |
| 9,164,206 B2 | 10/2015 | Valley et al. |
| 11,529,230 B2 | 12/2022 | Rosen et al. |
| 11,564,839 B2 | 1/2023 | Rosen et al. |
| 11,583,388 B2 | 2/2023 | Rosen et al. |
| 11,583,389 B2 | 2/2023 | Rosen et al. |
| 2001/0055094 A1 | 12/2001 | Zhang |
| 2002/0016629 A1 | 2/2002 | Sandstedt et al. |
| 2002/0031676 A1 | 3/2002 | Jonza et al. |
| 2002/0093701 A1 | 7/2002 | Zhang et al. |
| 2003/0007257 A1 | 1/2003 | Bell, Jr. et al. |
| 2003/0017303 A1 | 1/2003 | Shindo et al. |
| 2003/0038920 A1 | 2/2003 | Lin |
| 2004/0117013 A1 | 6/2004 | Schachar |
| 2004/0142185 A1 | 7/2004 | Takushima |
| 2005/0090612 A1 | 4/2005 | Soane et al. |
| 2005/0231677 A1 | 10/2005 | Meredith |
| 2005/0254003 A1 | 11/2005 | Jani et al. |
| 2005/0260388 A1 | 11/2005 | Lai |
| 2006/0065989 A1 | 3/2006 | Druffel et al. |
| 2006/0135952 A1 | 6/2006 | Curatu et al. |
| 2006/0155093 A1 | 7/2006 | Kitahara |
| 2006/0177638 A1 | 8/2006 | Shibuya et al. |
| 2006/0204655 A1 | 9/2006 | Takahashi |
| 2006/0227283 A1 | 10/2006 | Ooi et al. |
| 2007/0097512 A1 | 5/2007 | Toyoda et al. |
| 2007/0193987 A1 | 8/2007 | Bischoff et al. |
| 2007/0225466 A1 | 9/2007 | Matsumoto et al. |
| 2007/0249794 A1 | 10/2007 | Evans et al. |
| 2007/0255401 A1 | 11/2007 | Lang |
| 2007/0273973 A1 | 11/2007 | Kursawe et al. |
| 2008/0012850 A1 | 1/2008 | Keating, III |
| 2008/0027537 A1 | 1/2008 | Gerlach et al. |
| 2008/0137032 A1 | 6/2008 | Lawrence et al. |
| 2008/0170487 A1 | 7/2008 | Kimura et al. |
| 2008/0200582 A1 | 8/2008 | Craciun et al. |
| 2008/0212023 A1 | 9/2008 | Bovet et al. |
| 2008/0242965 A1 | 10/2008 | Norris et al. |
| 2008/0268253 A1 | 10/2008 | Murai et al. |
| 2008/0274352 A1 | 11/2008 | Hao et al. |
| 2009/0029153 A1 | 1/2009 | Naito et al. |
| 2009/0036880 A1 | 2/2009 | Bischoff et al. |
| 2009/0066911 A1 | 3/2009 | Ishizaki et al. |
| 2009/0078154 A1 | 3/2009 | Sasaki et al. |
| 2009/0099329 A1 | 4/2009 | Ryu et al. |
| 2009/0118828 A1 | 5/2009 | Altmann |
| 2009/0169859 A1 | 7/2009 | Biteau et al. |
| 2009/0174098 A1 | 7/2009 | Rouault de Coligny et al. |
| 2009/0189303 A1 | 7/2009 | Diggins et al. |
| 2009/0228101 A1 | 9/2009 | Zadno-Azizi |
| 2009/0299345 A1 | 12/2009 | Bille et al. |
| 2009/0316110 A1 | 12/2009 | Cano et al. |
| 2010/0004741 A1 | 1/2010 | Gupta et al. |
| 2010/0082017 A1 | 4/2010 | Zickler et al. |
| 2010/0190919 A1 | 7/2010 | Kimura et al. |
| 2010/0245761 A1* | 9/2010 | Widman ............... G02B 1/043 351/159.41 |
| 2010/0324408 A1 | 12/2010 | Klink et al. |
| 2011/0071509 A1 | 3/2011 | Knox et al. |
| 2011/0144747 A1 | 6/2011 | McGinniss et al. |
| 2011/0164329 A1 | 7/2011 | Jiang et al. |
| 2011/0172649 A1 | 7/2011 | Schuele et al. |
| 2011/0190467 A1 | 8/2011 | Hughes et al. |
| 2011/0242662 A1 | 10/2011 | Momoki et al. |
| 2011/0245919 A1 | 10/2011 | Pettit |
| 2012/0059439 A1 | 3/2012 | Yoon |
| 2012/0141770 A1 | 6/2012 | Cadet et al. |
| 2012/0172483 A1 | 7/2012 | Nakamura et al. |
| 2012/0172854 A1 | 7/2012 | Raymond et al. |
| 2012/0212696 A1 | 8/2012 | Trajkovska et al. |
| 2012/0240939 A1 | 9/2012 | Kandulla |
| 2012/0259411 A1 | 10/2012 | Hong et al. |
| 2012/0296423 A1 | 11/2012 | Caffey et al. |
| 2012/0310223 A1 | 12/2012 | Knox et al. |
| 2012/0310340 A1 | 12/2012 | Knox et al. |
| 2013/0035760 A1 | 2/2013 | Portney |
| 2013/0218270 A1 | 8/2013 | Blanckaert et al. |
| 2013/0222756 A1 | 8/2013 | Van Heugten |
| 2013/0222913 A1 | 8/2013 | Tomoda et al. |
| 2013/0231740 A1 | 9/2013 | Mentak |
| 2013/0253159 A1 | 9/2013 | Benz et al. |
| 2013/0273317 A1 | 10/2013 | Nakayama |
| 2013/0289153 A1 | 10/2013 | Sandstedt et al. |
| 2013/0308186 A1 | 11/2013 | Cathey, Jr. et al. |
| 2013/0309453 A1 | 11/2013 | Biver et al. |
| 2013/0337161 A1 | 12/2013 | Akimoto et al. |
| 2014/0043584 A1 | 2/2014 | Blum |
| 2014/0135920 A1 | 5/2014 | Sahler et al. |
| 2014/0148899 A1 | 5/2014 | Fehr et al. |
| 2014/0171612 A1 | 6/2014 | Bojkova et al. |
| 2014/0192420 A1 | 7/2014 | Baer et al. |
| 2014/0198296 A1 | 7/2014 | Kadowaki |
| 2014/0241605 A1* | 8/2014 | Izatt ............... G06T 15/00 382/131 |
| 2014/0276674 A1 | 9/2014 | Lee et al. |
| 2014/0276680 A1 | 9/2014 | Dennison et al. |
| 2014/0300857 A1 | 10/2014 | Cohen-Tannoudji et al. |
| 2014/0316521 A1 | 10/2014 | McLeod et al. |
| 2014/0327875 A1 | 11/2014 | Blum et al. |
| 2014/0327884 A1 | 11/2014 | Bühren et al. |
| 2014/0342016 A1 | 11/2014 | Raymond et al. |
| 2014/0343541 A1 | 11/2014 | Scott et al. |
| 2014/0347625 A1 | 11/2014 | Tomoda et al. |
| 2015/0081016 A1 | 3/2015 | De Sio et al. |
| 2015/0103313 A1 | 4/2015 | Sarver et al. |

(56) References Cited

U.S. PATENT DOCUMENTS

| | | | |
|---|---|---|---|
| 2015/0126979 A1* | 5/2015 | Knox | C08J 7/12 606/4 |
| 2015/0166704 A1 | 6/2015 | Otani et al. | |
| 2015/0203635 A1 | 7/2015 | Tapsak | |
| 2015/0203710 A1 | 7/2015 | Feuillade et al. | |
| 2015/0234206 A1 | 8/2015 | Lee et al. | |
| 2015/0241714 A1 | 8/2015 | Allione et al. | |
| 2015/0258240 A1 | 9/2015 | Grubbs | |
| 2015/0277150 A1 | 10/2015 | Granger et al. | |
| 2015/0321991 A1 | 11/2015 | Ponrathnam et al. | |
| 2015/0351630 A1 | 12/2015 | Engelhardt et al. | |
| 2016/0074007 A1 | 3/2016 | Fedor | |
| 2016/0089271 A1 | 3/2016 | Zacharias | |
| 2016/0150952 A1 | 6/2016 | Raymond et al. | |
| 2016/0296662 A1* | 10/2016 | Stoy | A61F 2/1627 |
| 2017/0027437 A1 | 2/2017 | Neal et al. | |
| 2017/0156931 A1 | 6/2017 | Knox et al. | |
| 2018/0021172 A1 | 1/2018 | Zheleznyak et al. | |
| 2018/0110613 A1 | 4/2018 | Wortz et al. | |
| 2018/0200112 A1 | 7/2018 | Krampert et al. | |
| 2018/0243082 A1* | 8/2018 | Zheleznyak | A61F 2/1613 |
| 2018/0368972 A1 | 12/2018 | Rosen et al. | |
| 2018/0373060 A1 | 12/2018 | Knox et al. | |
| 2019/0000433 A1 | 1/2019 | Argenta et al. | |
| 2019/0004221 A1 | 1/2019 | Weeber et al. | |
| 2019/0004335 A1 | 1/2019 | Weeber et al. | |
| 2019/0021904 A1 | 1/2019 | Schuele et al. | |
| 2019/0060056 A1 | 2/2019 | Serdarevic et al. | |
| 2019/0142576 A1 | 5/2019 | Goldshleger et al. | |
| 2019/0239803 A1 | 8/2019 | Rosen et al. | |
| 2020/0197157 A1 | 6/2020 | Shmukler et al. | |
| 2020/0315782 A1 | 10/2020 | Rosen et al. | |
| 2020/0315848 A1 | 10/2020 | Rosen et al. | |
| 2020/0315849 A1 | 10/2020 | Rosen et al. | |
| 2021/0030531 A1 | 2/2021 | Ambati | |
| 2022/0031504 A1 | 2/2022 | Schuele et al. | |
| 2023/0123960 A1 | 4/2023 | Rosen et al. | |
| 2023/0200975 A1 | 6/2023 | Rosen et al. | |
| 2023/0210654 A1 | 7/2023 | Rosen et al. | |

FOREIGN PATENT DOCUMENTS

| | | |
|---|---|---|
| AU | 734097 B2 | 6/2001 |
| AU | 774079 B2 | 6/2004 |
| AU | 2003281672 B2 | 11/2007 |
| AU | 2008201900 A1 | 5/2008 |
| AU | 2006305319 B2 | 2/2012 |
| AU | 2013228002 A1 | 10/2013 |
| AU | 2014200799 A1 | 4/2014 |
| AU | 2009278956 B2 | 4/2015 |
| CA | 2050515 A1 | 3/1992 |
| CA | 2059328 A1 | 10/1992 |
| CA | 2150478 A1 | 8/1994 |
| CA | 2291548 A1 | 12/2000 |
| CA | 2563763 A1 | 11/2005 |
| CA | 2722274 A1 | 10/2009 |
| CA | 2752046 A1 | 8/2010 |
| CA | 2802793 A1 | 2/2012 |
| CA | 2824916 A1 | 7/2012 |
| CA | 2837756 A1 | 12/2012 |
| CA | 2859978 A1 | 6/2013 |
| CA | 2858283 A1 | 7/2013 |
| CA | 2888013 A1 | 3/2014 |
| CA | 2895273 A1 | 6/2014 |
| CN | 2411767 Y | 12/2000 |
| CN | 101107277 A | 1/2008 |
| CN | 101564551 A | 10/2009 |
| CN | 202004310 U | 10/2011 |
| CN | 101321700 B | 1/2012 |
| CN | 103698901 A | 4/2014 |
| CN | 104151807 A | 11/2014 |
| DE | 102015009610 A1 | 1/2017 |
| EP | 0064812 B1 | 8/1985 |
| EP | 0269288 B1 | 2/1992 |
| EP | 0855993 B1 | 1/2001 |
| EP | 0610310 B1 | 4/2002 |
| EP | 1195623 A1 | 4/2002 |
| EP | 1003795 B1 | 2/2004 |
| EP | 1484352 A1 | 12/2004 |
| EP | 1044097 B1 | 11/2005 |
| EP | 1249716 B1 | 9/2007 |
| EP | 2067613 A1 | 6/2009 |
| EP | 2174966 A1 | 4/2010 |
| EP | 2192932 B1 | 5/2011 |
| EP | 2192934 B1 | 5/2011 |
| EP | 2711741 A1 | 3/2014 |
| EP | 2033021 B1 | 8/2015 |
| EP | 2901965 A1 | 8/2015 |
| EP | 2906970 B1 | 11/2016 |
| FR | 2655842 A1 | 6/1991 |
| FR | 2667073 A1 | 3/1992 |
| FR | 2774998 A1 | 8/1999 |
| GB | 2149804 A | 6/1985 |
| GB | 2247538 A | 3/1992 |
| GB | 2265367 A | 9/1993 |
| GB | 2427169 B | 10/2010 |
| JP | S5541416 A | 3/1980 |
| JP | S638239 A | 1/1988 |
| JP | S63204229 A | 8/1988 |
| JP | S63279201 A | 11/1988 |
| JP | H06123856 A | 5/1994 |
| JP | H06261923 A | 9/1994 |
| JP | H10273887 A | 10/1998 |
| JP | 2002156503 A | 5/2002 |
| JP | 2002182002 A | 6/2002 |
| JP | 2003222703 A | 8/2003 |
| JP | 2004184933 A | 7/2004 |
| JP | 2004309683 A | 11/2004 |
| JP | 2005133131 A | 5/2005 |
| JP | 2006189565 A | 7/2006 |
| JP | 2006267561 A | 10/2006 |
| JP | 2007046008 A | 2/2007 |
| JP | 2007091921 A | 4/2007 |
| JP | 2007163655 A | 6/2007 |
| JP | 2007260192 A | 10/2007 |
| JP | 2008096828 A | 4/2008 |
| JP | 2008158513 A | 7/2008 |
| JP | 2008239920 A | 10/2008 |
| JP | 2009175658 A | 8/2009 |
| JP | 2009227835 A | 10/2009 |
| JP | 2009227836 A | 10/2009 |
| JP | 2009234180 A | 10/2009 |
| JP | 2009256275 A | 11/2009 |
| JP | 2009256662 A | 11/2009 |
| JP | 2010105229 A | 5/2010 |
| JP | 2010202778 A | 9/2010 |
| JP | 2010204456 A | 9/2010 |
| JP | 2011038050 A | 2/2011 |
| JP | 2011084817 A | 4/2011 |
| JP | 2012082386 A | 4/2012 |
| JP | 2012141407 A | 7/2012 |
| JP | 2012234218 A | 11/2012 |
| JP | 2012247741 A | 12/2012 |
| JP | 2013010842 A | 1/2013 |
| JP | 2013234127 A | 11/2013 |
| JP | 5597780 B1 | 10/2014 |
| KR | 20020027191 A | 4/2002 |
| KR | 20080023016 A | 3/2008 |
| KR | 20140122846 A | 10/2014 |
| KR | 20150018006 A | 2/2015 |
| WO | 9519748 A1 | 7/1995 |
| WO | 9710527 A1 | 3/1997 |
| WO | 9913361 A1 | 3/1999 |
| WO | 0064956 A1 | 11/2000 |
| WO | 0105578 A1 | 1/2001 |
| WO | 0182815 A1 | 11/2001 |
| WO | 2004023189 A1 | 3/2004 |
| WO | 2004068202 A1 | 8/2004 |
| WO | 2006043409 A1 | 4/2006 |
| WO | 2007008666 A2 | 1/2007 |
| WO | 2008055118 A2 | 5/2008 |
| WO | 2008062903 A1 | 5/2008 |
| WO | 2008070851 A2 | 6/2008 |

(56) References Cited

FOREIGN PATENT DOCUMENTS

| | | |
|---|---|---|
| WO | 2009148454 A1 | 12/2009 |
| WO | 2010016242 A1 | 2/2010 |
| WO | 2010119755 A1 | 10/2010 |
| WO | 2011080472 A2 | 7/2011 |
| WO | 2011102502 A1 | 8/2011 |
| WO | 2011109039 A1 | 9/2011 |
| WO | 2011125956 A1 | 10/2011 |
| WO | 2012034265 A1 | 3/2012 |
| WO | 2012074742 A1 | 6/2012 |
| WO | 2012112014 A2 | 8/2012 |
| WO | 2012156081 A1 | 11/2012 |
| WO | 2012166696 A1 | 12/2012 |
| WO | 2013022065 A1 | 2/2013 |
| WO | 2013169987 A1 | 11/2013 |
| WO | 2014131879 A1 | 9/2014 |
| WO | 2014140905 A1 | 9/2014 |
| WO | 2014158615 A1 | 10/2014 |
| WO | 2015000534 A1 | 1/2015 |
| WO | 2015010119 A2 | 1/2015 |
| WO | 2015015205 A1 | 2/2015 |
| WO | 2015016363 A1 | 2/2015 |
| WO | 2015038611 A1 | 3/2015 |
| WO | 2015038614 A1 | 3/2015 |
| WO | 2015038620 A2 | 3/2015 |
| WO | 2015038623 A1 | 3/2015 |
| WO | 2015068839 A1 | 5/2015 |
| WO | 2015132605 A1 | 9/2015 |
| WO | 2015164779 A1 | 10/2015 |
| WO | 2015170133 A1 | 11/2015 |
| WO | 2015170278 A1 | 11/2015 |
| WO | 2016111851 A1 | 7/2016 |

OTHER PUBLICATIONS

Rosales et al., "Customized Computer Models Of Eyes With Intraocular Lenses", Optics Express, vol. 15, No. 5, pp. 2204-2218, Mar. 5, 2007.

* cited by examiner

SYSTEMS AND METHODS FOR VERGENCE MATCHING WITH AN OPTICAL PROFILE AND USING REFRACTIVE INDEX WRITING

CROSS REFERENCE TO RELATED APPLICATIONS

This application claims the benefit under 35 U.S.C. § 119(e) of U.S. Provisional Patent Application No. 62/830,328, filed Apr. 5, 2019, which is incorporated herein by reference in its entirety.

BACKGROUND

Currently a range of factors can limit visual performance of a patient (also referred to herein as a "subject") following corrective surgery (e.g., cataract surgery) in which an intraocular lens (IOL) is implanted in the patient's eye(s). These limiting factors can include: incorrect IOL power, which is commonly caused by incorrect IOL power calculations due to biometry accuracy; and uncorrected astigmatism, which can be caused by factors such as surgically induced astigmatism, effect of posterior corneal astigmatism, incorrect toric IOL power calculation, toric IOL rotation, or misplacement and use of non-toric IOLs in toric corneas. Additional limiting factors can include: spectacle dependence, which can be due to monofocal IOL implantation, as well as incorrect estimations of the most suitable presbyopia correcting IOLs for the patient; phone phenomena, such as halos, starburst and glare, for example in patients using presbyopia-correcting IOLs; negative dysphotopsia; peripheral aberration, and chromatic aberration. Replacing an implanted IOL that causes negative post-surgical visual outcomes for a patient can be a risky and complicated procedure. Therefore, among other needs, there exists a need to alleviate negative post-surgical visual outcomes without the need of IOL replacement.

SUMMARY

Among other aspects, certain embodiments of the present disclosure relate to improving vision in a subject with an implanted intraocular lens (IOL) without the need to replace the IOL, through the use of refractive index writing (MW).

In one aspect of the present disclosure, and in accordance with some embodiments of the present disclosure, a method of vergence matching for an intraocular lens (IOL) having an optical profile induced by refractive index writing can include the steps of: determining the direction of a plurality of rays associated with a vergence of a wavefront; determining the ray direction and ray height of a plurality of rays entering a first location of the optical profile; and determining the refractive index of the optical profile at the first location. The method can also include, based on the determined ray direction, ray height, and refractive index at the first location, and by refractive index writing, specifying the volume and shape of each voxel to match the wavefront through the direction of propagation. The method can also include bending anterior and posterior surfaces of the optical profile such that rays inside a portion of the IOL changed by refractive index writing and outside a portion of the IOL changed by refractive index writing do not change direction; and determining a second location that, for each of the rays, corresponds to the location where the respective ray exits the optical profile changed by refractive index writing.

In some embodiments, the volume and shape of each voxel match the wavefront through the direction of propagation such that the voxels decrease for converging wavefronts. In some embodiments, the volume and shape of each voxel match the wavefront through the direction of propagation such that the voxels increase for diverging wavefronts.

In some embodiments, the anterior and posterior surfaces of the optical profile are bent such that rays at the interface of the respective surfaces of the optical profile with other portions of the lens have a zero incidence. The first location can correspond to a first plane parallel to a vertical axis of the lens and the second location can correspond to a second plane parallel to the first plane. The first location can be proximate to or correspond to the anterior surface of the lens and the second location can be proximate to or correspond to the posterior surface of the lens. In some embodiments, the bent anterior and posterior surfaces are bent to define a non-zero curvature about the optical axis. In some embodiments, the refractive index writing includes applying a plurality of pulses of radiation according to a predetermined pattern. The plurality of pulses of radiation can be focused laser pulses applied according to the predetermined pattern. In some embodiments, the IOL is implanted in an eye of a subject.

In another aspect, in some embodiments a system for improving vision of a subject can include a pulsed laser system configured to apply a plurality of laser pulses to an intraocular lens (IOL) implanted in an eye of a subject and to change the refractive index of at least one selected area of the IOL by refractive index writing, wherein the IOL has an optical profile induced by refractive index writing. The system can also include a control system coupled to the pulsed laser system and configured to control the pulsed laser system to apply the plurality of laser pulses according to calculated pattern. The control system can also be configured to perform functions that include determining the direction of a plurality of rays associated with a vergence of a wavefront; determining the ray direction and ray height of a plurality of rays entering a first location of the optical profile; determining the refractive index of the optical profile at the first location; and, based on the determined ray direction, ray height, and refractive index at the first location, and by refractive index writing using the pulsed laser system, specifying the volume and shape of each voxel to match the wavefront through the direction of propagation.

In some embodiments, the control system can also be configured to calculate the pattern of laser pulses to apply. In some embodiments, anterior and posterior surfaces of the optical profile are bent such that rays inside a portion of the IOL changed by refractive index writing and outside a portion of the IOL changed by refractive index writing do not change direction. In some embodiments, the control system can be further configured to determine a second location that, for each of the rays, corresponds to the location where the respective ray exits the optical profile changed by refractive index writing. In some embodiments, the volume and shape of each voxel match the wavefront through the direction of propagation such that the voxels decrease for converging wavefronts. In some embodiments, the volume and shape of each voxel match the wavefront through the direction of propagation such that the voxels increase for diverging wavefronts.

In some embodiments, the anterior and posterior surfaces of the optical profile are bent such that rays at the interface of the respective surfaces of the optical profile with other portions of the lens have a zero incidence. In some embodiments, the anterior and posterior surfaces are bent to define a non-zero curvature about the optical axis.

In some embodiments, the first location can correspond to a first plane parallel to a vertical axis of the lens and the second location corresponds to a second plane parallel to the first plane. In some embodiments, the first location can be proximate to or corresponds to the anterior surface of the lens, and the second location can be proximate to or corresponds to the posterior surface of the lens.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale. Like reference numerals designate corresponding parts throughout the several views.

DETAILED DESCRIPTION

Figure 1A:
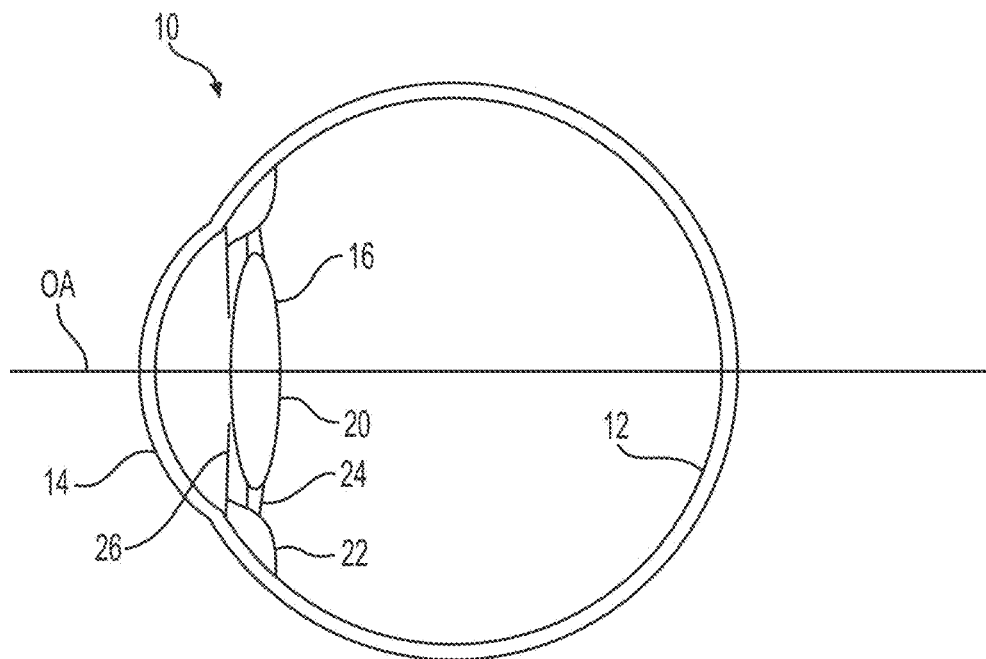
FIG. 1A illustrates a side view of an eye containing a natural lens.

Among other aspects, certain embodiments of the present disclosure relate to improving vision in a subject with an implanted intraocular lens (IOL) through the use of refractive index writing on the IOL. Refractive index writing (RIW) as described herein can utilize short pulses of focused irradiation focused on a selected area of an IOL in order to change the refractive index of the selected area and thereby modify optical performance of the IOL to correct post-surgical vision problems of the subject. For example, short and focused pulses of radiation from a visible or near-IR laser with a sufficient pulse energy can cause a nonlinear absorption of photons and lead to a change in the refractive index of the material at a focus point (in the selected area of the IOL) without affecting areas of the IOL outside of the selected area. Optical parameters of the pulsed radiation applied to the IOL, including the wavelength, pulse duration, frequency, and/energy can be configured to produce, by the refractive index writing, corrective patterns and/or structures on selected areas of the IOL to correct, e.g., to introduce a phase shift and modify the phase profile, of one or more portions of the IOL to improve vision in a subject. The pattern according to which the pulses of radiation are applied can be in the form of a determined pulse sequence, for example, with the optical parameters as mentioned above incorporated According to some embodiments of the present disclosure, the starting point of a desired refractive index implementation is a phase map that has been shown to, for example, shift power, reduce residual astigmatism, improve near vision, improve spectacle independence, or reduce visual symptoms, among other undesired vision conditions and effects as described herein with respect to various embodiments. In some embodiments according to the present disclosure, calculations such as estimates and/or various measurements may be utilized in determining (e.g, designing) a phase map that corresponds to a pattern or other element(s) to be produced on a selected area (e.g., surface, interior portion) of an IOL in order to correct unwanted visual conditions and/or effects and reach a desired result in the modified IOL design. In accordance with some embodiments, a voxel-based treatment of the IOL is applied, wherein as one goes sequentially through each voxel, the desired shift in refractive index is applied, determined by total amount of light energy focused in the particular area and the duration of focus time.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. As discussed herein, a "subject" or "patient" refers to any applicable human, animal, or other organism and may relate to specific components of the subject, in particular the eye of the subject and any applicable components such as various related muscles, tissues, and/or fluids.

As used herein, the term "optical power" of a lens or optic means the ability of the lens or optic to converge or diverge light to provide a focus (real or virtual), and is specified in reciprocal meters or Diopters (D). As used herein the terms "focus" or "focal length" of a lens or optic is the reciprocal of the optical power. As used herein the term "power" of a lens or optic means optical power. Except where noted otherwise, optical power (either absolute or add power) of an intraocular lens or associated optic is from a reference plane associated with the lens or optic (e.g, a principal plane of an optic).

As used herein, the term "near vision" means vision produced by an eye that allows a subject to focus on objects that are at a distance of, for example 40 cm or closer to a subject, such as within a range of 25 cm to 33 cm from the subject, which corresponds to a distance at which a subject would generally place printed material for the purpose of reading. As used herein, the term "intermediate vision" means vision produced by an eye that allows a subject to focus on objects that are located, for example, between 40 cm and 2 meters from the subject. As used herein, the term "distant vision" means vision produced by an eye that allows a subject to focus on objects that are, for example at a distance that is greater than 2 meters, such as at a distance of about 5 meters from the subject, or at a distance of about 6 meters from the subject, or greater.

Various aspects of the present disclosure will now be described, including aspects and embodiments discussed with reference to some example implementations and corresponding results, and the illustrations of FIGS. 1-21. Some experimental data are presented herein for purposes of illustration and should not be construed as limiting the scope of the present disclosure in any way or excluding any alternative or additional embodiments.

Referring now to FIG. 1A, a cross-sectional view of a pseudo-phakic eye 10 containing the natural lens is shown, in which eye 10 includes a retina 12 that receives light in the form of an image produced when light from an object is focused by the combination of the optical powers of a cornea 14 and a natural lens 16. The cornea 14 and lens 16 are generally disposed about an optical axis (OA). As a general convention, an anterior side is considered to be a side closer to the cornea 14, while a posterior side is considered to be a side closer to the retina 12.

The natural lens 16 is enclosed within a capsular bag 20, which is a thin membrane attached to a ciliary muscle 22 via zonules 24. An iris 26, disposed between the cornea 14 and the natural lens 16, provides a variable pupil that dilates under lower lighting conditions (mesopic or scotopic vision) and constricts under brighter lighting conditions (photopic vision). The ciliary muscle 22, via the zonules 24, controls the shape and position of the natural lens 16, allowing the eye 10 to focus on both distant and near objects. It is generally understood that distant vision is provided when the ciliary muscle 22 is relaxed, wherein the zonules 24 pull the natural lens 16 so that the capsular bag 20 and lens 16 are generally flatter and provide a longer focal length (lower optical power). It is generally understood that near vision is provided when the ciliary muscle contracts, thereby relaxing the zonules 24 and allowing the capsular bag 20 and lens 16 to return to a more rounded state that produces a shorter focal length (higher optical power).

Figure 1B:
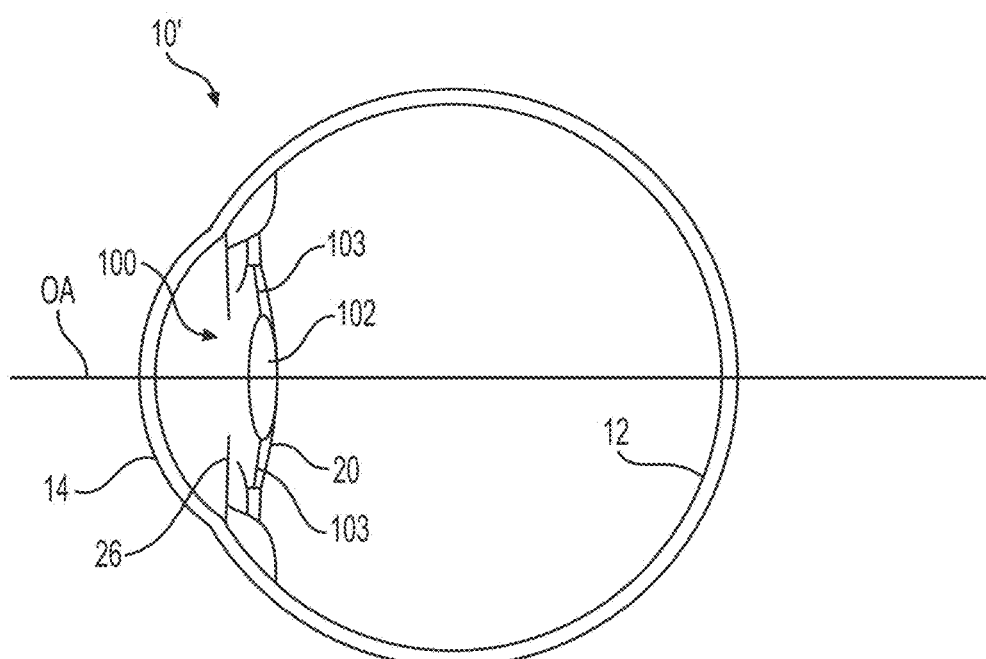
FIG. 1B illustrates a side view of the eye shown in FIG. 1A with an implanted intraocular lens (IOL).

Referring now to FIG. 1B, a cross-sectional view of an eye 10' is shown in which the natural crystalline lens 16 has been replaced by an intraocular lens (IOL) 100 according to one or more embodiments disclosed herein. The intraocular lens 100 can include an optic 102 and haptics 103, the haptics 103 being configured to at least generally center the optic 102 within the capsular bag 20, provide transfer of ocular forces to the optic 102, and the like. Numerous configurations of haptics 103 relative to optic 102 are well known within the art, and the optics edge designs described herein can generally include any of these haptic configurations. Moreover, this disclosure contemplates that the methods described herein can be used to evaluate any IOL independently of the haptics configuration and/or optics design.

Refractive Index Writing System

Figure 2:
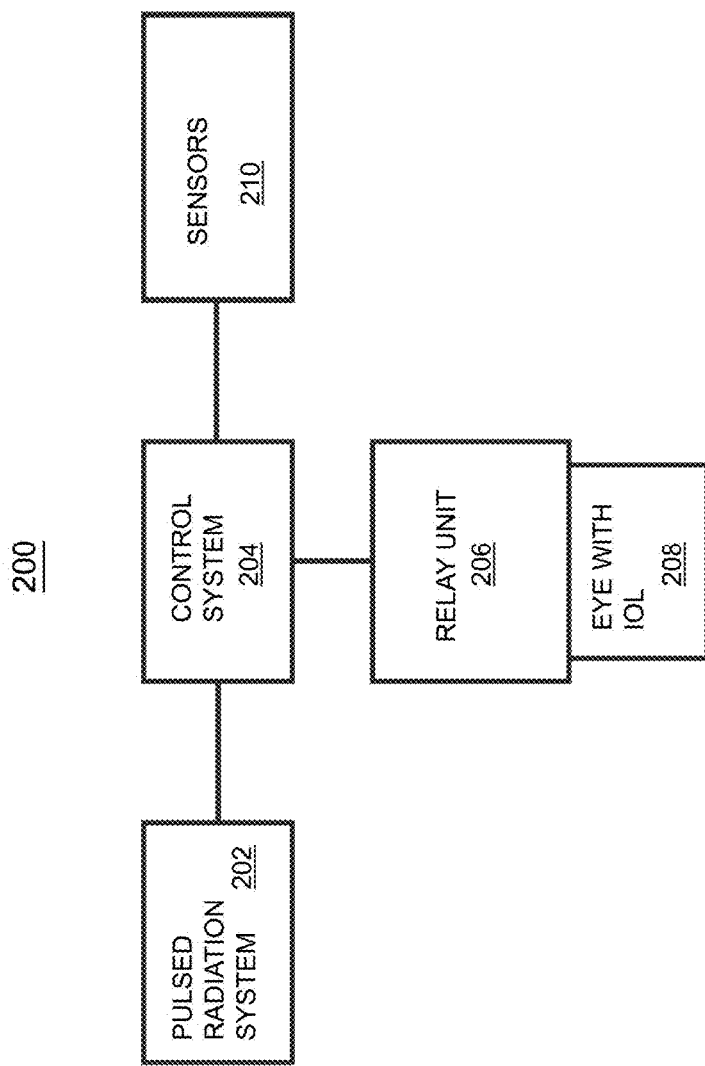
FIG. 2 is a schematic diagram of an example optical system capable of implementing one or more aspects of the present disclosure in accordance with various embodiments.

FIG. 2 shows example of a system 200 capable of implementing one or more aspects of the present disclosure in accordance with various embodiments described in further detail throughout the present description. The example system of FIG. 2 includes a pulsed radiation system 202 including a light source configured to emit radiation such as laser pulses, a control system 204, a relay unit 206, eye with an implanted IOL 208, and sensors 210.

In some embodiments, the light source of the pulsed radiation system 202 can be a femtosecond laser operating in the visible or near-infrared wavelength range, and pulsed according to a sequence (i.e., predetermined pattern of laser pulses having particular optical parameters as mentioned in some examples described below) configured to produce a desired change in the IOL 208. As some non-limiting examples, the optical parameters can include, for the emitted laser radiation pulses, a Gaussian or clipped beam profile, spot spacing between about 0.1 and 5 microns, and a pulse energy of up to about 500 nJ per pulse.

In some embodiments, sensors 210 can include an optical coherence tomography (OCT) system for determining, for example, the IOL 208 location and position (x,y,z) and/or tilt or tip with respect to the direction of the emission of radiation from the pulsed radiation system 202. The sensors 210 may alternatively or additionally include one or more of a wavefront sensor such as a Hartmann-Shack sensor, Aston Halometer, or Rostock Glare Perimeter, or other sensor(s) described herein in accordance with certain embodiments, that sense, detect, and/or measure attributes of the eye and/or IOL (208) associated with visual correction along the optical path of a subject's eye (e.g., eye 10 in FIGS. 1A and 1B) The relay unit 206, in accordance with some embodiments, is configured to deliver the laser pulses to the IOL 208 and may be configured to collect and/or direct light, for example to collect OCT light for OCT images. The relay unit 206 may include one or more optical elements such as focusing lens(es) or mirrors to correctly direct the laser pulses to the intended points of the eye and/or IOL 208

Various aspects of refractive index changes required to achieve the correction, as sensed, detected and/or measured by the sensors 210, for example, can be calculated by the use of a processor which may be, in some embodiments, included in the control system 204. The processor may be the processing unit 302 shown in the computer 300 of FIG. 3. The pulsed radiation can then be applied to the IOL at selected areas to achieve the determined correction, and the correction can subsequently be verified by the sensors 208.

In some embodiments, the control system 204 is configured to process sensed data from the sensors 210, such as obtained OCT data, to control a scanning mirror for directing the pulsed radiation (e.g., laser pulses) according to a particular scan pattern, across one or more portions of the IOL 208, and can control one or more through-focus optical elements. The control system 204, in some embodiments, is configured to receive one or more treatment and control parameters (e.g, from sensors 210) and to control the pulsed radiation system 202, which can be a pulsed laser system.

In some embodiments, the control system 204 can be configured to calculate, based on the treatment and control parameters, a pattern of laser pulses and/or selected areas of the IOL 208 to which the laser pulses are to be applied. The control system 204 can also be configured to control the pulsed laser system 202 to apply the calculated pattern of laser pulses to the calculated selected areas of the IOL 208 and thereby create a desired diffractive pattern in the IOL 208 (which can, in some embodiments, produce a phase shift). In some embodiments, the treatment and control parameters correspond to conditions (e.g., post-surgical states) and associated corrections that are needed to provide improved vision to the subject, for example residual spherical error, astigmatism, and others as described with respect to the various embodiments herein. In some embodiments, the cornea and/or anterior chamber are taken into account for the treatment and control parameters. For example, effects of refraction at the corneal surface may be taken into account to ensure that applied laser pulses are directed to an intended point within an IOL. In some embodiments, the treatment and control parameters may include specific attributes of the eye, for example the corneal topography.

In various embodiments described herein, optical parameters of radiation applied to the IOL (as part of a calculated pattern, for example) can include, but are not limited to, the wavelength, pulse duration, frequency, energy, and/or other parameters can be specifically selected to produce, by the refractive index writing, a desired result, where the specific parameters depending upon the particular embodiments as described herein in which various types of corrections are needed to address various conditions to improve the vision of the subject. In describing some embodiments of the present disclosure below, particular operating parameters and other settings of a system such as the system shown in FIG. 2 may be indicated.

Example Computing System

Figure 3:
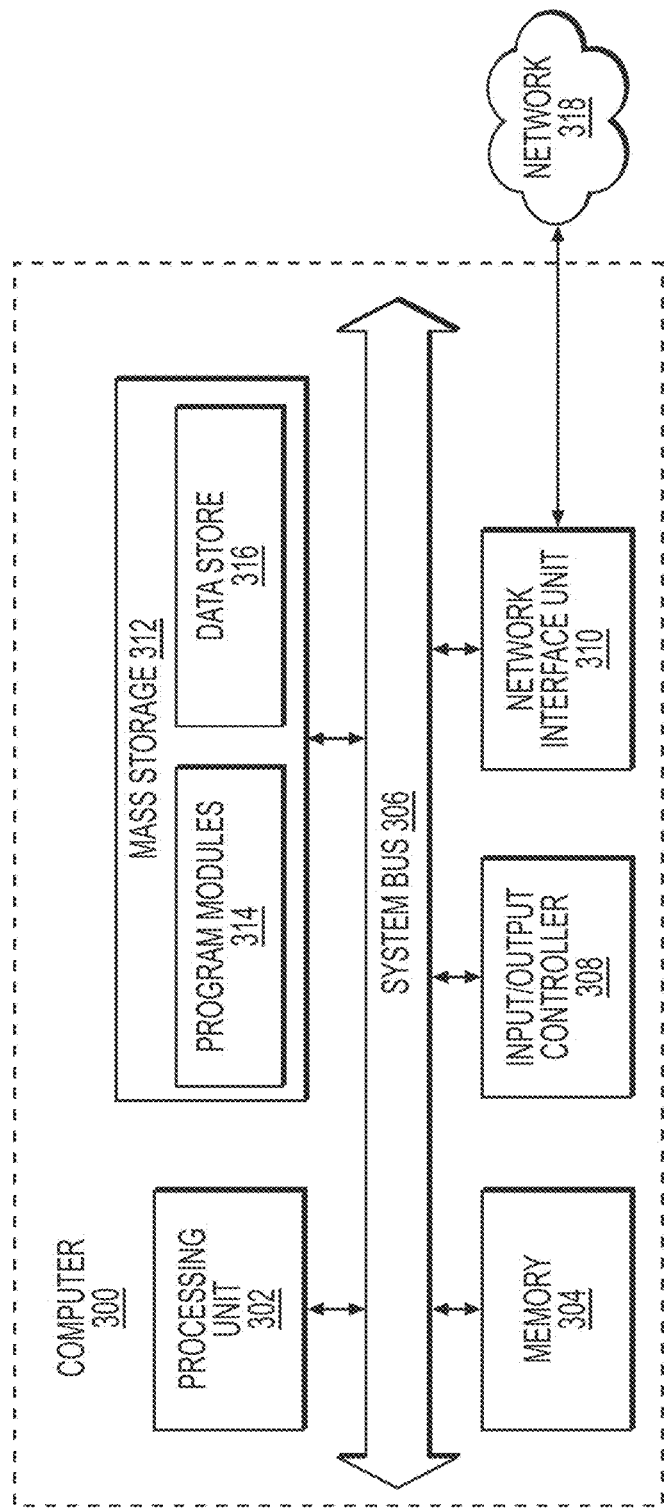
FIG. 3 shows is a diagram of an example computing system capable of performing various functions in accordance with one or more aspects and embodiments of the present disclosure.

FIG. 3 is diagram showing a general computing system capable of implementing one or more embodiments of the present disclosure described herein. Computer 300 may be configured to perform one or more functions associated with embodiments described herein, for example embodiments illustrated in one or more of FIGS. 2 and/or 4-21. It should be appreciated that the computer 300 may be implemented within a single computing device or a computing system formed with multiple connected computing devices. For example, the computer 300 may be configured for a server computer, desktop computer, laptop computer, or mobile computing device such as a smartphone or tablet computer, or the computer 300 may be configured to perform various distributed computing tasks, which may distribute processing and/or storage resources among the multiple devices.

As shown, the computer 300 includes a processing unit 302, a system memory 304, and a system bus 306 that couples the memory 304 to the processing unit 302. The computer 300 further includes a mass storage device 312 for storing program modules. The program modules 314 may include modules executable to perform one or more functions associated with embodiments illustrated in one or more of FIGS. 2 and/or 4-21. For example, the program modules 314 may be executable to perform one or more of the functions for making determinations with respect to various optical attributes, performing calculations, and/or executing software (e.g., computer-executable instructions stored on non-transitory computer-readable media) as described herein with regard to specific embodiments. The mass storage device 312 further includes a data store 316.

The mass storage device 312 is connected to the processing unit 302 through a mass storage controller (not shown) connected to the bus 306. The mass storage device 312 and its associated computer storage media provide non-volatile storage for the computer 300. By way of example, and not limitation, computer-readable storage media (also referred to herein as "computer-readable storage medium" or "computer-storage media" or "computer-storage medium") may include volatile and non-volatile, removable and non-removable media implemented in any method or technology for storage of information such as computer-storage instructions, data structures, program modules, or other data. For example, computer-readable storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 300. Computer-readable storage media as described herein does not include transitory signals.

According to various embodiments, the computer 300 may operate in a networked environment using connections to other local or remote computers through a network 318 via a network interface unit 310 connected to the bus 306. The network interface unit 310 may facilitate connection of the computing device inputs and outputs to one or more suitable networks and/or connections such as a local area network (LAN), a wide area network (WAN), the Internet, a cellular network, a radio frequency network, a Bluetooth-enabled network, a Wi-Fi enabled network, a satellite-based network, or other wired and/or wireless networks for communication with external devices and/or systems. The computer 300 may also include an input/output controller 308 for receiving and processing input from a number of input devices. Input devices may include, but are not limited to, sensors (e.g., sensors 210), keyboards, mice, stylus, touch-screens, microphones, audio capturing devices, or image/video capturing devices. An end user may utilize such input devices to interact with a user interface, for example a graphical user interface, for managing various functions performed by the computer 300.

The bus 306 may enable the processing unit 302 to read code and/or data to/from the mass storage device 312 or other computer-storage media. The computer-storage media may represent apparatus in the form of storage elements that are implemented using any suitable technology, including but not limited to semiconductors, magnetic materials, optics, or the like. The program modules 314 may include software instructions that, when loaded into the processing unit 302 and executed, cause the computer 300 to provide functions associated with embodiments illustrated in FIGS. 2 and/or 4-21. The program modules 314 may also provide various tools or techniques by which the computer 300 may participate within the overall systems or operating environments using the components, flows, and data structures discussed throughout this description. In general, the program module 314 may, when loaded into the processing unit 302 and executed, transform the processing unit 302 and the overall computer 300 from a general-purpose computing system into a special-purpose computing system.

As another example, the computer-storage media may be implemented using magnetic or optical technology. In such implementations, the program modules 314 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present disclosure.

Correcting IOL Power

Some aspects of the present disclosure relate to the use of refractive index writing to make negative or positive power additions to an implanted IOL to correct incorrect IOL power, which may be caused by pre-surgical incorrect IOL power calculations due to, for instance, limitations in biometry accuracy. Current post-surgical refractive conditions can include the need for both negative and positive power adjustment. In some embodiments, through the use of RIW to impose a phase pattern with a total phase addition of up to one lambda, with zone width calculated to achieve appropriate power change and the correct slope, both negative and positive additions can be made. Furthermore, alternative embodiments can include phase patterns with step height larger than one lambda which can achieve the desired monofocal shift.

The process to adjust the power can be planned in advance. While adding positive diffractive power can reduce longitudinal chromatic aberrations (thereby increasing image quality), adding negative diffractive power can increase it. In accordance with certain embodiments, a postsurgical refractive index writing procedure is planned in the protocol, and therefore the power calculation for an IOL to be implanted in a subject can be intentionally set to leave the subject with a spherical error requiring an estimated positive addition. For example, IOL power can be calculated to leave a subject with a spherical error of +1.5 D; with the range of expected spherical variation being 1.5 D, corrections can be made to improve a longitudinal chromatic aberration, and therefore, image quality.

Spherical aberration (spherical error) of the added power can be controlled. While a default correction mode of solely adding power induces spherical aberration (the magnitude and sign of which depends on the spherical aberration that needs to be corrected), the correction factor, in accordance with some embodiments, does not alter the overall spherical aberration; this can be achieved by having the size of each zone in $r^2$-space be non-uniform rather than fixed if the change in power is achieved with a diffractive phase pattern. Alternatively, spherical aberration can be combined with the spherical correction to modulate the refractive index change required along the r-space to create a refractive change in power. In some embodiments, some residual spherical aberration is left uncorrected, for example in cases where an extended depth of focus is desired.

In some aspects of the present disclosure, according to one embodiment, an IOL is implanted in the eye of a subject, where the IOL is configured (pre-surgery) to, when implanted, leave a non-zero residual spherical error that requires an estimated diffractive power addition in the IOL. The IOL selected may be an IOL selected that would result in a particular average error, e.g., +2.5 diopters, according to, for instance, the Haigis formula. Furthermore, the estimation-calculation of the needed positive power addition can be performed based on several factors that are specific to a particular subject. For example, the calculations can be performed based on one or more of: estimated IOL power to target refraction, subject axial length, surgeon's optimized A constant or surgical factor, and/or effective lens position (ELP). The "A constant" refers to a personalized regression factor that accounts for individual differences in technique, and "axial length" refers to the distance between apex and the cornea and the retina.

Regarding the refractive index writing, in some embodiments, a plurality of laser pulses are applied to selected area(s) of the implanted IOL, where the laser pulses are applied according to a predetermined pattern configured to produce, by the RIW, a positive diffractive power addition in the IOL that corrects for the residual spherical error and partially reduces or completely compensates for a longitudinal chromatic aberration of the eye. The applied laser pulses produce the positive diffractive power addition in the IOL in order to partially or fully correct for the longitudinal spherical chromatic aberration.

In some embodiments, the power addition does not induce further spherical aberration or modify existing spherical aberration. In other embodiments, a spherical aberration change is induced by the RIW to change the size of diffractive profile zone(s) of the IOL in $r^2$-space, such that there is non-uniform size of each zone in $r^2$-space. In order to reduce spherical aberration there is higher spacing as high $r^2$ values are approached, and in order to increase spherical aberration, there is lower spacing towards the high $r^2$ values.

In some embodiments, to compensate for the residual error(s) in the implanted IOL, a phase profile induced on the IOL by RIW is calculated based at least on the effective lens position (ELP). To create the profile, the postoperative refractive error in the spectacle plane needs to be converted to power shift on the IOL plane. In some embodiments, ELP measured during the refractive index writing procedure is utilized to calculate the correct conversion between spherical equivalent (SEQ) in the spectacle plane and power shift in the IOL plane for each individual subject using an average corneal eye or the subject's corneal power. The conversion can be implemented depending on the different eye models proposed. Refractive error is measured as, e.g., the optimal trial lenses to place outside the subject's eye to achieve emmetropia. In some embodiments, the MW treatment can be personalized to account for ELP, rather than every subject receiving the same MW treatment based on the size of the refractive error in diopters. The personalization can be calculated by various ways through implementing different IOL models, but have in common that they constitute a refractive calculation utilizing geometric optics or ray tracing simulation to achieve optimal focus on the retina.

As table 1 (below) shows for an average eye, considering the ELP in the calculations with calculations of the estimated-desired power correction to be made in the IOL can significantly impact the outcomes.

TABLE 1

| Post-operative SEQ in spectacle plane (D) | Power shift in the IOL plane (D) | |
|---|---|---|
| | ELP = 4.5 mm | ELP = 4.7 mm |
| −2 | −2.72 | −2.45 |
| −1.5 | −2.02 | −1.74 |
| −0.5 | −0.68 | −0.35 |
| 0.5 | 0.64 | 1.00 |
| 1.5 | 1.97 | 1.67 |
| 2 | 2.61 | 3.01 |

One aspect of the present disclosure relates to a method for improving vision of a subject implanted with an intraocular lens (IOL) having a non-zero residual spherical error that requires an estimated diffractive power addition in the IOL. In one embodiment, the method can include applying a plurality of laser pulses to the IOL. The laser pulses can be configured to produce, by refractive index writing on the IOL, the estimated diffractive power addition to correct for the residual spherical error.

In some embodiments, the power addition can be a positive diffractive power addition that at least partially reduces a longitudinal chromatic aberration of the eye. Applying the plurality of laser pulses can include applying a plurality of focused laser pulses according to a predetermined pattern to at least one selected area of the IOL, to produce the diffractive power addition. In some embodiments, the estimated diffractive power addition fully compensates for the longitudinal chromatic aberration. The diffractive power addition can be estimated based at least in part on at least one of: estimated IOL power to target emmetropia; a subject's axial length; surgeon's optimized A constant; and/or effective lens position (ELP). In some embodiments, the laser pulses are configured and applied to the IOL such that the power addition does not induce further spherical aberration or modify existing spherical aberration.

In some embodiments, control of the spherical aberration is performed at least in part by changing the phase profile of the IOL by refractive index writing. In some embodiments, control of the spherical aberration can be performed at least in part by changing, by the refractive index writing on the IOL, the size of diffractive profile zones in $r^2$ space. In some embodiments, a phase profile induced in the IOL to correct for residual errors is calculated based at least in part on effective lens position (ELP) measured during the refractive index writing.

According to another aspect, the present disclosure relates to a method for improving vision of a subject implanted with an IOL that has a non-zero residual spherical error. In one embodiment, the method includes applying a plurality of laser pulses to the IOL. The laser pulses can be configured to produce, by refractive index writing on the IOL, an estimated positive diffractive power addition. A phase profile induced in the IOL to correct for residual errors can be calculated based at least in part on effective lens position (ELP) measured during the refractive index writing. In some embodiments, applying the plurality of laser pulses comprises applying a plurality of focused laser pulses to at least one selected area of the IOL to produce, by the refractive index writing on the IOL, the diffractive power addition in the IOL.

In some embodiments, the diffractive power addition at least partially corrects a longitudinal chromatic aberration of the eye. The diffractive power addition can be estimated based at least in part on at least one of: estimated IOL power to target emmetropia; a subject's axial length; and surgeon's optimized A constant. In some embodiments, the laser pulses are configured and applied to the IOL such that the power addition does not induce further spherical aberration or modify existing spherical aberration. Control of the spherical aberration can be performed at least in part by changing, by the refractive index writing on the IOL, the size of diffractive profile zones in $r^2$ space.

In another aspect, the present disclosure relates to a system for improving vision of a subject. In one embodiment, the system includes a pulsed laser system configured to apply laser pulses to an intraocular lens (IOL) implanted in an eye of a subject to change the refractive index of selected areas of the lens by refractive index writing. The system can also include a control system configured to receive data regarding a non-zero residual spherical error of the eye of the subject after implantation of the IOL and estimate a diffractive power addition to the IOL required to either partially or fully correct the non-zero residual spherical error. The control system can be coupled to the pulsed laser system and configured to control the pulsed laser system to apply a plurality of laser pulses to the IOL. The laser pulses can be configured to produce, by refractive index writing on the IOL, the estimated diffractive power addition.

In some embodiments, the control system is configured to estimate the diffractive power addition such that the diffractive power addition reduces a longitudinal chromatic aberration of the eye. In some embodiments, the pulsed laser system is configured to apply a plurality of focused laser pulses to at least one selected area of the IOL to produce, by the refractive index writing on the IOL, the estimated diffractive power addition in the IOL. The estimated diffractive power addition can fully compensate for the longitudinal chromatic aberration of the eye. In some embodiments, the diffractive power addition can be estimated based at least in part on IOL power to achieve emmetropia. In some embodiments, the diffractive power addition is estimated based at least in part on the axial length of the subject's eye. In some embodiments, the diffractive power addition is estimated based at least in part on the effective lens position (ELP) of the IOL in the subject's eye.

In some embodiments, the control system is configured to control the pulsed laser system to apply the plurality of laser pulses to the IOL such that the power addition does not induce further spherical aberration or modify existing spherical aberration of the IOL. In some embodiments, at least the control system is configured to control the pulsed laser system to control spherical aberration at least in part by changing, by the refractive index writing on the IOL, the size of diffractive profile zones in $r^2$ space. The control system can be configured to estimate, based at least in part on effective lens position (ELP) measured during the refractive index writing, the phase profile induced in the IOL. In some embodiments, the system can also include a sensor to measure the non-zero residual spherical error of the eye of the subject and transmit sensed data associated with the non-zero residual spherical error to the control system.

Correcting Astigmatism

Uncorrected astigmatism results in impaired contrast sensitivity and visual acuity, which has safety implications for subjects. Although a toric IOL can be implanted to correct for corneal astigmatism, residual astigmatism is common after cataract surgery due to different factors like surgically induced astigmatism, effect of posterior corneal astigmatism, incorrect toric IOL power determination, toric IOL rotation or misplacement, and/or use of non-toric IOLs in toric corneas. A conventional procedure to calculate the zone radii of full lambda phase shift to correct for a spherical error F is to use the formula:

$$r = \sqrt{m\frac{2\lambda}{F}}$$

where $\lambda$ is the wavelength, m is a natural number (1, 2, 3, . . . ) and F the power.

In accordance with some embodiments of the present disclosure, the phase profile induction is modified to include an angular dependence; in some embodiments, the following calculation is utilized:

$$r = \sqrt{m\frac{2\lambda}{F_1 + (F_2 - F_1)|\sin\theta|}} \quad (1)$$

where $\theta$ is the angle, and F1 and F2 the power to be corrected in the respective meridians. This can be used to correct the astigmatism of the subject.

In some embodiments of the present disclosure, a method for improving vision of a subject having an implanted intraocular lens (IOL) includes the steps of: determined a modification of a phase profile on the IOL to correct an astigmatism; and applying a plurality of focused laser pulses to one or more selected areas of the IOL, where the laser pulses are configured to produce, by refractive index writing on the IOL, the determined modification of the phase profile on the IOL. Determining the modification of the phase profile includes calculating a radius of a phase shift for correcting for a residual spherical error, the radius being calculated according to factors that include an angular dependence. The radius of the phase shift can be calculated by the above-described equation (1) above.

Spectacle Independence

Spectacle dependence can be due to monofocal IOL implantation, for example, or incorrect selection of a suitable presbyopia-correcting IOL for a particular subject. Presbyopia-correcting intraocular lenses (PC IOLs) that make subjects spectacle independent can be highly desired. While spectacle independence is the expected result of cataract surgery with certain presbyopia-correcting IOLs, some subjects receiving those IOLs may still need to wear spectacles (i.e., they are still spectacle dependent) for the above-stated or other reasons. Parameters related to spectacle dependence include through-focus visual acuity of the subject, comfortable reading distance of the subject, subject biometry (such as at least one of axial length of the subject's eye IOL position, and corneal power), subject-specific reading habits (including reading distances), pupil size and subject-specific data indicating common lifestyle tasks performed by the subject and/or lighting conditions associated with respective tasks.

In accordance with some embodiments of the present disclosure, subjects who have previously had monofocal IOLs surgically implanted can benefit from a refractive index writing (MW) that produces phase profiles similar to those in presbyopia-correcting IOLs, for example phase profiles shown and described in one or more of the following published patent applications, which are incorporated herein by reference: U.S. Patent Application Publication Nos. 2018-0368972; 2019/0004335; 2019/0000433; 2019/0004221. Certain embodiments provide for the specific application of many desired phase profiles in-vivo. Further, according to some embodiments, RIW can be used to convert a particular PC IOL treatment into another that may be more suitable for the subject. For example, if the subject gets an extended depth of focus IOL but after surgery is not satisfied with near vision, refractive index writing can be used to write another design that better suits the subject's spectacle independence needs. Alternatively, if the subject is not satisfied by the distance image quality or the intermediate performance provided by a particular design aimed to provide a higher degree of spectacle independence, refractive index writing can be used to write another design with a greater quality of vision or better intermediate vision.

There is an important relationship between through focus visual acuity (VA) and rates of spectacle independence. While IOLs have an expected average through focus VA curve, which is related to expected rates of spectacle independence, individual through focus VA curves can radically differ from the expected curves, and as a result, individual subjects might need to wear spectacles. For instance, an individual subject might have a lower than expected VA at 30 cm, 40 cm, or 50 cm. In accordance with some embodiments of the present disclosure, a particular subject's through focus VA curve is measured, and the results are combined with an algorithm to predict spectacle independence from through focus VA. A multifocal addition produced by refractive index writing can be implemented to produce a certain phase change in the IOL which most optimally benefits spectacle independence for a particular subject's needs, for example improved VA at 30 cm, 40 cm, or 50 cm.

Improving spectacle independence may include improving the subject's through-focus visual acuity at one or more first distances (optionally while maintaining the subject's through-focus visual acuity at one or more second distances), extending depth of focus of the IOL, providing the IOL with at least partial presbyopia correction, improving presbyopia correction of the IOL and adapting presbyopia correction of the IOL to subject-specific requirements such as subject biometry or subject-specific lifestyle data.

Predicting the spectacle independence can, in some embodiments, utilize a Bayesian analysis method, involving calculating the probability of achieving spectacle independence for at least two IOLs based on at least one of: clinical data providing visual acuity at a second defocus position for the at least two IOLs in the population; standard deviation of pre-clinical visual acuity for the at least two IOLs at the first or the second defocus positions; clinical data providing minimum readable print size in mm in the population; modulation transfer function (MTF) at one or more frequencies at different distances for different pupil sizes; and/or area under the modulation transfer function at one or more frequencies at different distances for different pupil sizes.

The Bayesian analysis method can be expanded to incorporate other characteristics of the subjects, such as age, gender, eye length, pupil size, ethnicity, corneal aberrations, life style or combinations thereof. The Bayesian analysis method of estimating spectacle independence for different parameters can be incorporated in an IOL design and/or manufacturing process. The parameter space of IOL design allows variation of IOL characteristics such as radii of curvature, diffraction power, diffraction step height, transition zones and IOL thickness. These characteristics can be used in a ray tracing simulation software to predict through focus MTF, which can predict VA. Using Bayesian analysis, the probability of spectacle independence can be calculated, and the IOL characteristics optimized such that the highest possible spectacle independence is achieved, in conjunction with other simulated and desired constraints such as distance image quality. Bayesian analysis can also be used to predict how suitable certain treatment techniques, such as making the subjects slightly myopic postoperatively can positively affect spectacle independence. Bayesian analysis to estimate spectacle independence can also be used to select an IOL for implantation in a subject that would increase the chance of the subject to be spectacle independent for a variety of tasks such as reading, viewing a smartphone, computer use or combinations thereof.

In some embodiments, diagnostics combined with customization of IOLs using RIW can provide customized results that take into account subject-specific individualized factors including one or more of: the subject's common reading behavior, for example his/her preferred reading distance; pupil size considerations along with the lighting conditions present during common tasks the subject performs in daily life; and/or aberrations of both eyes of the subject, for optimizing binocular vision by matching the aberrations in order to result in optimal (e.g., highest) depth perception.

In one aspect, the present disclosure relates to a method for improving vision of a subject having an implanted intraocular lens (IOL). In one embodiment, the method includes applying a plurality of laser pulses to the IOL. The laser pulses can be configured to produce, by refractive index writing on the IOL, a predetermined change in phase profile of the IOL to increase spectacle independence. In some embodiments, applying the plurality of laser pulses includes applying a plurality of focused laser pulses according to a predetermined pattern to at least one selected area of the IOL to produce the predetermined change in phase profile.

In some embodiments, the predetermined change in phase profile to improve spectacle independence can be determined by performing functions that include, prior to the application of the laser pulses to the IOL, acquiring measurements that include measurements associated with subject-specific through-focus visual acuity. The functions performed can also include predicting based at least in part on the acquired measurements, an estimated phase profile for increasing near vision for the subject while maintaining distance vision, or for the increasing of distance vision for the subject while maintaining near vision and intermediate vision. In some embodiments, the phase delay is estimated based at least in part on measurements associated with subject-specific through-focus visual acuity. In some embodiments, the IOL is a multifocal IOL and the refractive index writing produces a phase profile on the IOL that changes the add power of the multifocal IOL.

In some embodiments, the change of the add power produced by the refractive index writing phase profile is calculated based on at least one of: through focus visual acuity of the subject; comfortable reading distance of the subject; and/or subject biometry. The subject biometry can include at least one of axial length of the subject's eye, IOL position, and/or corneal power.

In some embodiments, the predetermined change in phase profile is determined, prior to the application of the laser pulses to the IOL, based at least in part on: subject-specific reading habits, including reading distances; pupil size; and/or subject-specific data indicating common lifestyle tasks performed by the subject and lighting conditions associated with respective tasks. In some embodiments, the IOL is a diffractive IOL or a multifocal refractive IOL. In some embodiments, the change in phase profile is estimated by calculating the phase difference between the existing phase profile of the implanted IOL and the desired phase profile expected after the refractive index writing.

In another aspect, the present disclosure relates to a method for improving vision of a subject having an implanted intraocular lens. In one embodiment, the method can include applying a plurality of laser pulses to the IOL; the laser pulses can be configured to produce, by refractive index writing on the IOL, a predetermined change in phase profile of the IOL to increase spectacle independence. The predetermined change in phase profile can be determined at least in part on measurements associated with subject-specific through-focus visual acuity. The measurements can be acquired prior to the application of the laser pulses to the IOL. Applying the plurality of laser pulses can include applying a plurality of focused laser pulses according to a predetermined pattern to at least one selected area of the IOL to produce the predetermined change in phase profile.

In some embodiments, the predetermined change in phase profile to improve spectacle independence can be determined by performing functions that include predicting, based at least in part on the acquired measurements, an estimated phase profile for increasing near vision for the subject while maintaining distance vision, or the increasing of distance vision for the subject while maintaining near vision.

In some embodiments, the predetermined change in phase profile to improve spectacle independence can be determined by performing functions that include predicting, based at least in part on the acquired measurements, an estimated phase profile for increasing intermediate vision for the subject while maintaining distance vision, or the increasing of distance vision for the subject while maintaining intermediate vision.

In some embodiments, the predetermined change in phase profile to improve spectacle independence can be determined by performing functions that include predicting, based at least in part on the acquired measurements, an estimated phase profile for increasing intermediate vision for the patient while maintaining near vision, or the increasing of near vision for the patient while maintaining intermediate vision.

In some embodiments, the phase delay can be estimated based at least in part on measurements associated with subject-specific through-focus visual acuity. In some embodiments, the IOL can be a multifocal IOL and the refractive index writing produces a phase profile to change the add power of the multifocal IOL. In some embodiments, the change of the add power produced by the refractive index writing of the phase profile can be calculated based on: through-focus visual acuity of the subject; comfortable reading distance of the subject; and/or subject biometry. The subject biometry can include axial length, IOL position, and/or corneal power.

In some embodiments, the predetermined change in phase profile is determined, prior to the application of the laser pulses to the IOL, based at least in part on: subject-specific reading habits, including: reading distances; pupil size; and/or subject-specific data indicating common lifestyle tasks performed by the subject and lighting conditions associated with respective tasks.

In some embodiments, the IOL can be a diffractive IOL or a multifocal refractive IOL. In some embodiments, the change in phase profile is estimated by calculating the phase difference between the existing phase profile of the implanted IOL and the desired phase profile expected after the refractive index writing.

In another aspect, the present disclosure relates to a system for improving vision of a subject. In one embodiment, the system includes a pulsed laser system configured to apply a plurality of laser pulses to selected areas of an intraocular lens (IOL) implanted in an eye of a subject to change the refractive index of the selected areas by refractive index writing. The system can also include a control system configured to receive parameters related to spectacle dependence of the eye of the subject after implementation of the IOL and to calculate, based on the parameters, a pattern of laser pulses and selected areas of the intraocular lens to which the laser pulses are to be applied to provide a change in phase profile of the IOL to increase spectacle independence. The control system can be coupled to the pulsed laser system and configured to control the pulsed laser system to apply the calculated pattern of laser pulses to the calculated selected areas of the intraocular lens.

In some embodiments, the parameters related to spectacle dependence can include measurements associated with subject-specific through-focus visual acuity. In some embodiments, the control system can be configured to determine the change in phase profile. In some embodiments, determining the change in phase profile can include predicting, based at least in part on the subject-specific through-focus visual acuity measurements, an estimated phase profile for increasing near vision for the subject while maintaining distance vision, or for increasing distance vision for the subject while maintaining near vision.

In some embodiments, the parameters related to spectacle dependence include measurements associated with subject-specific through-focus visual acuity, wherein the control system is configured to determine the change in phase profile. Determining the change in phase profile can include predicting, based at least in part on the subject-specific through-focus visual acuity measurements, an estimated phase profile for increasing intermediate vision for the subject while maintaining distance vision, or increasing distance vision for the subject while maintaining intermediate vision.

In some embodiments, the parameters related to spectacle dependence include measurements associated with subject-specific through-focus visual acuity, wherein the control system is configured to determine the change in phase profile, and wherein determining the change in phase profile can include: predicting, based at least in part on the subject-specific through-focus visual acuity measurements, an estimated phase profile for increasing intermediate vision for the subject while maintaining near vision, or for increasing near vision for the subject while maintaining intermediate vision. In some embodiments, the control system can be configured to estimate phase delay based at least in part on measurements associated with subject-specific through-focus visual acuity. In some embodiments, the IOL can be a multifocal IOL and the refractive index writing can produce a phase profile on the IOL that changes the add power of the multifocal IOL.

In some embodiments, the control system can be configured to calculate the change of the add power produced by the refractive index writing phase profile based on at least one of: through-focus visual acuity of the subject; comfortable reading distance of the subject; and/or subject biometry. In some embodiments, the subject biometry can include axial length of the subject's eye, IOL position, and/or corneal power.

In some embodiments, the control system can be configured to determine the change in phase profile, prior to the application of the laser pulses to the IOL, based at least in part on: subject-specific reading habits, including reading distances; pupil size; and/or subject-specific data indicating common lifestyle tasks performed by the subject and/or lighting conditions associated with respective tasks. In some embodiments, the parameters related to spectacle dependence include: through-focus visual acuity of the subject; comfortable reading distance of the subject; subject biometry, such as at least one of axial length of the subject's eye, IOL position, and/or corneal power; subject-specific reading habits, including reading distances; pupil size; and/or subject-specific data indicating common lifestyle tasks performed by the subject and/or lighting conditions associated with respective tasks. In some embodiments, the IOL can be a diffractive IOL or a multifocal refractive IOL.

In some embodiments, the change in phase profile can be estimated by calculating a phase difference between an existing phase profile of the implanted IOL and a desired phase profile expected after the refractive index writing. In some embodiments, improving spectacle independence includes one or more of: improving the subject's through-focus visual acuity at one or more distances; improving the subject's through-focus visual acuity at one or more first distances while maintaining the subject's through-focus visual acuity at one or more second distances; extending depth of focus of the IOL; providing the IOL with at least partial presbyopia correction; improving presbyopia correction of the IOL; and adapting presbyopia correction of the IOL to subject-specific requirements, such as subject biometry or subject-specific lifestyle data.

Photic Phenomenon

Unwanted visual symptoms due to the presence of unwanted light for subjects, also referred to herein as "photic phenomenon" include but are not limited to: halos, starbursts, and glare. Such unwanted visual symptoms tend to be more commonly experienced in subjects after the surgical implantation of a presbyopia-correcting intraocular lenses. For multifocal IOLs, the out of focus light can form a halo around the main image. The presence of unwanted visual symptoms strongly depends on the specific IOL design, but there is also a significant subjective component. For that reason, for two subjects with similar objective ocular conditions, one may not experience unwanted visual symptoms while the other may experience them and express complaints about the condition. Although medical professionals can make great efforts to select monofocal refractive IOLs for subjects with a high risk of experiencing unwanted post-surgical visual symptoms, such symptoms can be difficult to predict, particularly on a subject-by-subject basis.

Figure 4:
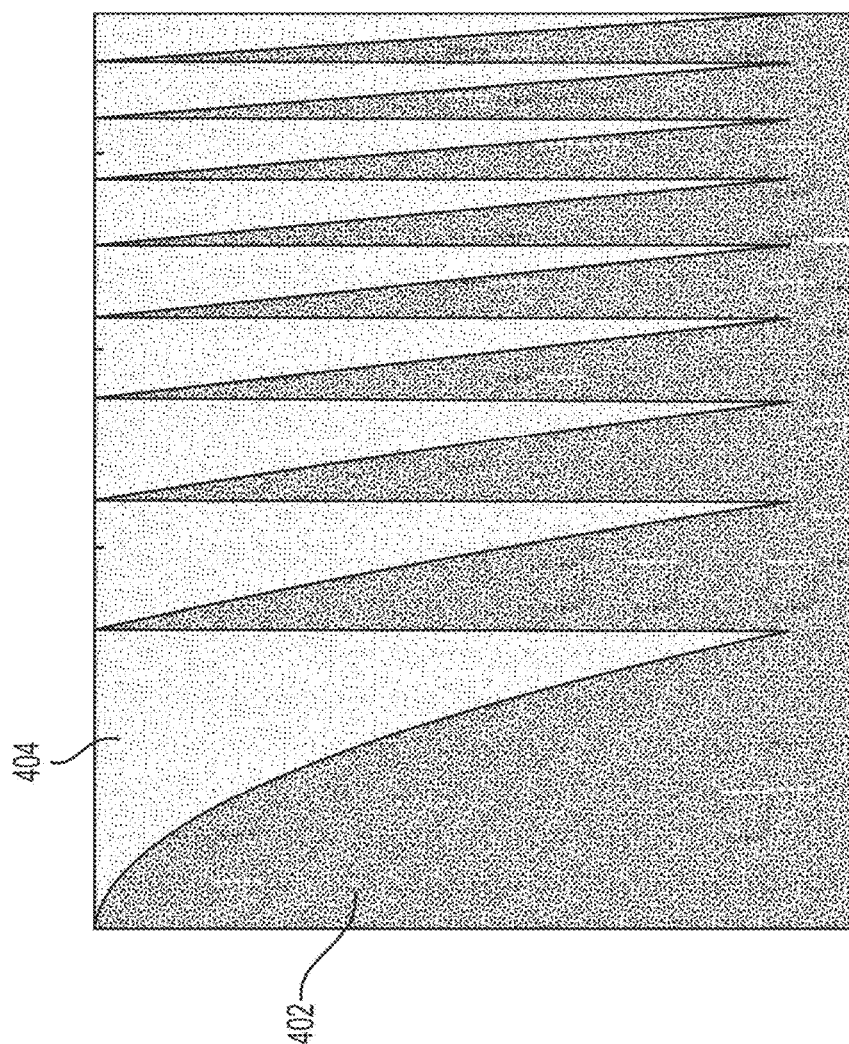
FIG. 4 illustrates phase addition of a presbyopia-correcting IOL and the phase addition needed to be introduced, by refractive index writing, to remove unwanted visual symptoms, in accordance with some embodiments of the present disclosure.

As mentioned above, while medical professionals can go to great length to ensure subject expectations are managed prior to IOL implantation surgery, some subjects nevertheless realize after surgery that they would have preferred a monofocal IOLs or a lens that would provide a lower degree of photic phenomena. Rather than requiring the IOL to be surgically replaced, which can be a complicated and risky procedure, in accordance with some embodiments of the present disclosure refractive index writing is used to remove or substitute the optical design causing the unwanted visual symptoms. As shown in FIG. 4, according to one example implementation, the diffractive profile 402 introduces a radially dependent phase shift; this phase shift also creates unwanted visual symptoms. According to some embodiments, a radially dependent phase shift 404 is introduced to compensate, such that the IOL can be rendered monofocal, removing the unwanted visual symptoms. That is, in FIG. 4, the portion 402 illustrates phase addition of a presbyopia-correcting IOL, and the portion 404 illustrates the phase addition needed to be introduced, by refractive index writing, to remove the unwanted visual symptoms. In some embodiments of the presented disclosure, the phase delay introduced by a diffractive IOL is fully compensated. In other embodiments of the present disclosure, a partial compensation of the profile may be performed, or the creation of another profile that is expected to create less visual disturbances for a particular subject and therefore a better quality of vision.

In some embodiments as discussed above, a phase-compensation technique by RIW is used to eliminate all visual symptoms of a diffractive and refractive IOL, by fully compensating the added phase. This can also eliminate the spectacle independence created by the IOL, however. In accordance with some embodiments, a subject-specific, personalized approach is taken that can enable certain subjects to receive a desirable compromise of reduced unwanted visual symptoms and maintained spectacle independence. In accordance with some embodiments of the present disclosure described below, this compromise-type approach can include: 1. a personalized diagnostic procedure mapping when intolerable levels of visual symptoms occur; 2. a personalized correction involving refractive optimization, apodization, and/or profile reversion; and 3. a diagnostic procedure verifying satisfactory reduction of unwanted visual symptoms.

In some embodiments, the use of such approaches can be combined with simulated optical manipulations, including modulating the pupil size, and higher order aberrations. Certain pupil sizes and higher order aberrations interact with the diffractive design to exacerbate the visual symptoms, and this step would measure this on a personalized level.

With respect to the above-mentioned personalized diagnostic procedure mapping when intolerable levels of visual symptoms occur, fully subjective, psychophysical, and/or objective approaches can be used for measuring and mapping unwanted visual symptoms, including halos, glare and starbursts. These may include one or more aspects and embodiments shown and described in U.S. patent application Ser. No. 16/271,648, entitled "Psychophysical Method to Characterize Visual Symptoms", filed Feb. 8, 2019, which is hereby incorporated by reference. Fully subjective approaches include, for example, the use of questionnaires to solicit feedback from a particular subject in order to receive, for instance, descriptions and/or drawings that articulate the photic phenomena he/she is experiencing. Psychophysical approaches include, for example, use of commercially available devices such as an Aston Halometer and/or a Rostock Glare Perimeter, which can quantify halos. Objective approaches can include wavefront-based methods, such as the Objective Scatter Index.

With respect to the above-mentioned personalized correction involving refractive optimization, apodization, and/or profile reversion, refractive optimization includes correcting one or more of defocus, astigmatism, and higher order aberrations. Regarding apodization, the peripheral part of the diffractive design, e.g., 4 mm and higher diameter, or 3 mm and higher diameter, can be eliminated, while the central part can be kept; additionally, multifocality can be modified in the peripheral part of the IOL to allow a different light distribution between the different foci, for example, to increase the amount of light that goes to the far focus and therefore, reducing the amount of light that goes to the near and/or focus. The diameter can be chosen based on individual results. In profile reversion, the full multifocal profile of the IOL is eliminated and a monofocal profile created.

With respect to the above-mentioned verification of satisfactory reduction of unwanted visual symptoms for the subject, through a diagnostic procedure, refractive optimization, apodization, and/or profile reversion can be done independently or sequentially to eliminate unwanted visual symptoms. Additionally, apodization can be performed using subject feedback by eliminating multifocality in the outer parts of the IOL and, if more reduction is desired, a further elimination of multifocality to a lower radius.

In some embodiments, refractive index writing is implemented to provide a phase addition that simulations show would decrease the unwanted visual phenomenon. For example, if a subject complains about halo effects, then the added phase is configured such that it results in smaller magnitude of light outside the focus according to simulations. As another example, if a subject complained about experiencing rings and spiderwebs, then the simulation should result in lower variance in simulated light levels (light intensity going up and down as a function of radius). According to some embodiments, this can be particularly useful to simulate on an individual basis to include the interaction effect between higher order aberrations and unwanted visual symptoms.

In one aspect, the present disclosure relates to a method for improving vision of a subject having an implanted intraocular lens (IOL). In one embodiment, the method includes determining at least one photic phenomenon experienced by the subject after implantation of the IOL; and applying a plurality of laser pulses to the IOL. The laser pulses can be configured to produce, by refractive index writing on the IOL, a phase shift in the IOL to compensate for the phone phenomenon.

In some embodiments, applying the plurality of laser pulses includes applying a plurality of focused laser pulses, according to a predetermined pattern, to at least one selected area of the IOL to produce, by the refractive index writing on the IOL, the phase shift. The phone phenomenon can include a halo, starburst, and/or glare. In some embodiments, the phase shift can include a radially dependent phase shift. In some embodiments, the method can include verifying correction of the at least one photic phenomenon following the application of the laser pulses. Verifying the correction can be performed by incorporating subject feedback provided following the application of the laser pulses.

In some embodiments, the IOL is a diffractive IOL or a refractive IOL and compensating for the photic phenomena includes at least partially compensating for the phase delay. In some embodiments, determining the photic phenomena can include measuring and mapping the phone phenomenon experienced by the subject. Determining the phase delay to compensate for at least one photic phenomena can include simulations of the optimal higher order aberrations induction based on pupil size analysis. The simulations of the optimal higher order aberrations induction can be based on subject response to photic phenomena.

In some embodiments, compensating for the photic phenomenon includes refractive optimization, apodization, partial apodization, and/or profile reversion. The refractive optimization can include correcting, by the refractive index writing, at least one of defocus, astigmatism, and higher order aberrations. The apodization can include eliminating, by inverted phase delay, the diffractive or refractive IOL design in an outer part of the lens. The apodization phase delay can be determined using feedback from the subject relating to experiencing the phone phenomena. The apodization can include maintaining a central part of the diffractive design, where the peripheral part is defined based on the specific photic phenomenon experienced by the subject.

In some embodiments, the partial apodization includes modifying the percentage of light distributed between different foci of a multifocal IOL in an outer part of the lens. The profile reversion can include eliminating the full diffractive profile of the IOL.

As an example, an adaptive optics (AO) system can be used to evaluate the level of higher-order aberrations that are needed to correct for the photic phenomenon, controlling the pupil size. The measurement of individual aberrations can be performed using, for example, wavefront sensors such as Hartmann-Shack sensors, and specialized software may be utilized to calculate an optimal phase map for the refractive index writing. In some embodiments, the simulations of the optimal higher order aberrations induction are based on subject response to photic phenomena.

In some embodiments, correcting the higher order aberrations to compensate for the phone phenomenon can include performing an iterative, closed-loop correction process to correct one or more of the higher order aberrations of the subject. In some embodiments, the closed-loop correction process includes measuring the higher order aberrations associated with the vision of the subject and determining, based at least in part on the measurements, a target higher order aberration correction that can be at least one of: full correction of at least one of the higher order aberrations of the subject; partial correction of at least one of the higher order aberration of the subject; and induction of at least one higher order aberration. The method can also include applying a plurality of focused laser pulses to selected areas of the IOL, where the laser pulses are configured to produce, through refractive index writing, a target higher order aberration correction profile on the IOL.

In some embodiments, the above-described closed-loop method also includes the steps of determining if the produced correcting profile meets the determined profile and, responsive to determining that the produced correcting profile does not meet the determined profile: measuring the difference between the higher order aberrations profile of the eye after the laser treatment and the target higher order aberrations correction and using this information to calculate the determined profile to achieve the target higher order aberration correction, and, based at least in part on the measured difference, applying a plurality of focused laser pulses to the IOL for refractive index writing, where the configuration of the laser pulses are modified from the prior applied laser pulses based on the measured difference, and repeating the above steps until the produced higher order aberration correcting profile meets the determined target higher order aberration correction.

In another aspect, the present disclosure relates to a system for improving vision of a subject. In one embodiment, the system includes a pulsed laser system configured to apply laser pulses to an intraocular lens (IOL) implanted in an eye of a subject to change the refractive index of selected areas of the lens by refractive index writing. The system can also include a control system configured to receive data regarding a photic phenomenon of the eye of the subject after implantation of the IOL and use the received data to calculate a pattern of laser pulses and/or selected areas of the IOL to which the laser pulses are to be applied to produce a phase shift to compensate for the photic phenomenon. The control system can be coupled to the pulsed laser system and configured to control the pulsed laser system to apply the calculated pattern of laser pulses to the calculated selected areas of the IOL in order to produce, by refractive index writing on the IOL, the phase shift to compensate for the photic phenomenon. In some embodiments, the photic phenomenon can include a halo, starburst, and/or glare.

In some embodiments, the control system can be configured to calculate the pattern of laser pulses and the selected areas of the IOL to produce a radially dependent phase shift. In some embodiments, the control system can be configured to calculate the pattern of laser pulses and the selected areas of the IOL to at least partially compensate for the phase delay of a diffractive IOL or a refractive IOL.

In some embodiments, the system can also include at least one sensor coupled to the control system. The at least one sensor can be configured to collect data regarding the pupil size of the subject and transmit the data regarding pupil size to the control system. The control system can be configured to compensate for the phase delay by using the data regarding pupil size to run simulations of optimal higher order aberrations to induce in the IOL to compensate for the phone phenomenon; and the control system can be configured to calculate the pattern of laser pulses and the selected areas of the IOL to induce the optimal higher order aberrations. In some embodiments, the simulations of the optimal higher order aberrations induced are based on subject response to photic phenomena.

In some embodiments, compensating for the photic phenomenon can include: refractive optimization, apodization, partial apodization, and/or profile reversion. In some embodiments, the refractive optimization includes correcting, by the refractive index writing, at least one of defocus, astigmatism, and higher order aberrations.

In some embodiments, the apodization can include eliminating, by inverted phase delay, the diffractive or refractive IOL design in an outer part of the lens. In some embodiments, the apodization can also include maintaining a central part of the diffractive design, wherein the peripheral part is defined based on the specific photic phenomenon experienced by the subject.

In some embodiments, the partial apodization can include modifying the percentage of light distributed between different foci of a multifocal IOL in an outer part of the lens. In some embodiments, the profile reversion can include eliminating the full diffractive profile of the IOL.

In some embodiments, the system can include at least one sensor coupled to the control system to measure higher order aberrations, and compensating for the photic phenomenon can include correcting the higher order aberrations. The control system can be configured to perform an iterative, closed-loop correction process to correct the higher order aberrations.

Negative Dysphotopsia

Negative dysphotopsia (ND) can be characterized by subjective reports and complaints from subjects having an intraocular lens (IOL) implanted, where the complaints describe the presence of a dark shadow in the far periphery. A number of subject factors, including small photopic pupil, high angle kappa and hyperopia, have been identified as increasing the risk of ND. The presence of ND is likely caused by absence of light in the retinal interval between light passing through and refracted by the IOL (e.g., at lower angles of incidence) and rays missing the IOL (e.g., at higher angles of incidence). While the light passing the IOL at the lower angles of incidence is refracted, changing its direction to a lower angle, the light at the higher angles miss the IOL and continue straight without deviation, thereby creating an angular interval on the retina that is not illuminated. The problem is partially alleviated at larger pupil sizes, since optical errors create larger deviations of rays at the pupil edge which partially hits the obscured part of the peripheral retina.

As described above, negative dysphotopsia can result if there is a discontinuity in ray deviation between rays missing the IOL and rays being refracted by the IOL. In order to address this condition, in accordance with some embodiments of the present disclosure, a gradual outer phase prism is applied in the outermost part of the IOL (e.g., 0.5 mm from the edge of optic body) using refractive index writing procedure in subjects that complain of ND after IOL implantation. The result can be to gradually deviate the chief ray, bridging the gap between rays missing and rays being refracted by the IOL, eliminating or reducing the shadow. The phase prism can be defined based on the power of the IOL (e.g., from 5.0 to 34.0 D) and the extension of the prism (from the edge to the center of the IOL). The procedure can be independent of the IOL design (refractive or diffractive) and the IOL platform.

Consistent with one or more aspects described above, and in accordance with some embodiments of the present disclosure, a method for improving vision of a subject having an implanted intraocular lens (IOL) can include determining parameters of a phase prism to be produced on the IOL to correct negative dysphotopsia, where the determining comprising defining the phase prism based on power of the IOL and extension of the prism from respective outer edges of the IOL to the center of the IOL. The method can also include applying a plurality of focused laser pulses to the IOL at the selected areas, where the laser pulses are configured to produce, through refractive index writing on the IOL, the phase prism having the determined parameters in at least one outermost portion proximate the outer edges of the IOL. In some embodiments, the phase prism, as produced by the RIW on the IOL, is configured to gradually deviate a chief ray to correct a discontinuity in ray deviation between rays missing the IOL and rays being refracted by the IOL.

Personalized Correction of Higher Order Aberrations

The average cornea has +0.27 μm spherical aberration at a 6 mm pupil. Correcting this average spherical aberration can increase contrast sensitivity and, among other benefits, improve a subject's driving safety. However, the average root mean square of higher order aberrations is around 0.5 μm. In accordance with some embodiments of the present disclosure, correcting for individual, subject-specific higher order aberrations can be accomplished through the use of refractive index writing on the IOL, since IOL placement is final and will not move.

In accordance with some embodiments of the present disclosure, an iterative corrective approach is performed to address higher order aberrations. In some embodiments, the iterative approach includes the steps of: 1) measuring the subject's higher-order aberrations; 2) calculating the difference (from the current state) to a desired higher order aberration profile, and 3) producing the desired higher order aberration profile via refractive index writing. Steps 1 to 3 can be repeated until the desired profile is reached in a closed loop iteration. The step of measuring the higher-order aberrations, and the step of calculating the difference, can be performed at least in part using a wavefront sensor, for example a Hartmann-Shack wavefront sensor.

In some embodiments, correction of circularly symmetric aberrations such as spherical aberration can be performed through selectively altering the zone width depending on radius and angle of the IOL position, and circularly asymmetric aberrations can be corrected by altering the zone width depending on angular location. As an example implementation, the correction of personalized higher order aberrations can significantly improve the visual outcomes subjects implanted with spherical IOLs (who tend to have large amounts of positive spherical aberrations).

Consistent with one or more aspects described above, and in accordance with some embodiments of the present disclosure, a method for improving vision of a subject having an implanted intraocular lens (IOL) can include performing an iterative, closed-loop correction process to correct one or more of the higher order aberrations of the subject. In some embodiments, the closed-loop correction process includes measuring the higher order aberrations associated with the vision of the subject and determining, based at least in part on the measurements, a target higher order aberration correction that can be at least one of: full correction of at least one of the higher order aberrations of the subject; partial correction of at least one of the higher order aberration of the subject; and induction of at least one higher order aberration. The method also includes applying a plurality of focused laser pulses to selected areas of the IOL, where the laser pulses are configured to produce, through refractive index writing, a target higher order aberration correction profile on the IOL.

In some embodiments, the method also includes a closed-loop method that includes the steps of determining if the produced correcting profile meets the determined profile and, responsive to determining that the produced correcting profile does not meet the determined profile: measuring the difference between the higher order aberrations profile of the eye after the laser treatment and the target higher order aberrations correction and using this information to calculate the determined profile to achieve the target higher order aberration correction, and, based at least in part on the measured difference, applying a plurality of focused laser pulses to the IOL for refractive index writing, where the configuration of the laser pulses are modified from the prior applied laser pulses based on the measured difference, and repeating the above steps until the produced higher order aberration correcting profile meets the determined target higher order aberration correction.

Ocular Diseases

Ocular diseases are often gradual and occur with advanced age, after cataract surgery has been performed. Ocular diseases can cause loss in central visual performance (e.g., age-related macular degeneration) or at more peripheral locations (e.g., glaucoma). In accordance with some aspects of the present disclosure, there are several treatment modalities utilizing refractive index writing to address ocular diseases.

A common factor for many ocular diseases is an increased need for ocular contrast. There are different ways to improve the contrast in these subjects, using refractive index writing in accordance with embodiments of the present disclosure. In some embodiments, these ways of improvement include one or more of inscribing correction of longitudinal chromatic correction through a diffractive pattern to increase contrast, and by correcting higher order aberrations.

Macular degeneration is an ocular disease known to cause retinal damage. According to some embodiments of the present disclosure, refractive index writing is utilized to cause a yellowing of the IOL such that more harmful short wavelength light rays are absorbed, which is particularly beneficial for further preventing retinal damage caused macular degeneration. Subjects with macular degeneration can experience a positive magnification in vision that makes the world appear bigger. On the other hand, subjects with, for example glaucoma or hemianopia may benefit from a minification, making the world smaller, since they can suffer from a loss of outer peripheral vision which makes navigation more difficult, and a minified view of the world can fit more of the visual field within their functioning vision. It is known that wearing spectacles with a positive power results in a magnified view of the world, and that wearing negative spectacles results in a minified view of the world. In some embodiments of the present disclosure, refractive index writing is used to produce a refractive outcome needing either positive or negative spectacle correction, to have the desired effect for the refractive outcome and spectacle magnification. Subjects with certain ocular diseases may suffer from reduced quality of peripheral vision. In accordance with some embodiments of the present disclosure, gradient-index patterns can be applied to an implanted IOL by refractive index writing.

According to one aspect, the present disclosure relates to a method for improving vision of a subject having an implanted intraocular lens (IOL). The method can include: determining visual needs of a subject that are associated with an ocular disease of the subject and determining a pattern of a plurality of pulses of radiation (e.g., plurality of focused laser pulses) to apply, by refractive index writing, to one or more selected areas of the IOL. The plurality of pulses can be configured to induce a change in the implanted IOL to adapt the optical performance of the IOL to at least one of the visual needs of the subject. The method can also include applying, according to the determined pattern, the plurality of pulses of radiation to the one or more selected areas of the IOL.

In some embodiments, adapting the optical performance of the IOL to the visual needs of the subject can include increasing ocular contrast by inscribing a diffractive pattern in the IOL that is configured to correct longitudinal chromatic aberration. In some embodiments, adapting the optical performance of the IOL to the visual needs of the subject can include increasing ocular contrast by correcting a higher-order aberration.

Adapting the optical performance of the IOL to the visual needs of the subject can additionally or alternatively include one or more of: producing a yellowing of at least a part of the IOL, wherein short wavelength light rays are absorbed; modifying the power of the IOL to correct for residual refractive errors (e.g., defocus and astigmatism); modifying the power of the IOL to improve vision for a given distance (e.g., far correction, near correction, intermediate correction); modifying the phase profile of the IOL to remove an existing diffractive or multifocal refractive profile in the IOL; modifying the phase profile of the IOL to redirect the light passing through the IOL to the subject-preferred retinal location (PRL); and/or inducing a gradient-index pattern on the IOL that is configured to improve peripheral vision of the subject.

In some embodiments, the residual refractive error can be a residual spherical error associated with an uncorrected astigmatism, and determining the pattern of the plurality of pulses of radiation to apply can include calculating a radius of a phase shift for correcting for a residual spherical error. The radius can be calculated according to factors that include an angular dependence. The radius of the phase shift can be calculated, at least in part, according to:

$$r = \sqrt{m \frac{2\lambda}{F_1 + (F_2 - F_1)|\sin\theta|}}$$

where $\lambda$ is the wavelength, m is a natural number, $\theta$ is the angle, and F1 and F2 the power to be corrected in the respective meridians.

In some embodiments, adapting the optical performance of the IOL to the visual needs of the subject can include determining parameters of a phase prism to be produced on the IOL to correct negative dysphotopsia of the subject. Determining the parameters can include defining the phase prism based on power of the IOL and extension of the prism from respective outer edges of the IOL to the center of the IOL. Determining the pattern of a plurality of pulses of radiation to apply can include determining a pattern of a plurality of pulses of radiation to apply to produce, through refractive index writing on the IOL, wherein the phase prism has the determined parameters. In some embodiments, the one or more selected areas of the IOL include at least one outermost portion proximate the outer edges of the IOL. In some embodiments, the phase prism, as produced on the IOL, is configured to gradually deviate a chief ray to correct a discontinuity in ray deviation between rays missing the IOL and rays being refracted by the IOL.

In another aspect, the present disclosure relates to a system for treating an ocular disease of a subject having an implanted intraocular lens (IOL). In some embodiments, the system can include a pulsed laser system configured to apply, according a determined pattern, a plurality of focused laser pulses to one or more selected areas of the IOL. The system can also include a control system coupled to the pulsed laser system and configured to control the pulsed laser system to apply the plurality of focused laser pulses. The control system can also be configured to: determine visual needs of a subject that are associated with an ocular disease of the subject; and determine the pattern of a plurality of laser pulses to apply, by refractive index writing, to the one or more selected areas of the IOL. The plurality of laser pulses can be configured to induce a change in the implanted IOL to adapt the optical performance of the IOL to the visual needs of the subject.

In some embodiments, adapting the optical performance of the IOL to the visual needs can include increasing ocular contrast by inscribing a diffractive pattern in the IOL that is configured to correct longitudinal chromatic aberration. In some embodiments, adapting the optical performance of the IOL to the visual needs can include increasing ocular contrast by correcting a higher-order aberration. In some embodiments, adapting the optical performance of the IOL to the visual needs can include producing a yellowing of at least a part of the IOL, wherein short wavelength light rays are absorbed.

In some embodiments, adapting the optical performance of the IOL to the visual needs can include modifying the power of the IOL to correct for at least one residual refractive error. The at least one residual refractive error can include defocus and/or astigmatism. In some embodiments, he at least one residual refractive error can be a residual spherical error associated with an uncorrected astigmatism.

In some embodiments, determining the pattern of the plurality of laser pulses to apply can include calculating a radius of a phase shift for correcting for a residual spherical error. The radius can be calculated according to factors that include an angular dependence. In some embodiments, the radius of the phase shift can be calculated, at least in part, according to:

$$r = \sqrt{m \frac{2\lambda}{F_1 + (F_2 - F_1)|\sin\theta|}}$$

where $\lambda$ is the wavelength, m is a natural number, $\theta$ is the angle, and F1 and F2 the power to be corrected in the respective meridians.

In some embodiments, adapting the optical performance of the IOL to the visual needs can include modifying the power of the IOL to improve vision for a given distance. In some embodiments, adapting the optical performance of the IOL to the visual needs can include modifying the phase profile of the IOL to remove an existing diffractive or multifocal refractive profile in the IOL. In some embodiments, adapting the optical performance of the IOL to the visual needs can include modifying the phase profile of the IOL to redirect light passing through the IOL to the subject's preferred retinal location (PRL). In some embodiments, adapting the optical performance of the IOL to the visual needs can include inducing a gradient-index pattern on the IOL that is configured to improve peripheral vision of the subject.

In some embodiments, adapting the optical performance of the IOL to the visual needs can include determining parameters of a phase prism to be produced on the IOL to correct negative dysphotopsia of the subject; the determining can include defining the phase prism based on power of the IOL and extension of the prism from respective outer edges of the IOL to the center of the IOL. Determining the pattern of laser pulses to apply can include determining a pattern of a plurality of laser pulses to apply to produce, through refractive index writing on the IOL, the phase prism having the determined parameters.

In some embodiments, the one or more selected areas of the IOL can include at least one outermost portion proximate the outer edges of the IOL. In some embodiments, the phase prism, as produced on the IOL, can be configured to gradually deviate a chief ray to correct a discontinuity in ray deviation between rays missing the IOL and rays being refracted by the IOL.

IOL Positioning

Figure 5A:
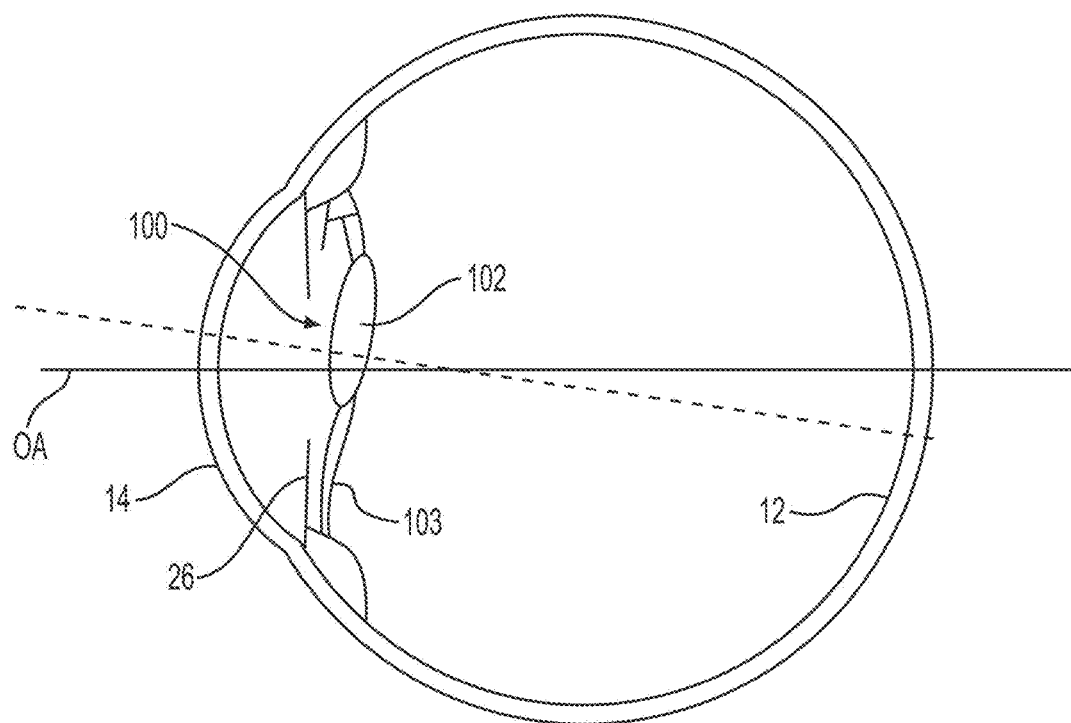
FIG. 5A is an illustration of an IOL tilted with respect to the optical axis OA.
Figure 5B:
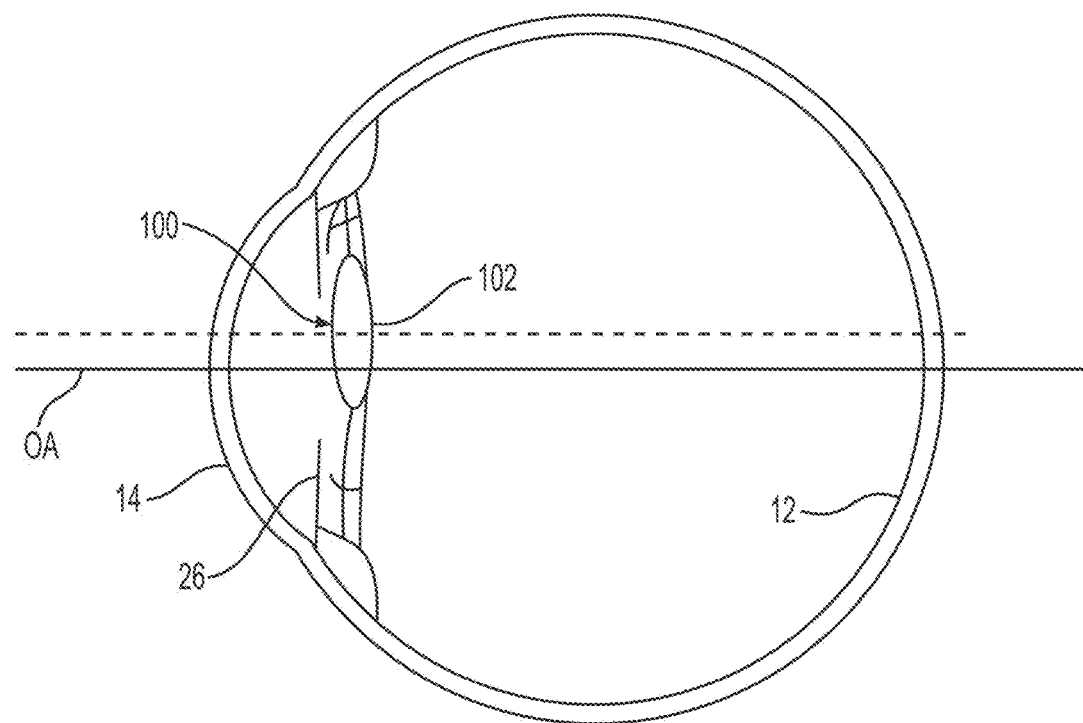
FIG. 5B is an illustration of an IOL decentered with respect to the optical axis OA.
Figure 6A:
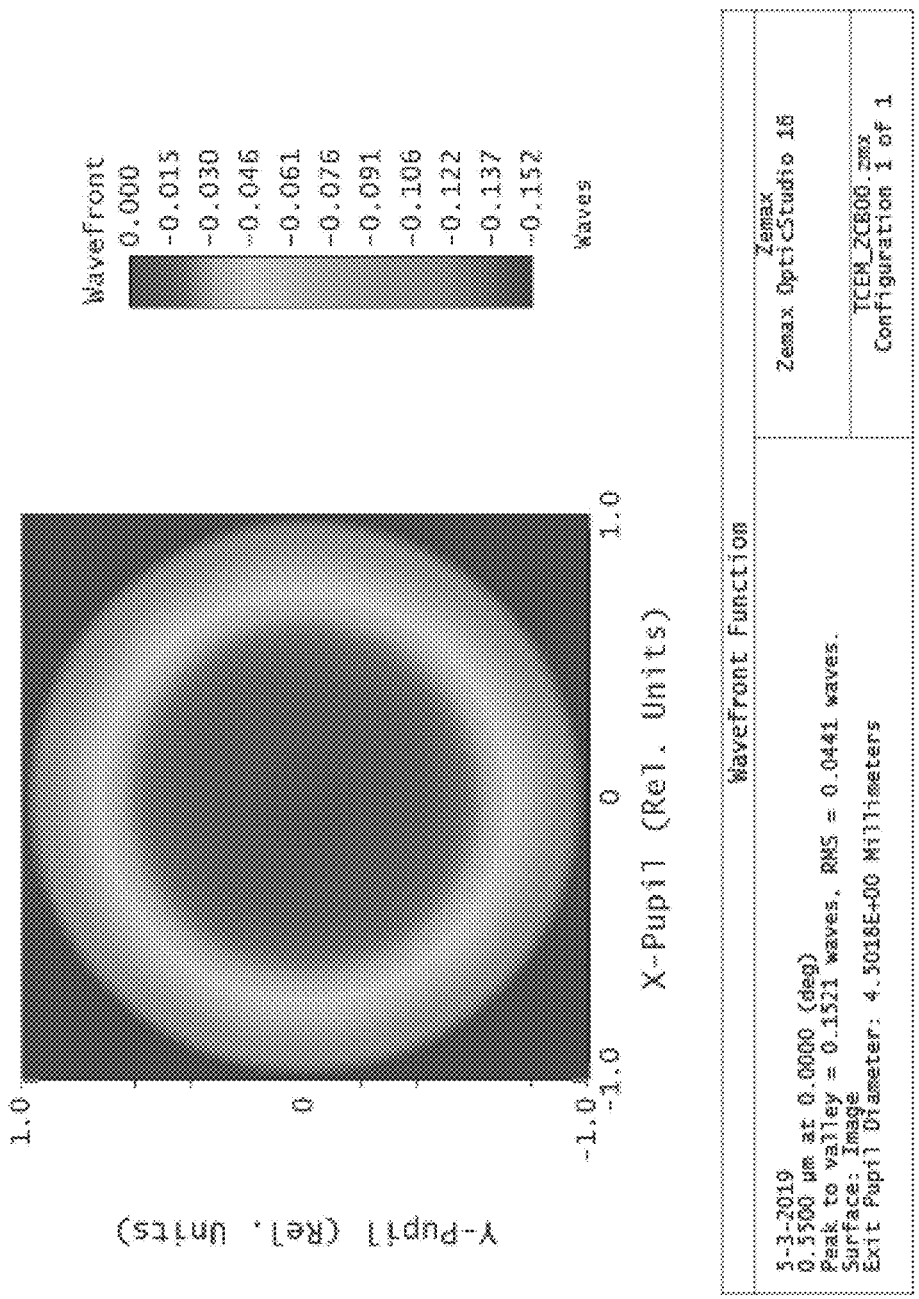
FIG. 6A illustrates a phase map (in waves of a 20 D monofocal IOL implanted in an average eye.
Figure 6B:
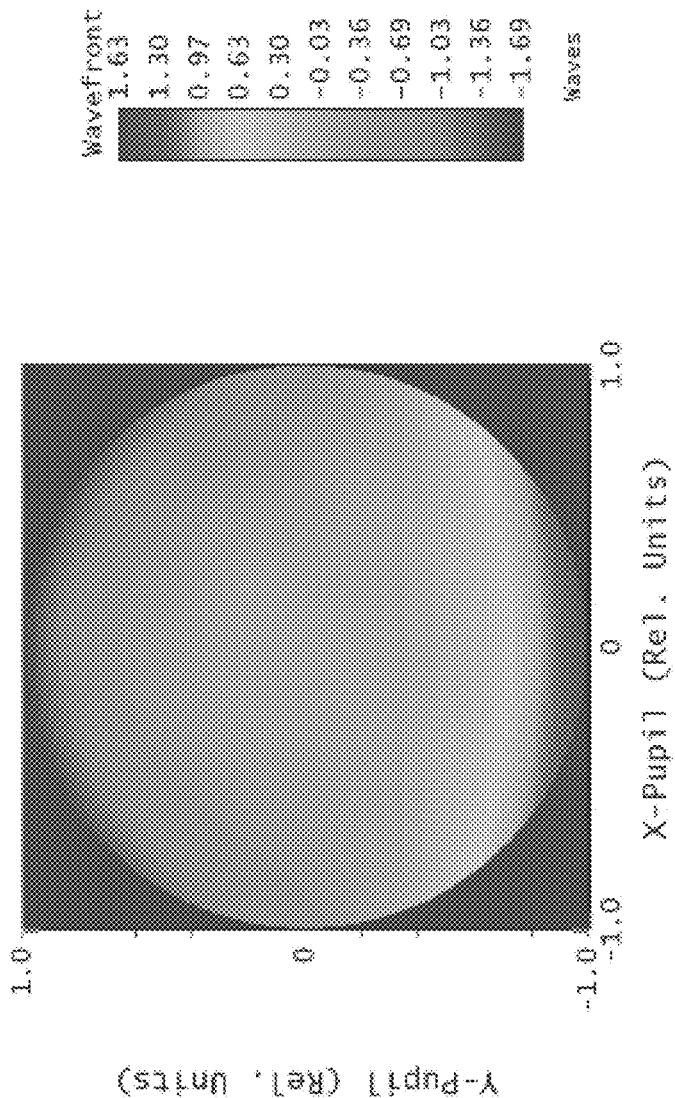
FIG. 6B illustrates the phase map (in waves) induced by 5 degrees tilt of a 20 D monofocal IOL.
Figure 6C:
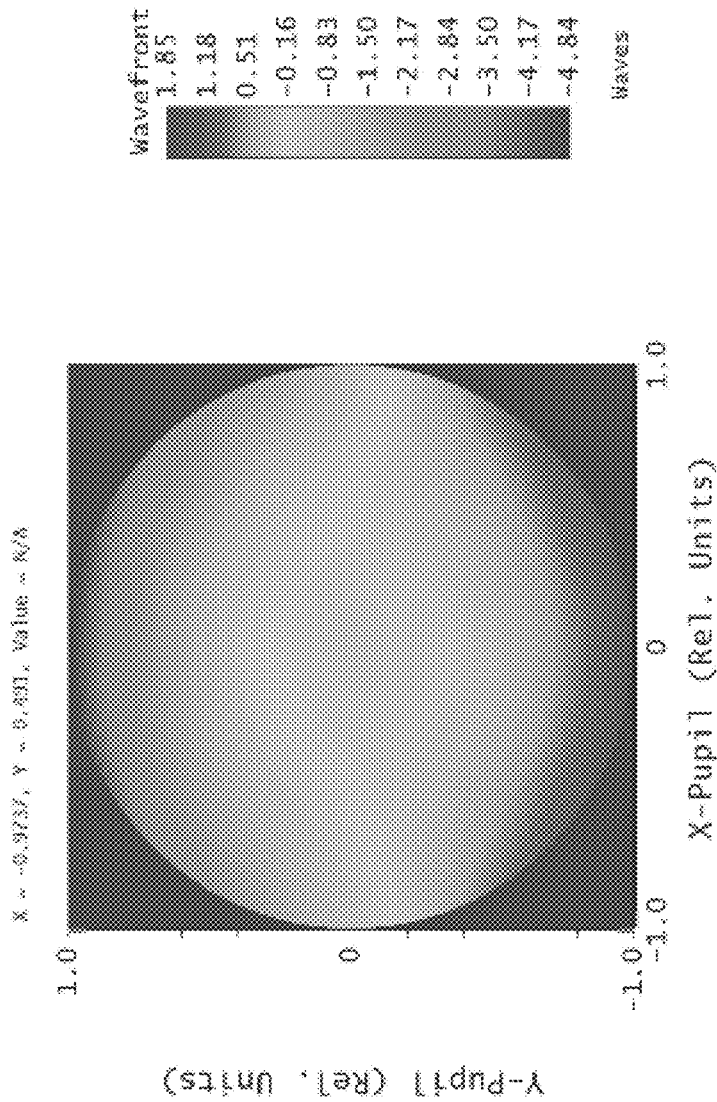
FIG. 6C illustrates the phase map (in waves) induced by 0.5 mm decentration of a 20 D monofocal IOL.
Figure 6C:
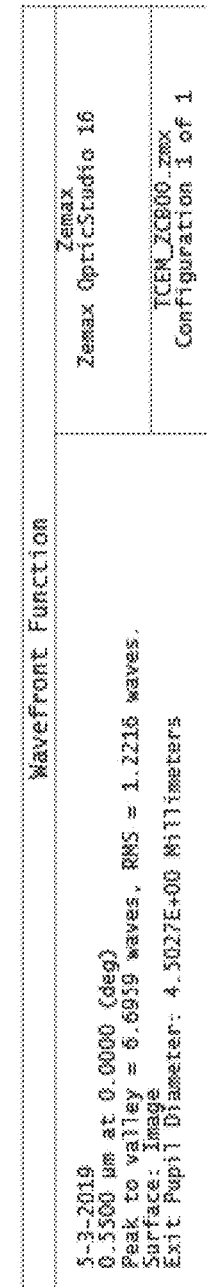

The eye is not a perfectly centered optical system. The apex of the cornea, center of the pupil, center of the IOL and fovea does not always fall along a straight line. Furthermore, even if there is such a line, the optical elements can be tilted with respect to that line. These deviations from un-tilted straight-line optics have many names, depending on which of these deviations is taken as a reference point (e.g., center of pupil, fovea, or corneal apex) which include angle kappa, angle alpha, angle lambda and angle gamma. When the cornea, pupil, IOL, and fovea, all of which can be decentered and two of which have an optical impact of tilt (cornea and IOL), a large number of deviations can exist, and therefore even perfect positioning and tilt of the IOL during surgery may not result in optimal vision. FIG. 5A is an illustration of an eye of a subject with a tilted IOL (note the alignment along the dashed line, which is tilted with respect to the optical axis OA, rather than the optical axis), and FIG. 5B is an illustration of an eye of a subject with the IOL decentered with respect to the optical axis OA (note the vertical displacement of the IOL above the optical axis OA, as further indicated by the dashed line). In each of FIGS. 5A and 5B, like elements of the eye and IOL shown in FIG. 1B share the same reference numerals. FIG. 6A illustrates a phase map (in waves) of a 20 D monofocal IOL implanted in an average eye. FIG. 6B illustrates the phase map (in waves) induced by 5 degrees tilt of a 20 D monofocal IOL. FIG. 6C illustrates the phase map (in waves) induced by 0.5 mm decentration of a 20 D monofocal IOL.

In accordance with some embodiments of the present disclosure, refractive index writing is used to optimize foveal vision by correcting for the effect of these deviations in position by inscribing phase pattern on the IOL that corrects and compensates for these errors. The position and tilt of each of the elements can be measured after surgery, and ray-tracing software can be used to calculate the optimal aberration pattern inscribed which corrects for these errors.

Tilt and decentration can be altered by phase changes from refractive index writing. These can be measured using, for example, Purkinje imaging technology. Subsequently, the impact of tilt and decentration on IOLs can be simulated using ray tracing software, and adequate phase map compensation then calculated accordingly. This can be done once for a wide range of IOL models, tilt, and decentration, to provide automatic suggestion of phase changes following a measured tilt and decentration. Examples of ray-tracing software are Zemax and Oslo. In them, eye models can be implemented (such as the Navarro eye model). Normally, lenses are well-centered, but if the IOL is simulated to be decentered according to measured values, and subsequently a phase map is imposed, the software can optimize which phase map provides the best vision by optimizing for providing, for example, the best modulation transfer function (MTF).

In one aspect, the present disclosure relates to a method for improving vision of a subject having an implanted intraocular lens (IOL). In one embodiment, the method can include determining a deviation in position of at least one optical element from a reference line corresponding to alignment of the apex of the cornea, center of the pupil, center of the IOL, and fovea, and/or determining a tilt of at least one of the optical elements relative to the reference line. The deviation(s) in position and the tilt produce an imperfection in foveal vision in the subject. The method can further include applying a plurality of focused laser pulses to a selected area of the implanted IOL, using laser pulses that are applied according to a predetermined pattern and that are configured to produce, through refractive index writing, a phase change pattern on the IOL that is configured to compensate for the deviation(s) and/or tilt to improve the foveal vision of the subject.

The phase change pattern to be produced by RIW can be calculated, prior to the application of the plurality of focused laser pulses, based on at least one of: biometrics including one or more of IOL positioning, axial length, corneal power, and refraction. The biometrics associated with the IOL positioning include measurements of at least one of effective lens position, tilt, and decentration of the IOL. The biometrics associated with the corneal power can include keratometry and/or elevation maps.

In some embodiments, determining the tilt and decentration can be performed using Purkinje imaging. In some embodiments, determining the tilt and decentration can performed using optical coherence tomography (OCT). In some embodiments, determining the phase change pattern can include ray-tracing simulation.

In some embodiments, the pattern according to which the pulses of radiation are applied can be calculated based at least in part on the at least one of the deviation in position and the tilt.

In another aspect, the present disclosure relates to a system for improving vision of a subject. In one embodiment, the system includes at least one sensor that is configured to sense a deviation in position of at least one optical element from a reference line corresponding to alignment of the apex of the cornea, center of the pupil, center of the IOL, and fovea and/or a tilt of at least one optical element relative to the reference line. The deviation in position and/or the tilt produces an imperfection in foveal vision in the subject. The system also includes a control system operatively coupled to the at least one sensor and configured to receive associated sensed data corresponding to the deviation in position and/or the tilt. The control system is also configured to calculate, based at least on the sensed data, a phase change pattern to produce on the IOL, that is configured to compensate for the deviation and/or tilt to improve the foveal vision of the subject. The control system is also configured to calculate a pattern of a plurality of pulses of radiation to apply to the IOL to produce the phase change pattern and/or calculate one or more selected areas of the IOL to which the plurality of pulses are to be applied. The system also includes a pulsed radiation system operatively coupled to the control system. The pulsed radiation system can be configured to, based on control by the control system, apply the plurality of pulses of radiation to the IOL according to the pattern to produce, by refractive index writing on the IOL, the phase change pattern on the IOL that is configured to compensate for the deviation and/or tilt to improve the foveal vision of the subject. The at least one sensor can be configured to sense the deviation and tilt and the control system may be configured to receive data corresponding to both the deviation and the tilt.

In some embodiments, the pulsed radiation system includes a pulsed laser and is configured to apply a plurality of laser pulses to the one or more selected areas of the IOL, according to the pattern of the plurality of pulses, to produce the phase change pattern. In some embodiments, the control system can be configured to determine the phase change pattern based at least in part on biometrics associated with at least one of: IOL positioning; axial length; corneal power; and refraction. In some embodiments, the biometrics associated with IOL positioning include measurements of at least one of effective lens position, tilt, and decentration of the IOL. In some embodiments, the biometrics associated with the corneal power include at least one of keratometry and elevation maps.

In some embodiments, the system can be configured to determine the tilt and/or decentration using Purkinje imaging. In some embodiments, the system also includes an optical coherence tomography (OCT) system configured to determine the tilt and/or decentration. In some embodiments, the system is configured to determine the phase change pattern using, at least in part, ray-tracing simulation. In some embodiments, the control system can be configured to calculate the pattern according to which the pulses of radiation are applied based at least in part on the deviation in position and/or the tilt.

Phase Wrapping

Phase wrapping relates to, in the implementation of refractive index writing, that the maximum achievable optical path difference can be limited. For example, a refractive index writing system may not be able to easily shift the phase, e.g., 1.5 wavelengths, 2 wavelengths, or 3 wavelengths, at various locations in an intraocular lens (IOL), as there is a maximum possible shift in the absolute value of the refractive index over a volume. In some cases, the upper limit can be 1 wavelength, which may cause a challenge in implementing various phase maps. Phase wrapping in accordance with some embodiments of the present disclosure can overcome such challenges.

The starting point of a desired refractive index implementation, including those described above in accordance with certain embodiments of the present disclosure, is a phase map that has been shown to, e.g., shift power, reduce residual astigmatism, improve near vision, improve spectacle independence or reduce visual symptoms. Such phase maps often contain values higher than one wavelength. In these implementations, such higher values can be modulated by subtracting the necessary number of whole wavelengths in the phase step such that the complete phase map has values in the range of zero to one wavelength.

Figure 7:
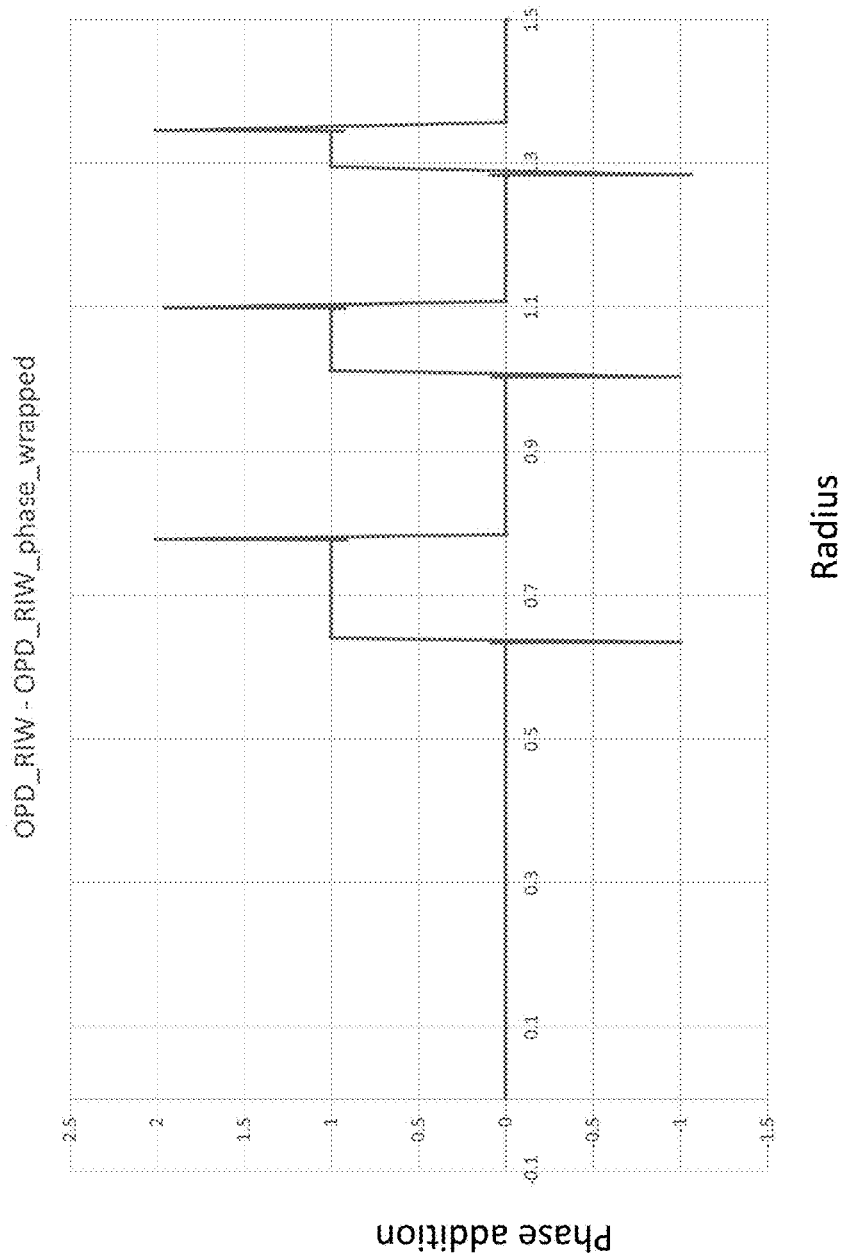
FIG. 7 plots the residual of a conventional phase profile with step size lager than a wavelength and its corresponding wrapped profile, in accordance with some embodiments of the present disclosure.

An example of the consequence of this implementation can be seen in FIG. 7. FIG. 7 plots the optical path difference of an implemented refractive index design with certain parts of the phase map having a phase addition higher than one wavelength. For the parts of the design that have a phase addition lower than one wavelength, no difference is seen. For the parts of the original design with a phase map value higher than one wavelength, however, a difference of exactly one wavelength (e.g. at 0.7 mm radius, at 1 mm radius, and at 1.3 mm radius) can be seen. Furthermore, the optical path difference impact of the transition between different zones can be seen. It should be understood that this example is purely for illustrative purposes, and any number of zones, and whole number of wavelengths can be phase wrapped.

Figure 8A:
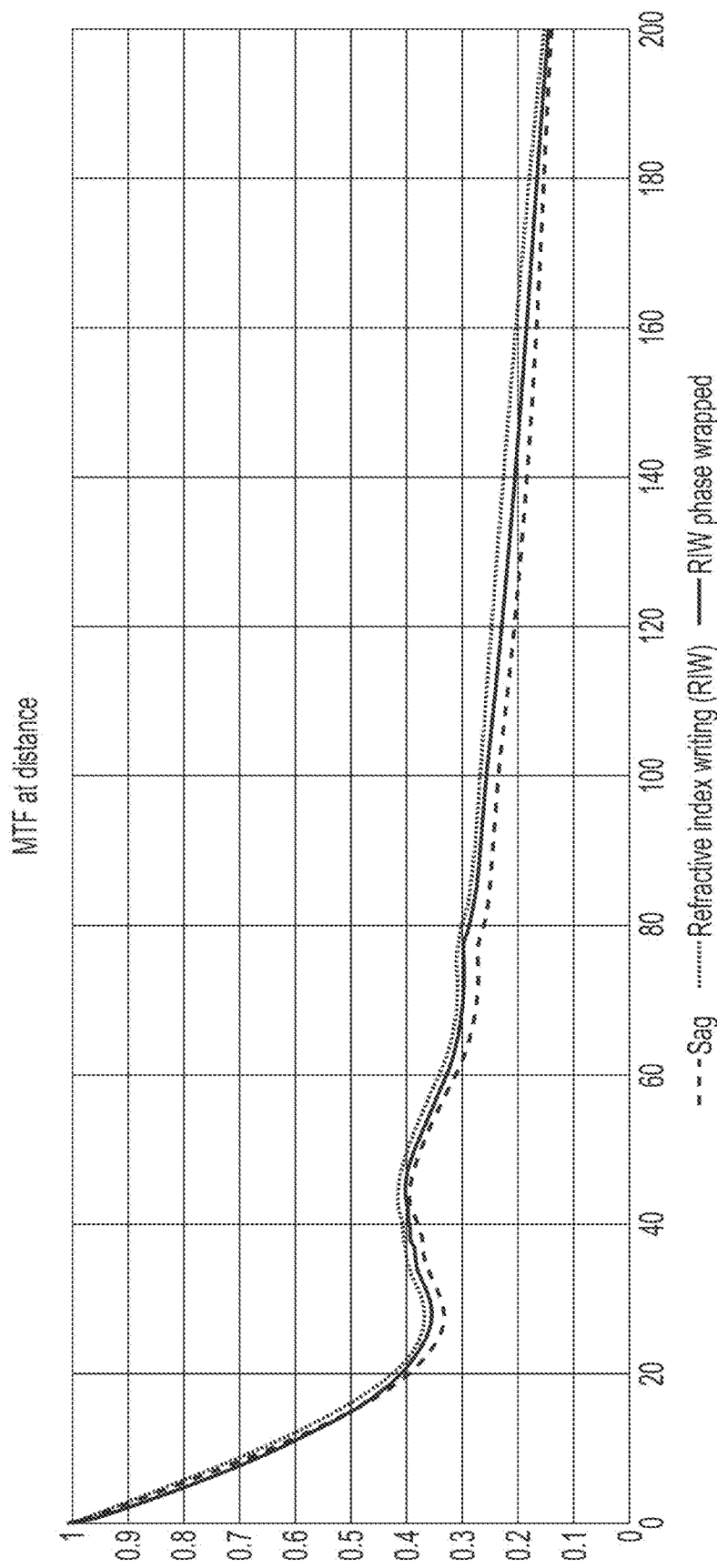
FIGS. 8A-8C illustrate various aspects of phase wrapping in accordance with some embodiments of the present disclosure.
Figure 8B:
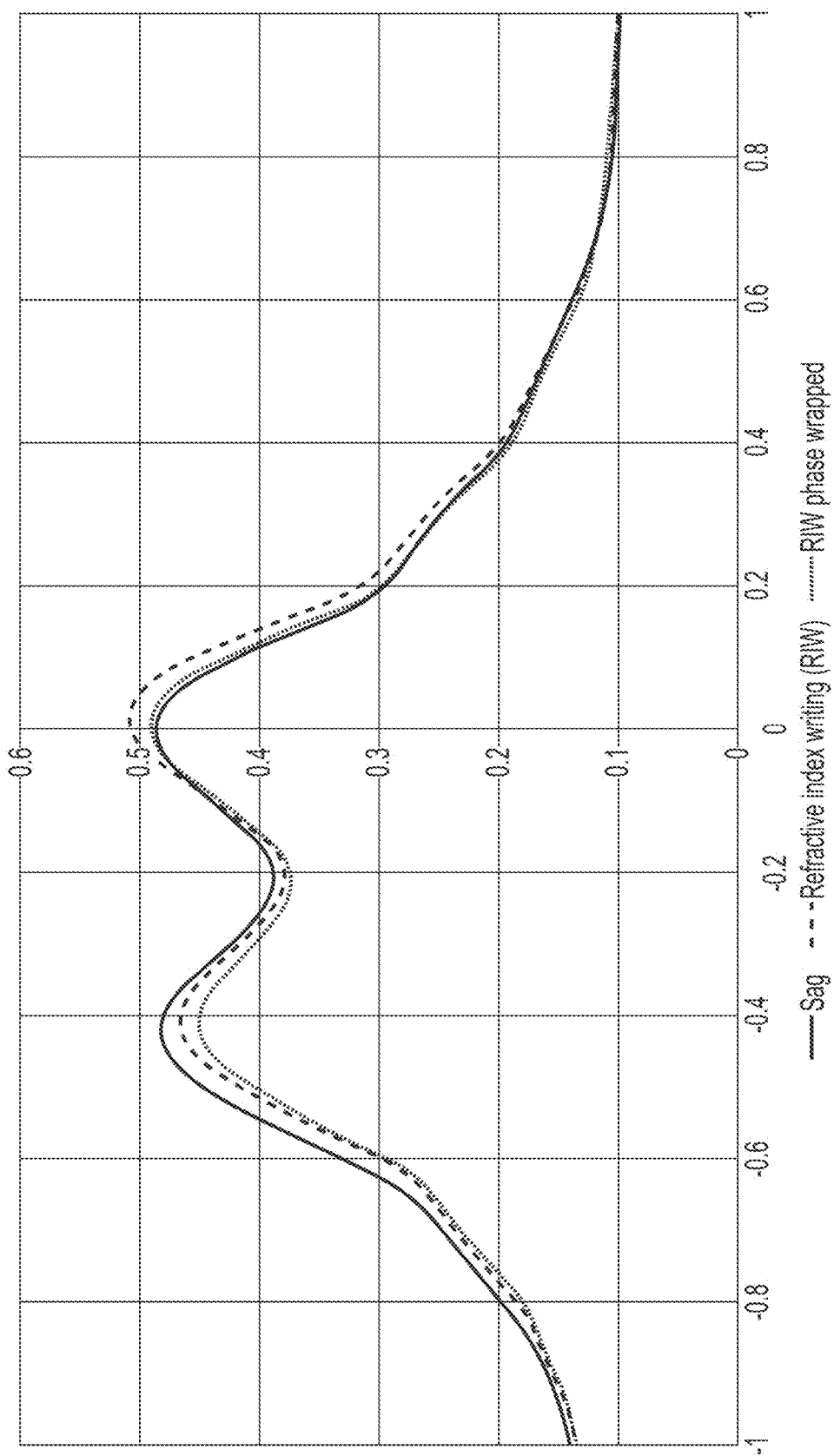
Figure 8C:
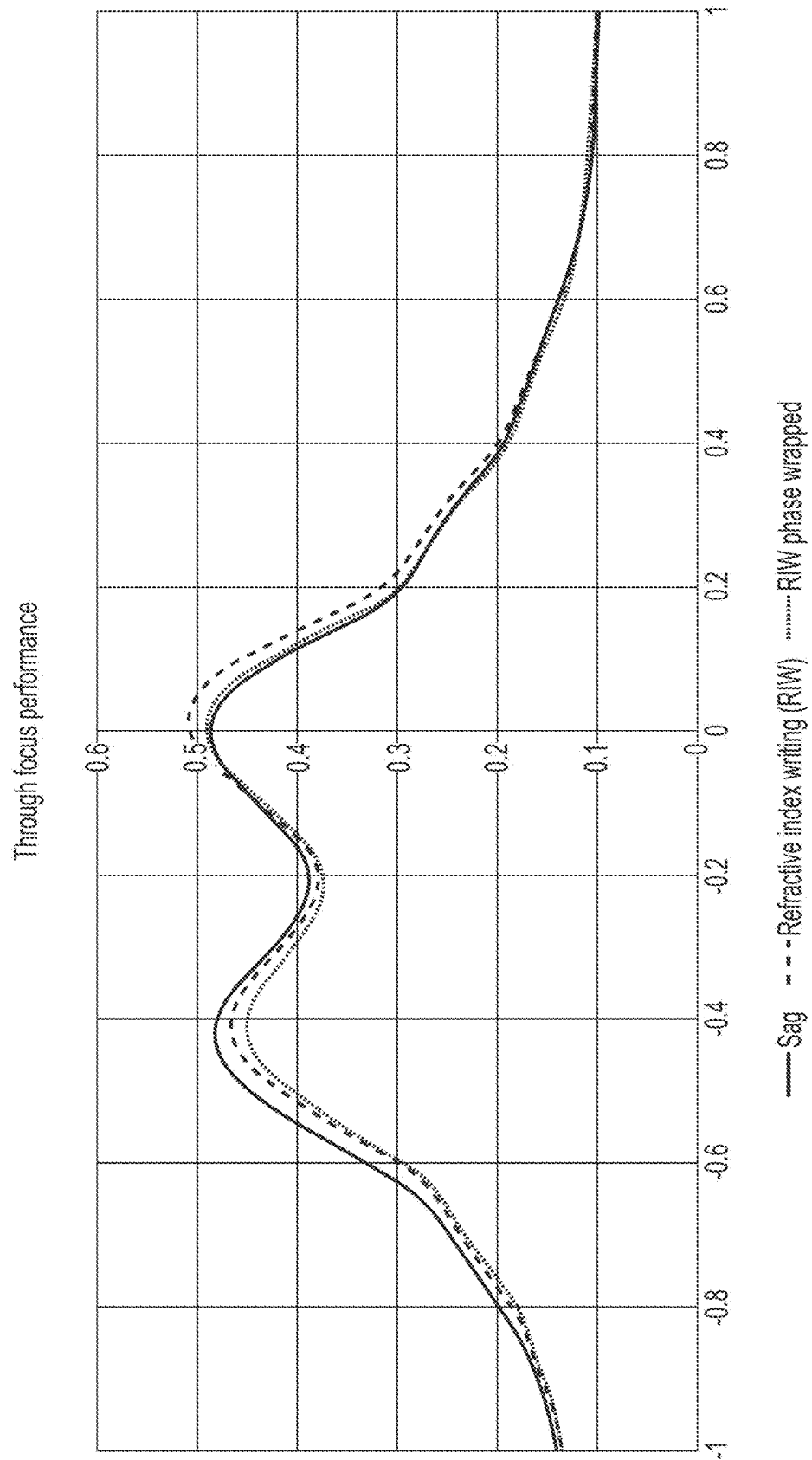

Benefits of the use of phase wrapping in accordance with some embodiments can be seen in the comparison of the illustrations of FIGS. 8A-8C. In each of FIGS. 8A-8C, three cases are compared: the design implemented using a sag profile (standard IOL technology), design using refractive index writing without the one wavelength limitation, and refractive index writing using phase wrapping. As is evident from the illustrations, phase wrapping successfully replicates the performance both of the sag profile and of the full refractive index writing profile.

Consistent with one or more aspects described above, and in accordance with some embodiments of the present disclosure, a method for phase wrapping in refractive index writing of an intraocular lens (IOL) implanted in a subject includes: for at least one area of the IOL wherein there is a maximum possible shift in the absolute value of the refractive index over a particular volume, modulating the values of a corresponding phase map such that the phase map has values in a particular desired wavelength range. In some embodiments, the desired wavelength range is from about 0 to about 1 wavelength for a maximum possible shift in the absolute value of above 1 wavelength of the refractive index over the particular volume.

Vergence Matching

In refractive index writing, in some implementations phase maps may not be implemented in narrow layers, but rather wide layers of, e.g., 50 µm, 100 µm, 200 µm, or 300 µm. This is wider than for sag profiles. As a result, light that is incident at a vergence, which is the case in the eye, risks transitioning from one zone to the other. For example, at one zone the desired phase addition can be 1.5 wavelength, and close by the desired phase addition can be 0 wavelengths. However, due to the vergence of the light, if the zone has a width of 300 µm, during the first 150 µm the light can pass the zone of 0 wavelengths phase addition, and during the last 150 µm the light can pass the zone of 1.5 wavelengths phase addition, with the result that the light has a phase addition of 0.75 wavelengths. This can result in undesirable outcomes for the subject.

To address the above-mentioned concerns, in some embodiments of the present disclosure a vergence matching is implemented in the refractive index writing. A vergence matching starts with a desired phase map, and initial depth position in the IOL, as well as the distance between the IOL and the retina. In some embodiments, the following steps are then performed: 1. creating a transformation function based on the vergence of the incident light; and 2. creating an angulated phase addition.

In accordance with some embodiments, creating a transformation function based on the vergence of the incident light includes mapping, as a function of radius in the IOL, the shift in z direction necessary to match the spherical form of the idealized wave when inside the IOL. This can be calculated by: a) taking an object at infinity, b) imaging through the subject's individual cornea, c) propagating to the anterior surface of the desired IOL using the measured anterior chamber depth (ACD) of the subject, d) imaging through the anterior surface of the IOL, and e) propagating to the plane of the desired refractive index writing. The wave will have a vergence, and this vergence is matched with the baseline surface of where the zero-level of the refractive index pattern is written.

In other embodiments, an average eye model (average cornea and/or average ACD) can be used to calculate the vergence. In other embodiments, a combination of measured and average data can be used to calculate vergence. Additionally, vergence matching can account for both rotationally and non-rotationally optical effects, by creating a 2D function, where vergence is determined by meridian.

Figure 9A:
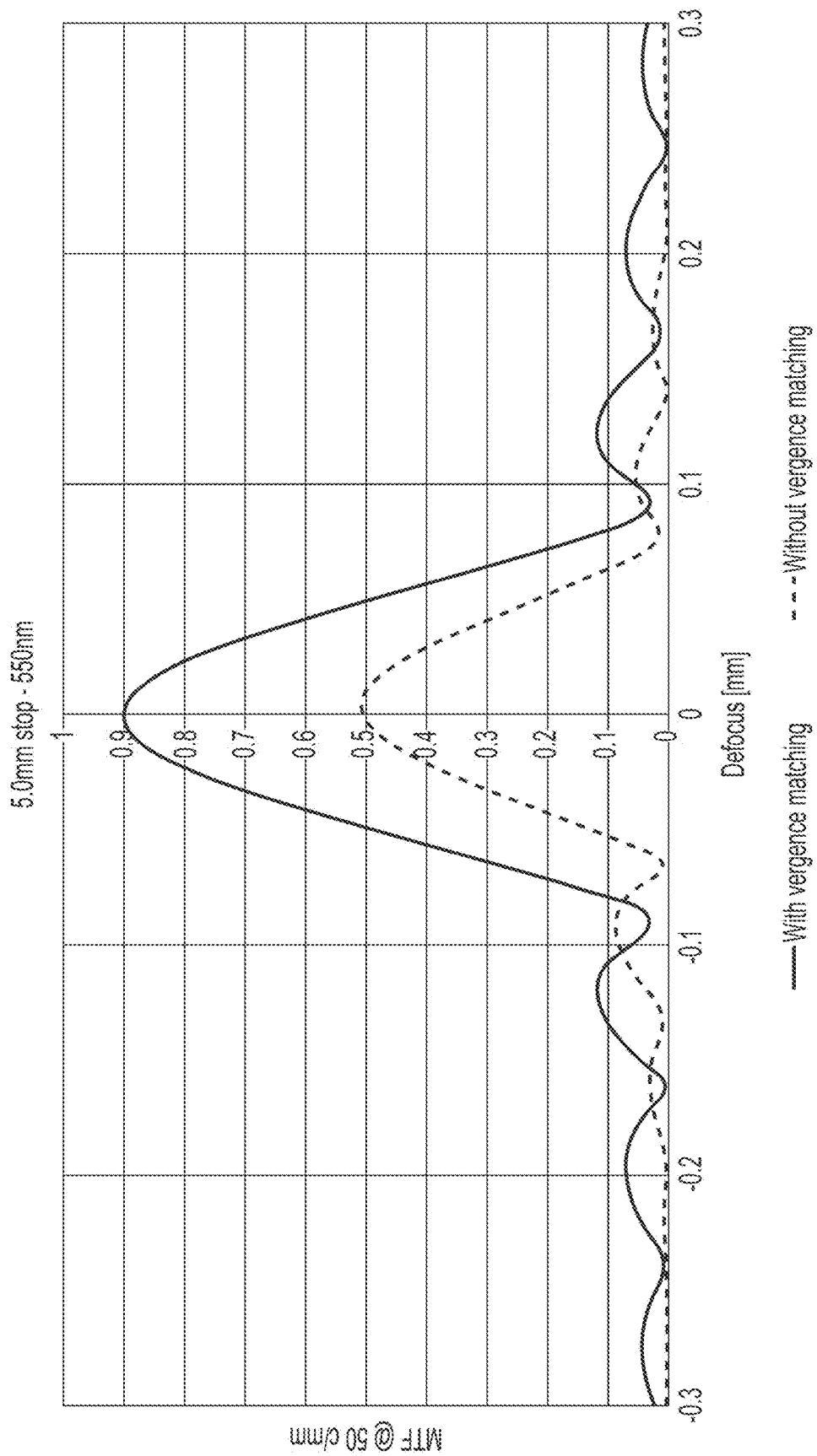
FIGS. 9A and 9B illustrate aspects of vergence matching in accordance with some embodiments of the present disclosure.
Figure 9B:
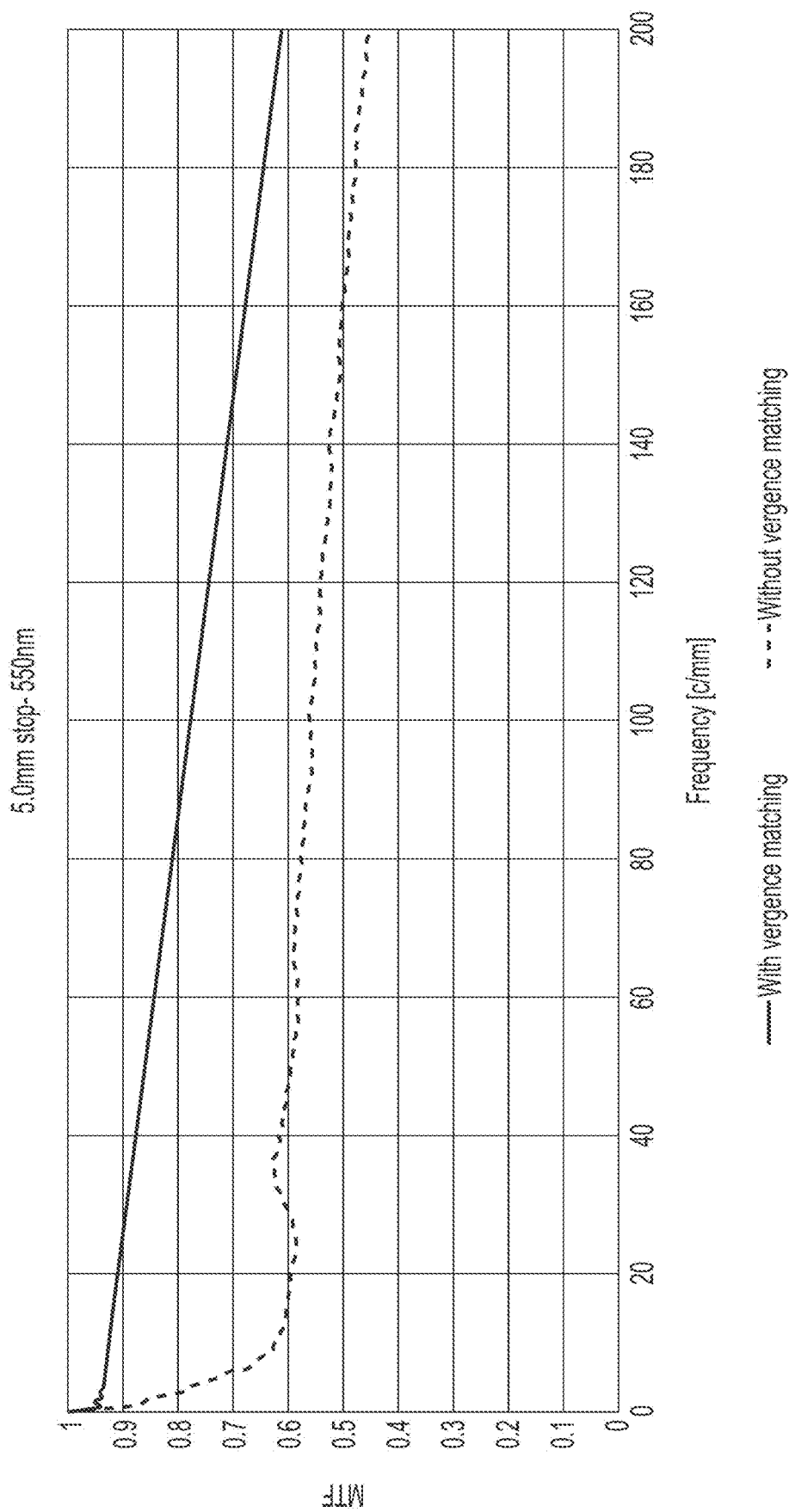

With regard to the above-mentioned step "2." of creating an angulated phase addition, while the phase pattern can be written perpendicular to the apex of the IOL, in accordance with some embodiments of the present disclosure at each point in this new surface described at point 1, the phase map is instead written with a depth of, e.g., 50 µm, 100 µm, 200 µm, or 300 µm perpendicular to the vergence calculated above. The advantages of vergence matching according to some embodiments of the present disclosure can be seen in the comparison of simulations shown in FIGS. 9A and 9B, illustrating simulations with and without vergence matching, utilizing refractive index written designs.

Consistent with one or more aspects described above, and in accordance with some embodiments of the present disclosure, a method for vergence matching in refractive index writing includes determining a desired phase map for producing, by refractive index writing, a phase change on an IOL, which can be an IOL implanted in the eye of a subject; determining the vergence of the wave after refraction on the anterior surface of the IOL for the design wavelength; propagating this wavefront to the plane of the refractive index writing within the IOL, and estimating the curvature in that plane. Based on this result, a desired phase map can be converted into a vergence-matched three-dimensional (3D) phase map such that the original flat phase map follows the curved vergence of the wavefront. Estimating the curvature in the plane of the refractive index writing can include calculating the curvature using ray tracing software (e.g., Zemax, Code V, Oslo), or other geometrical optics calculations (e.g., relating to wave propagation), some aspects of which will be described below.

Propagation of the wavefront can be calculated by: taking an object at infinity; imaging through the individual cornea of the subject; propagating to the anterior surface of the IOL based on a measured distance between the cornea of the subject and the anterior surface of the IOL, the shape of the anterior surface of the IOL, and the refractive index of the IOL; imaging through the anterior surface of the IOL; and propagating to the plane inside the IOL to an area where the refractive index writing is to be performed. In some embodiments, the method includes matching the vergence with a baseline surface where the zero-level of the refractive index pattern is written. The vergence can be calculated using a model of an average cornea and/or average ACD. The vergence can be calculated using a model of an average IOL design for a particular power. The shape of the anterior surface of the IOL can be estimated using optical coherence tomography (OCT) imaging.

In some embodiments, vergence matching accounts for rotational and non-rotational optical effects by creating a two-dimensional function, wherein vergence is determined by meridian. In some embodiments, the method also includes creating an angulated phase addition, wherein at each point on a target surface of the IOL, a phase addition is written, by the refractive index writing, with a depth perpendicular to the calculated vergence. The phase addition can have a predetermined depth perpendicular to the calculated vergence. The refractive index writing can include applying a plurality of focused laser pulses to a selected area of the IOL.

In another aspect, the present disclosure relates to a system for improving vision of a subject. In one embodiment, a pulsed radiation system can be configured to apply, by refractive index writing, a plurality of pulses of radiation to at least one selected area of an intraocular lens (IOL) implanted in an eye of a subject, according to a predetermined pattern. The system can also include a control system coupled to the pulsed radiation system and configured to control the pulsed radiation system and to perform functions that include: determining a desired phase map for producing, by refractive index writing, a phase change in an IOL implanted in an eye of a subject, the IOL having an anterior surface and a posterior surface; calculating vergence of a wave after refraction on the anterior surface of the IOL for a desired wavelength design; calculating propagation of a corresponding wavefront to the plane of the refractive index writing within the IOL; estimating curvature of the wavefront in the plane of the refractive index writing; and, based on the estimated curvature, converting an initial phase map into a vergence-matched three-dimensional (3D) phase map, such that the initial phase map follows the curved vergence of the wavefront; and In some embodiments, propagation of the wavefront can be calculated by performing functions that include: taking an object at infinity; imaging through the individual cornea of the patient; propagating the wavefront to the anterior surface of the IOL based on a measured distance between the cornea of the patient and the anterior surface of the IOL, the shape of the anterior surface of the IOL, and the refractive index of the IOL; imaging through the anterior surface of the IOL; and propagating the wavefront to the plane inside the IOL to an area where the refractive index writing is to be performed. The vergence can be matched with a baseline surface wherein the zero-level of the refractive index pattern is written.

In some embodiments, a model of an average cornea and/or average anterior chamber depth (ACD) is used to calculate the vergence. In some embodiments, a model of an average IOL design for a particular power is used to calculate the vergence. In some embodiments, the shape of the anterior surface of the IOL can be estimated using optical coherence tomography (OCT) imaging In some embodiments, the vergence matching accounts for rotational and non-rotational optical effects by creating a two-dimensional function, wherein vergence is determined by meridian.

In some embodiments, the control system can be configured to control the pulsed radiation system to create an angulated phase addition, wherein at each point on a target surface of the IOL, a phase addition is written, by the refractive index writing, with a depth perpendicular to the calculated vergence. In some embodiments, the phase addition has a predetermined depth perpendicular to the calculated vergence.

Vergence Matching of a Refractive Index Writing Design

Figure 10A:
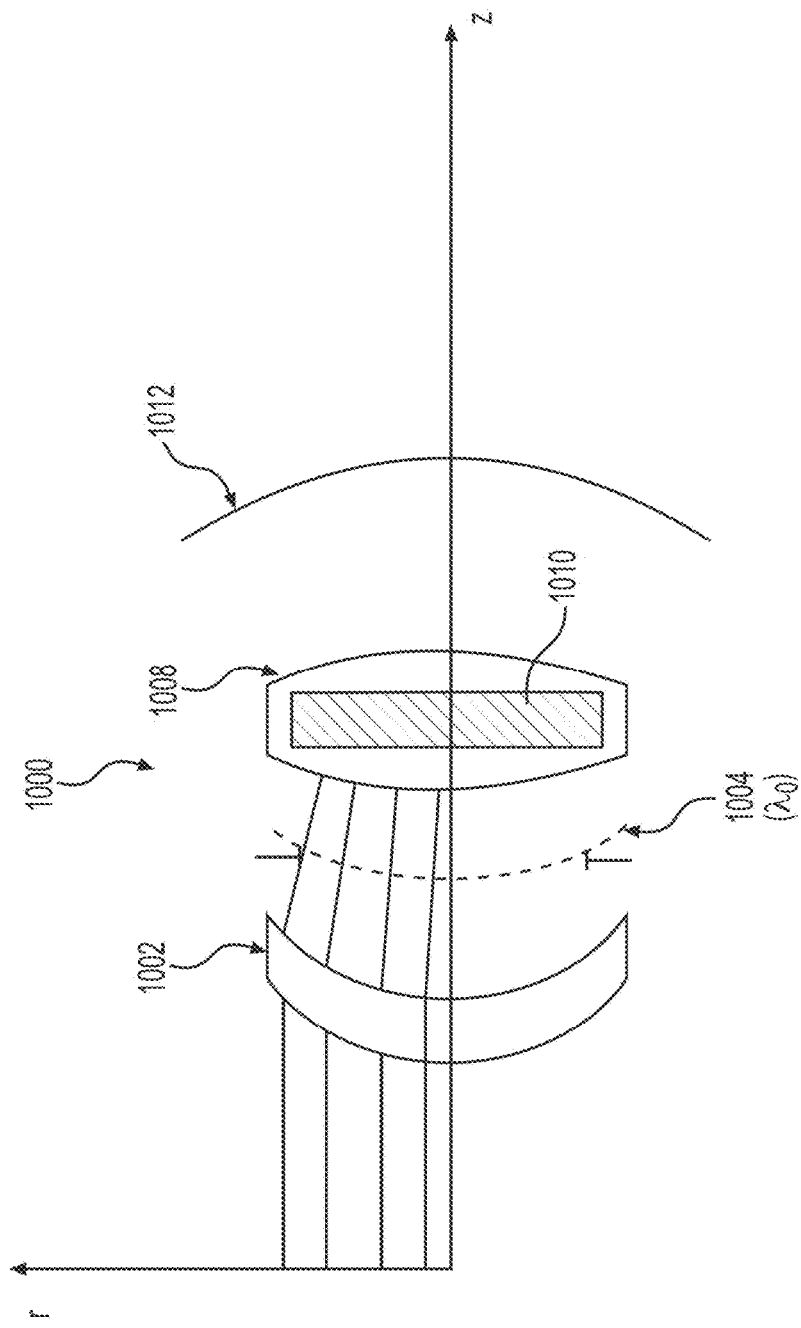
FIGS. 10A-10C illustrate aspects of vergence matching with refractive index writing designs, in accordance with embodiments of the present disclosure.
Figure 10B:
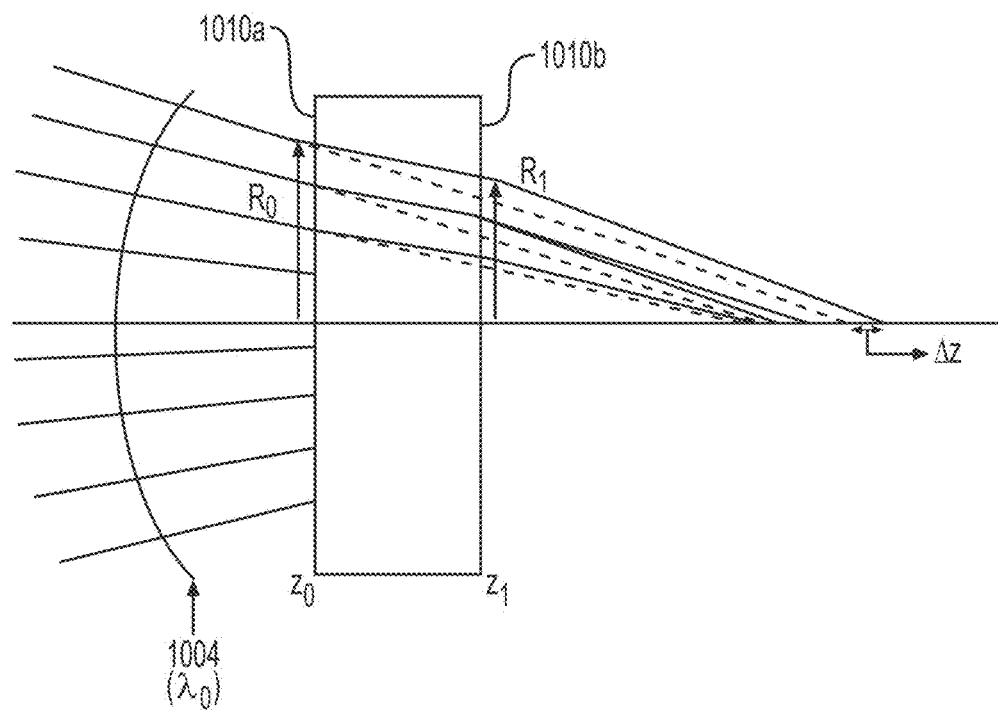
Figure 10C:
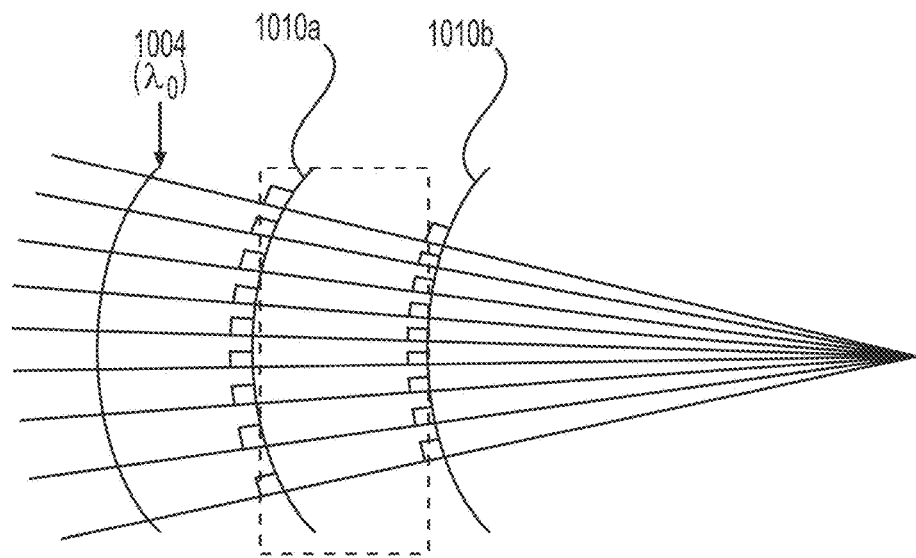

FIGS. 10A-C illustrate aspects of vergence matching of a refractive index writing design, in accordance with embodiments of the present disclosure. FIG. 10A shows a schematic of the pseudo-phakic eye (see, e.g. cornea 1002 and retina 1012) with rays entering the eye with zero vergence, as well as an intraocular lens (IOL) 1008 comprising an optical profile 1010 induced by refractive index writing, collectively 1000. FIGS. 10B and 10C show a zoomed in view of the optical profile 1010. In accordance with some embodiments of the present disclosure, to design a lens that considers the vergence of the wavefront 1004 ($\lambda_0$), for the design wavelength, the direction ($\tan(\theta)$) of each ray is measured at a given radial coordinate. FIGS. 10B and 10C show also that the direction of the ray increases with the radial coordinates. In accordance with some embodiments, knowing the ray direction versus ray height and the value of the refractive index (RI) at RI ($z_0$, $R_0$) (see FIG. 10B)), the refractive index is redesigned inside such that the RI at ($z_1$, $R_1$) is equal to the RI at ($z_0$, $R_0$) (see FIG. 10B). Accordingly, the z-dependence is achieved by making the RI at ($z_0$, $R_0$) equal to the RI at ($z_1$, $R_1$); this thereby "shrinks" or reduces the volume where the refractive index has been written. To keep the rays shown in FIG. 10B from deviating or changing direction, the optical profile 1010 is bent (see FIG. 10C, bent with reference to the initial orientation indicated by the dashed box) such that these rays have a zero incidence.

Further stated, FIG. 10B shows that the output rays after the optical profile 1010 with vergence matching are parallel to the ray before entering the optical profile 1010 with an offset. This can cause an unwanted spherical aberration, longer optical path length than intended, and/or un-intended power shift, among other undesired effects. To cancel these undesirable effects, in accordance with some embodiments, the surfaces (anterior 1010a and posterior 1010) of the optical profile 1010 are bent such that the rays at the interface between the IOL 1008 and optical profile 1010 have a zero incidence, i.e., the rays are normal to the surface of the optical profile 1010 (see FIG. 10C). Therefore, the rays do not change their direction inside and outside the optical profile 1010 and add the intended optical path length.

Consistent with aspects described above, and in accordance with some embodiments of the present disclosure, a method of vergence matching for an intraocular lens (IOL) having an optical profile induced by refractive index writing can include the steps of: determining the direction of a plurality of rays associated with a vergence of a wavefront; determining the ray direction and ray height of a plurality of rays entering a first location of the optical profile; and determining the refractive index of the optical profile at the first location. The method can also include, based on the determined ray direction, ray height, and refractive index at the first location, and by refractive index writing, specifying the volume and shape of each voxel to match the wavefront through the direction of propagation. The method can also include bending anterior and posterior surfaces of the optical profile such that rays inside a portion of the IOL changed by refractive index writing and outside a portion of the IOL changed by refractive index writing do not change direction; and determining a second location that, for each of the rays, corresponds to the location where the respective ray exits the optical profile changed by refractive index writing.

In some embodiments, the volume and shape of each voxel match the wavefront through the direction of propagation such that the voxels decrease for converging wavefronts. In some embodiments, the volume and shape of each voxel match the wavefront through the direction of propagation such that the voxels increase for diverging wavefronts.

In some embodiments, the anterior and posterior surfaces of the optical profile are bent such that rays at the interface of the respective surfaces of the optical profile with other portions of the lens have a zero incidence. The first location can correspond to a first plane parallel to a vertical axis of the lens and the second location can correspond to a second plane parallel to the first plane. The first location can be proximate to or correspond to the anterior surface of the lens and the second location can be proximate to or correspond to the posterior surface of the lens. In some embodiments, the bent anterior and posterior surfaces are bent to define a non-zero curvature about the optical axis. In some embodiments, the refractive index writing includes applying a plurality of pulses of radiation according to a predetermined pattern. The plurality of pulses of radiation can be focused laser pulses applied according to the predetermined pattern. In some embodiments, the IOL is implanted in an eye of a subject.

In another aspect, in some embodiments a system for improving vision of a subject can include a pulsed laser system configured to apply a plurality of laser pulses to an intraocular lens (IOL) implanted in an eye of a subject and to change the refractive index of at least one selected area of the IOL by refractive index writing, wherein the IOL has an optical profile induced by refractive index writing. The system can also include a control system coupled to the pulsed laser system and configured to control the pulsed laser system to apply the plurality of laser pulses according to calculated pattern. The control system can also be configured to perform functions that include determining the direction of a plurality of rays associated with a vergence of a wavefront; determining the ray direction and ray height of a plurality of rays entering a first location of the optical profile; determining the refractive index of the optical profile at the first location; and, based on the determined ray direction, ray height, and refractive index at the first location, and by refractive index writing using the pulsed laser system, specifying the volume and shape of each voxel to match the wavefront through the direction of propagation.

In some embodiments, the control system can also be configured to calculate the pattern of laser pulses to apply. In some embodiments, anterior and posterior surfaces of the optical profile are bent such that rays inside a portion of the IOL changed by refractive index writing and outside a portion of the IOL changed by refractive index writing do not change direction. In some embodiments, the control system can be further configured to determine a second location that, for each of the rays, corresponds to the location where the respective ray exits the optical profile changed by refractive index writing. In some embodiments, the volume and shape of each voxel match the wavefront through the direction of propagation such that the voxels decrease for converging wavefronts. In some embodiments, the volume and shape of each voxel match the wavefront through the direction of propagation such that the voxels increase for diverging wavefronts.

In some embodiments, the anterior and posterior surfaces of the optical profile are bent such that rays at the interface of the respective surfaces of the optical profile with other portions of the lens have a zero incidence. In some embodiments, the anterior and posterior surfaces are bent to define a non-zero curvature about the optical axis.

In some embodiments, the first location can correspond to a first plane parallel to a vertical axis of the lens and the second location corresponds to a second plane parallel to the first plane. In some embodiments, the first location can be proximate to or corresponds to the anterior surface of the lens, and the second location can be proximate to or corresponds to the posterior surface of the lens.

Figure 11:
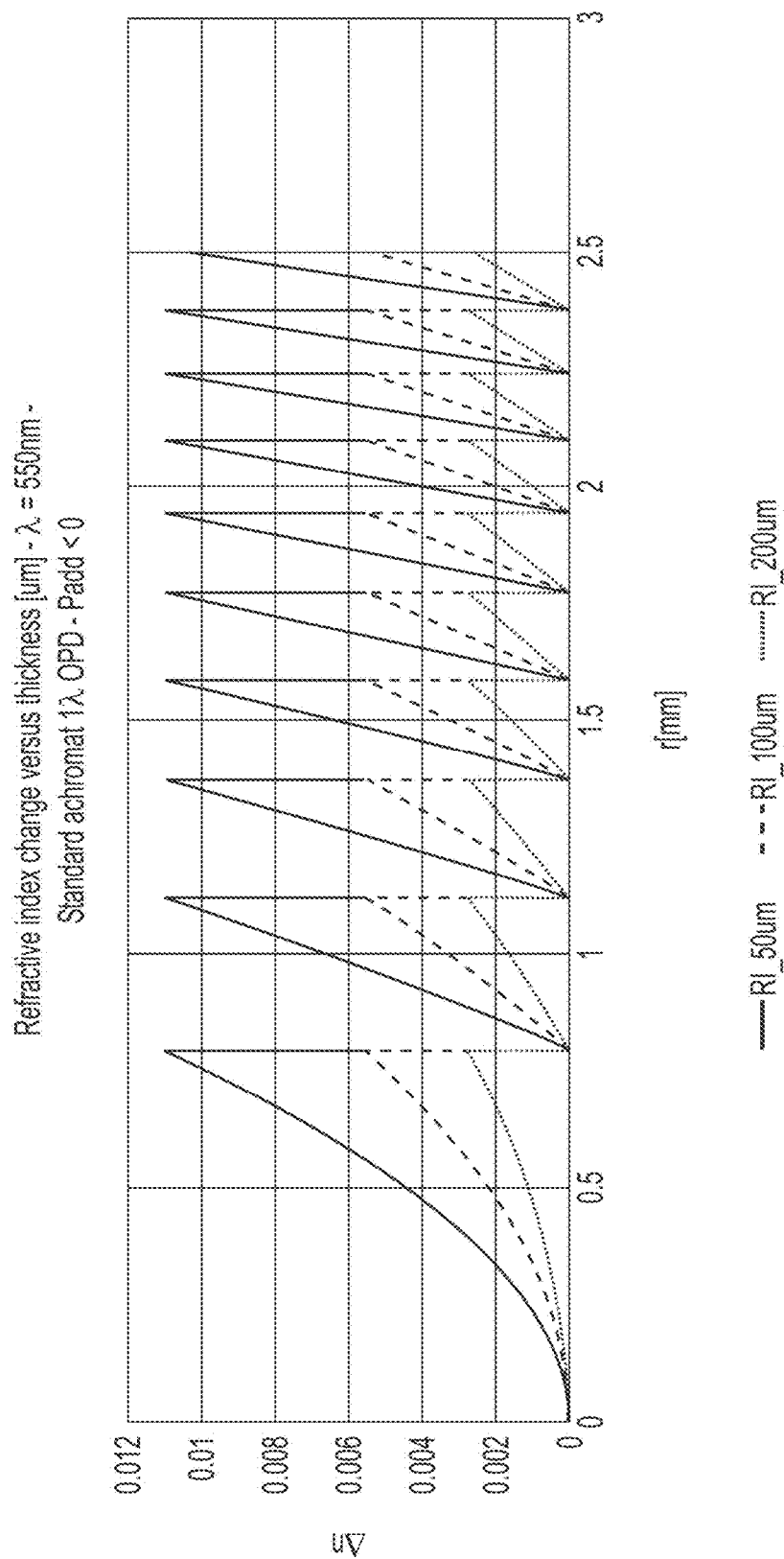
FIGS. 11 and 12 illustrate the radial dependence of the refractive index change for different thicknesses of the optical profile written inside the IOL, for power subtraction (FIG. 11) and power addition (FIG. 12), in accordance with embodiments of the present disclosure.
Figure 12:
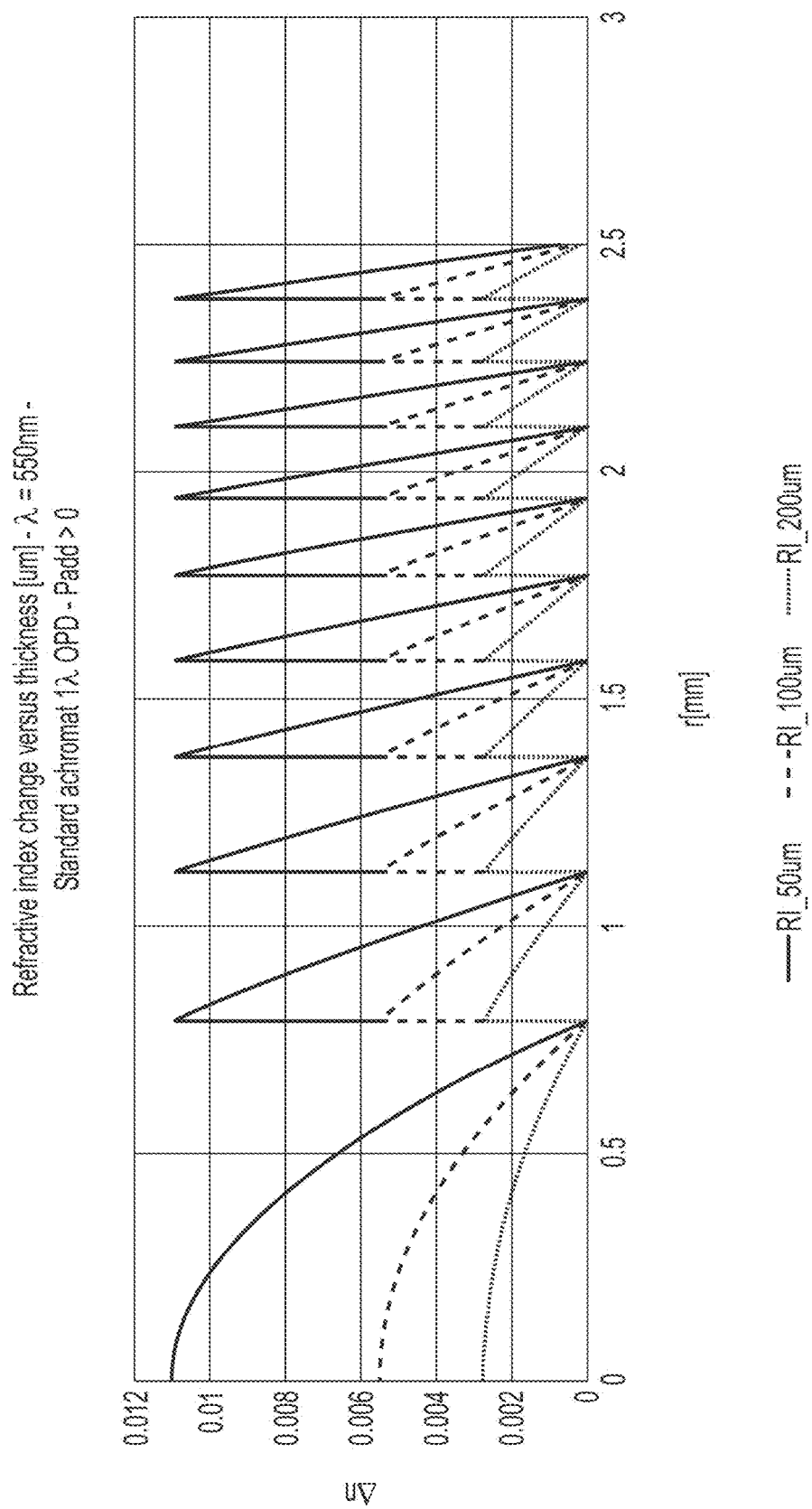
Figure 13:
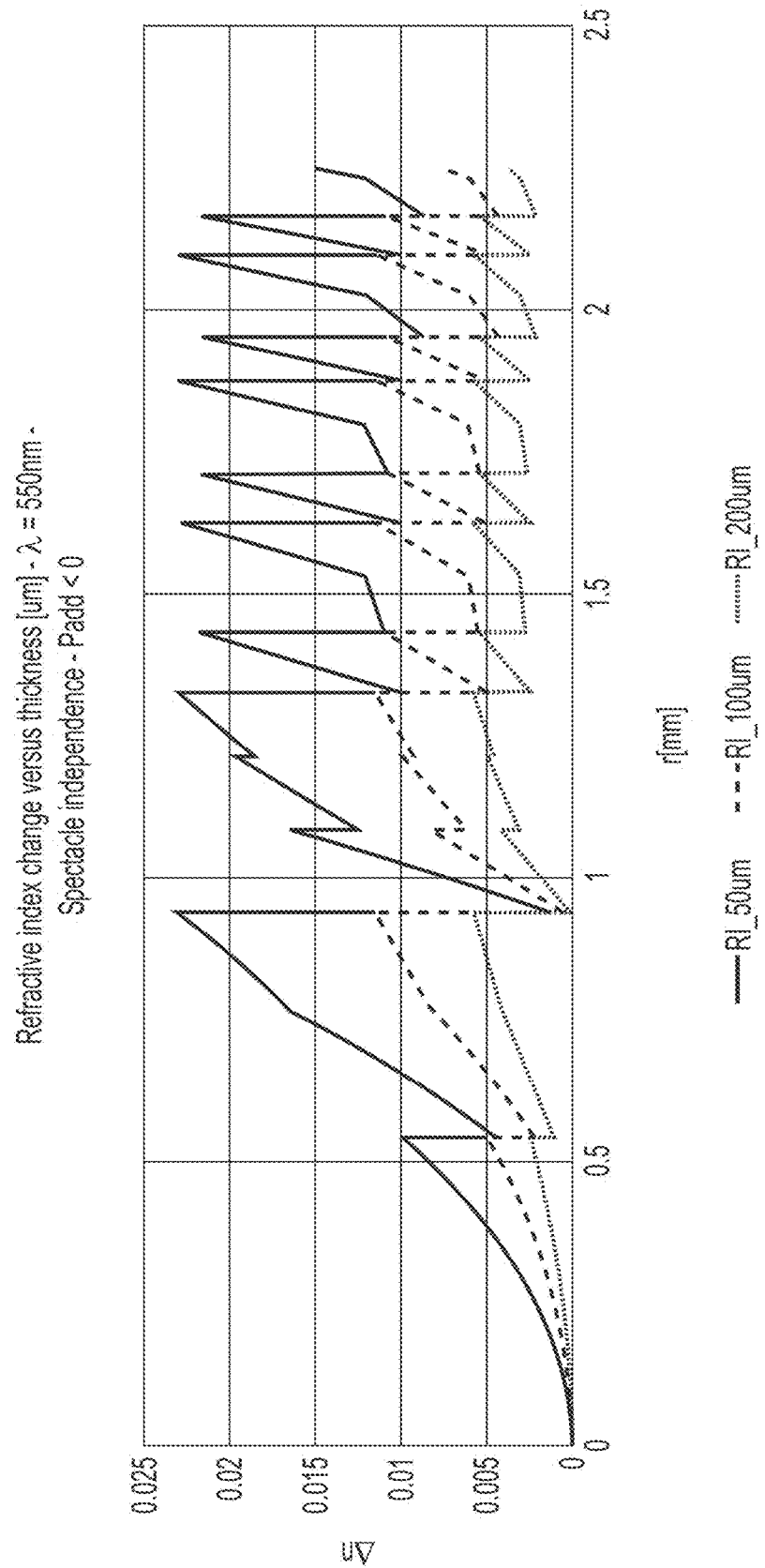
FIGS. 13 and 14 illustrate the radial dependence of the refractive index change for different thicknesses of the optical profile written inside the IOL for spectacle independence, for negative added power (FIG. 13) and positive added power (FIG. 14), in accordance with embodiments of the present disclosure.
Figure 14:
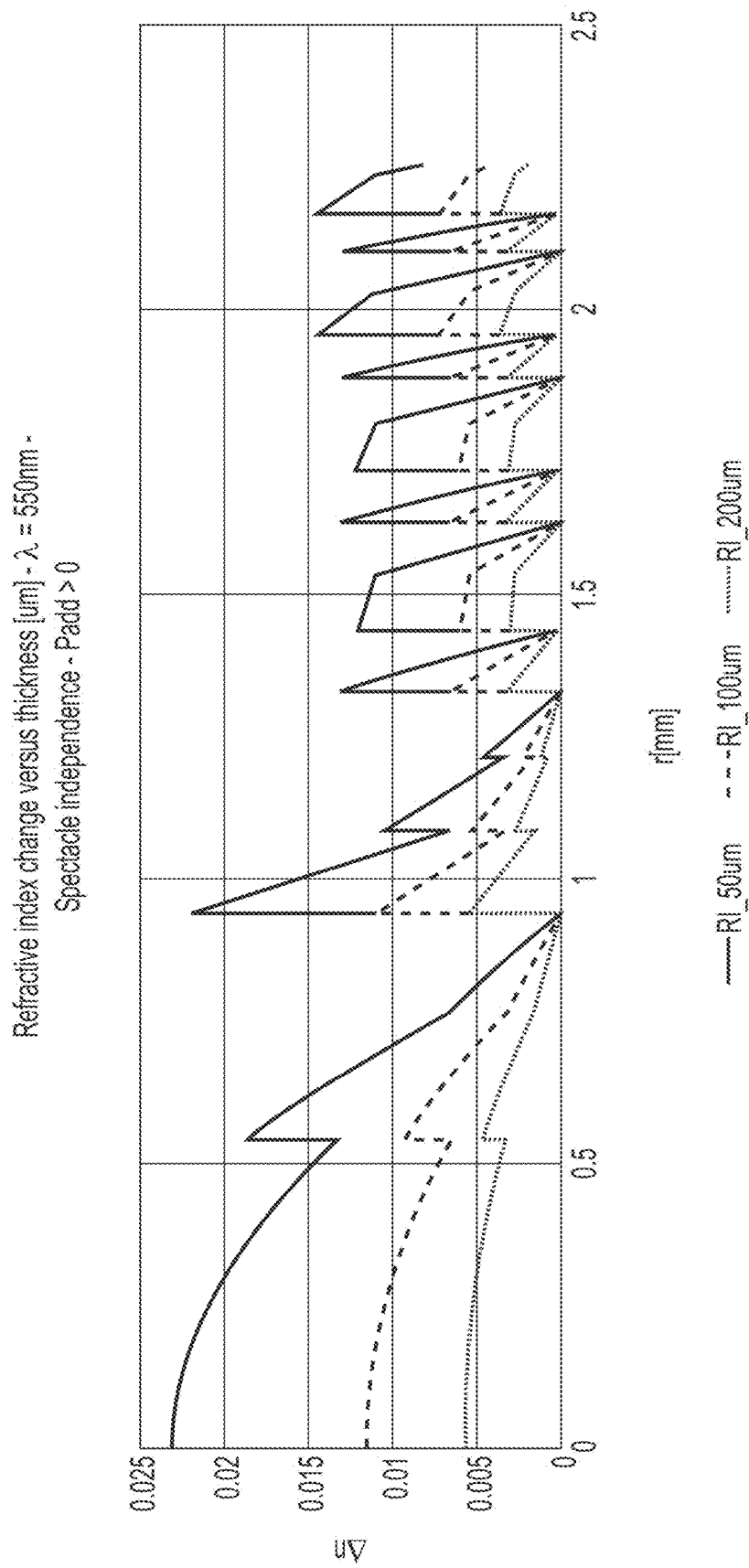

FIGS. 11 and 12 illustrate the radial dependence of the refractive index change for different thicknesses of the optical profile written inside the IOL, for power subtraction (FIG. 11) and power addition (FIG. 12), in accordance with embodiments of the present disclosure. FIGS. 13 and 14 illustrate the radial dependence of the refractive index change for different thicknesses of the optical profile written inside the IOL for spectacle independence, for negative added power (FIG. 13) and positive added power (FIG. 14), in accordance with embodiments of the present disclosure.

Figure 15:
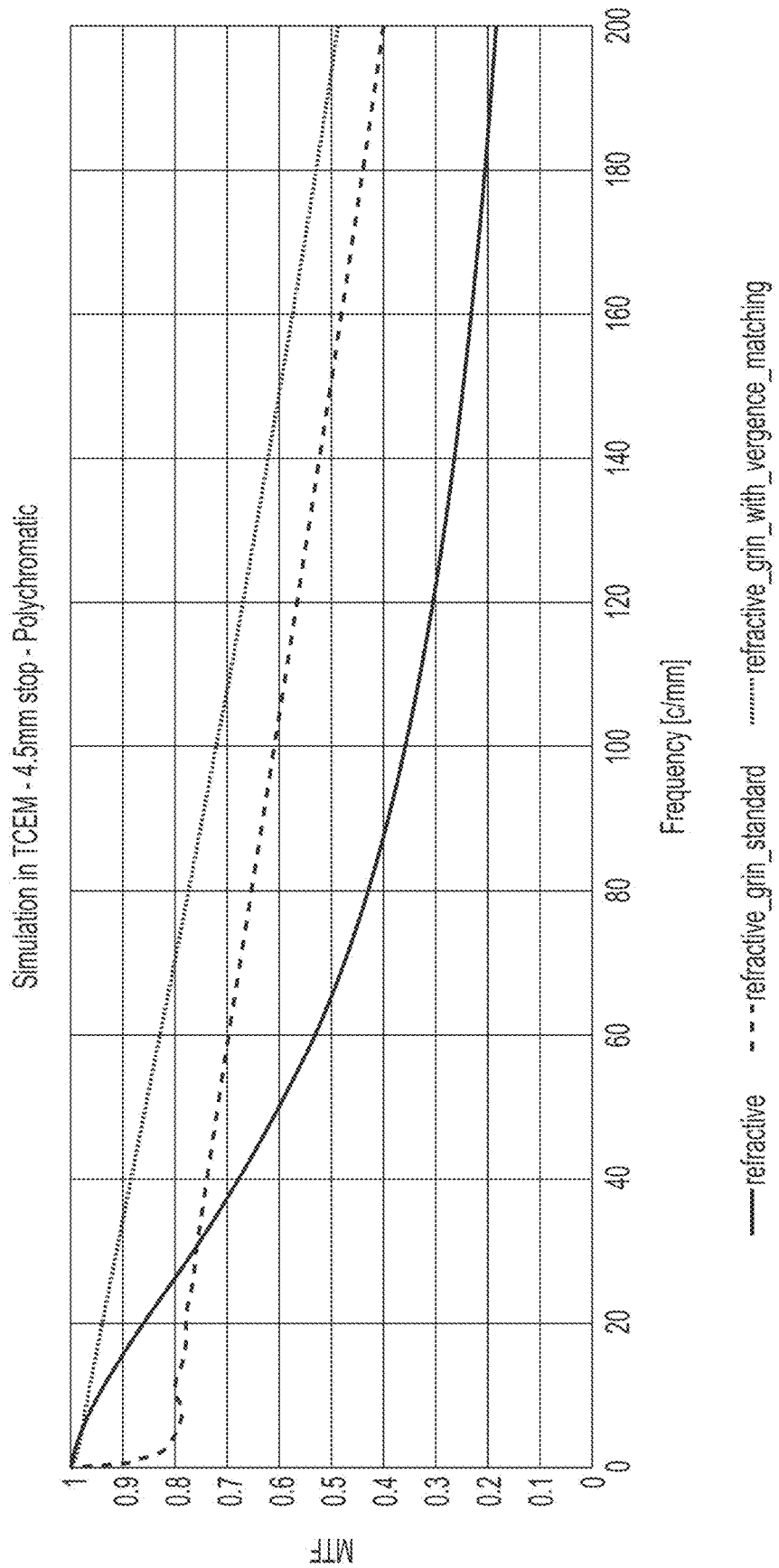
FIG. 15 shows results of simulations in TCEM illustrating through frequency MTF with a comparison between an IOL with a refractive anterior and posterior surface ("refractive"), an IOL with refractive index writing without vergence matching ("grin_standard"), and an IOL with vergence matching according to some embodiments of the present disclosure ("refractive_grin_with_vergence_matching").
Figure 16:
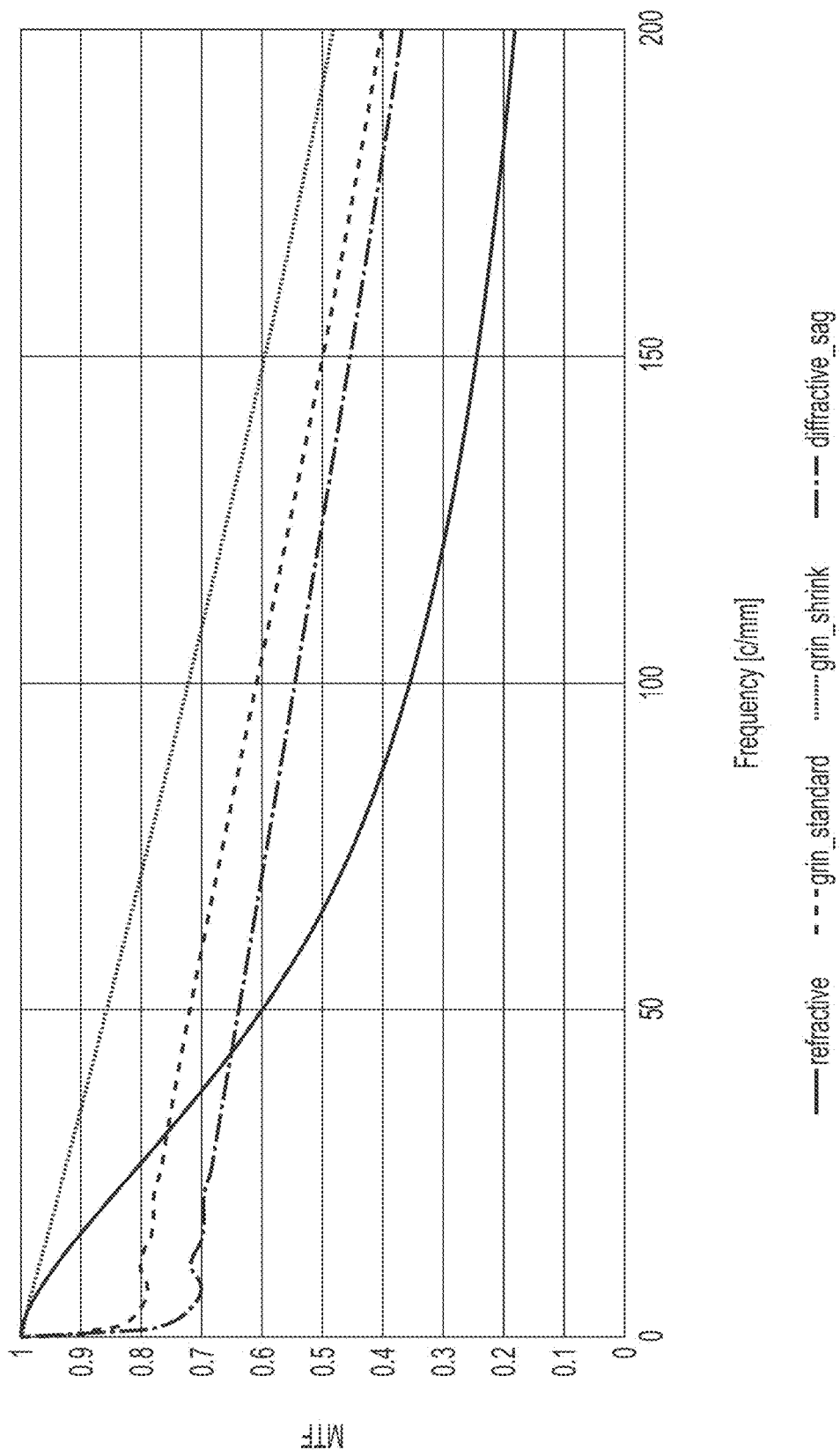
FIGS. 16 and 17 show the results of simulations in TCEM illustrating through frequency MTF (FIG. 16) and through focus MTF at 50 c/mm (FIG. 17), with a comparison between an IOL with a refractive anterior and posterior surface ("refractive"), an IOL with refractive index writing without vergence matching ("grin_standard"), an IOL like the grin_standard, but with the refractive index shrunk along the z axis in accordance with vergence matching in some embodiments described above ("grin_shrink"), and an IOL with refractive anterior and diffractive, elevated, posterior surface according to conventional diffractive IOLs ("diffractive sag").
Figure 17:
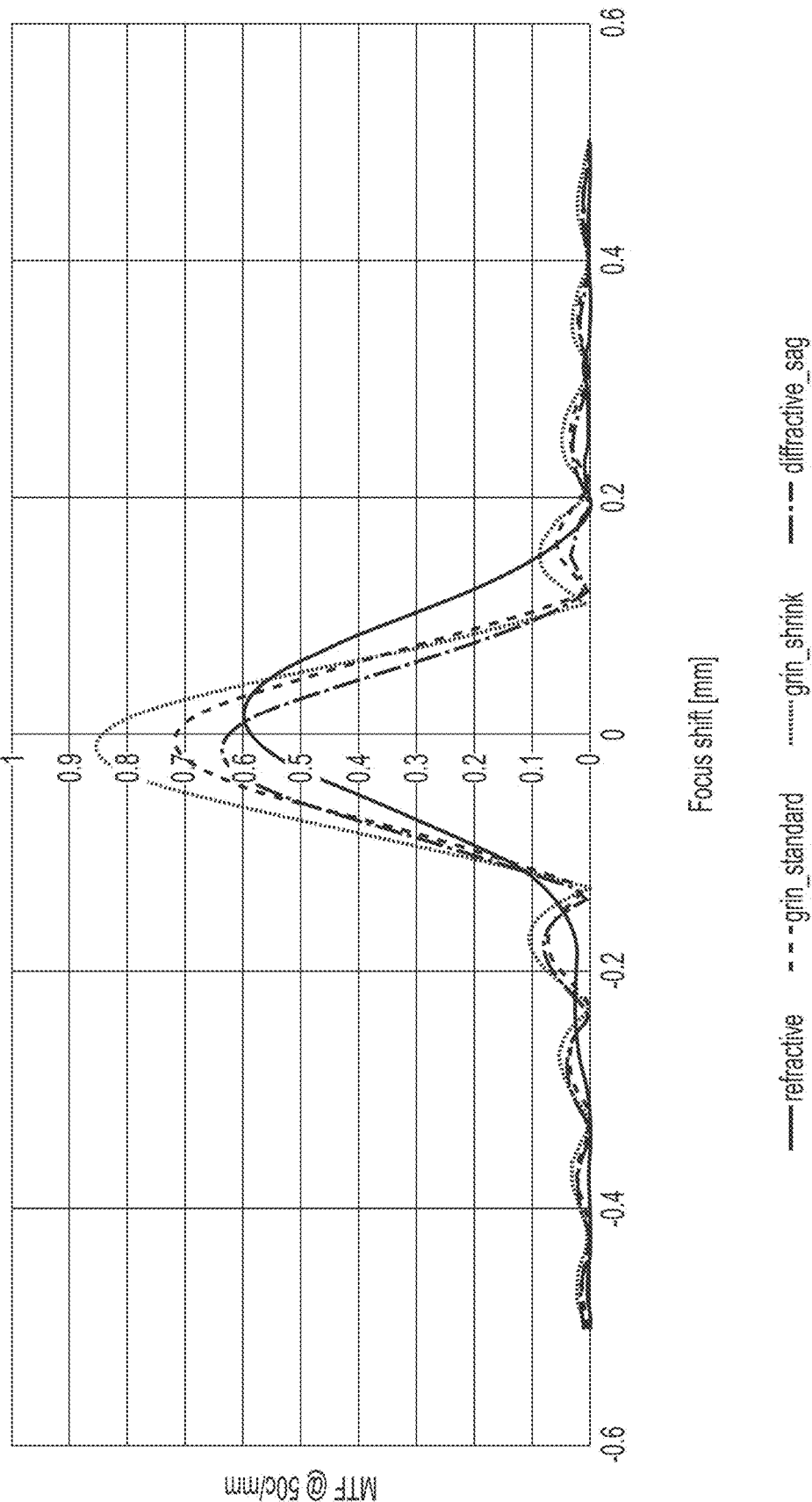

FIG. 15 shows results of simulations in an anatomically correct eye model using ray tracing software (Zemax) illustrating through frequency MTF with a comparison between an IOL with a refractive anterior and posterior surface ("refractive"), an IOL with an anterior refractive surface with refractive index writing without vergence matching ("grin standard"), and an IOL with vergence matching according to some embodiments of the present disclosure ("refractive_grin_with_vergence_matching")."Polychromatic" and "4.5 mm stop" refers to a simulation condition of MTF for white light (polychromatic) and a 4.5 mm pupil diameter. FIG. 16 shows the results of simulations in TCEM illustrating through frequency MTF (FIG. 16) and through focus MTF at 50 c/mm (FIG. 17), with a comparison between an IOL with a refractive anterior and posterior surface ("refractive"), an IOL with refractive index writing without vergence matching ("grin standard"), an IOL like the grin standard, but with the refractive index shrunk along the z axis in accordance with vergence matching in some embodiments described above ("grin shrink"), and an IOL with refractive anterior and diffractive, elevated, posterior surface ("diffractive sag").

Figure 18:
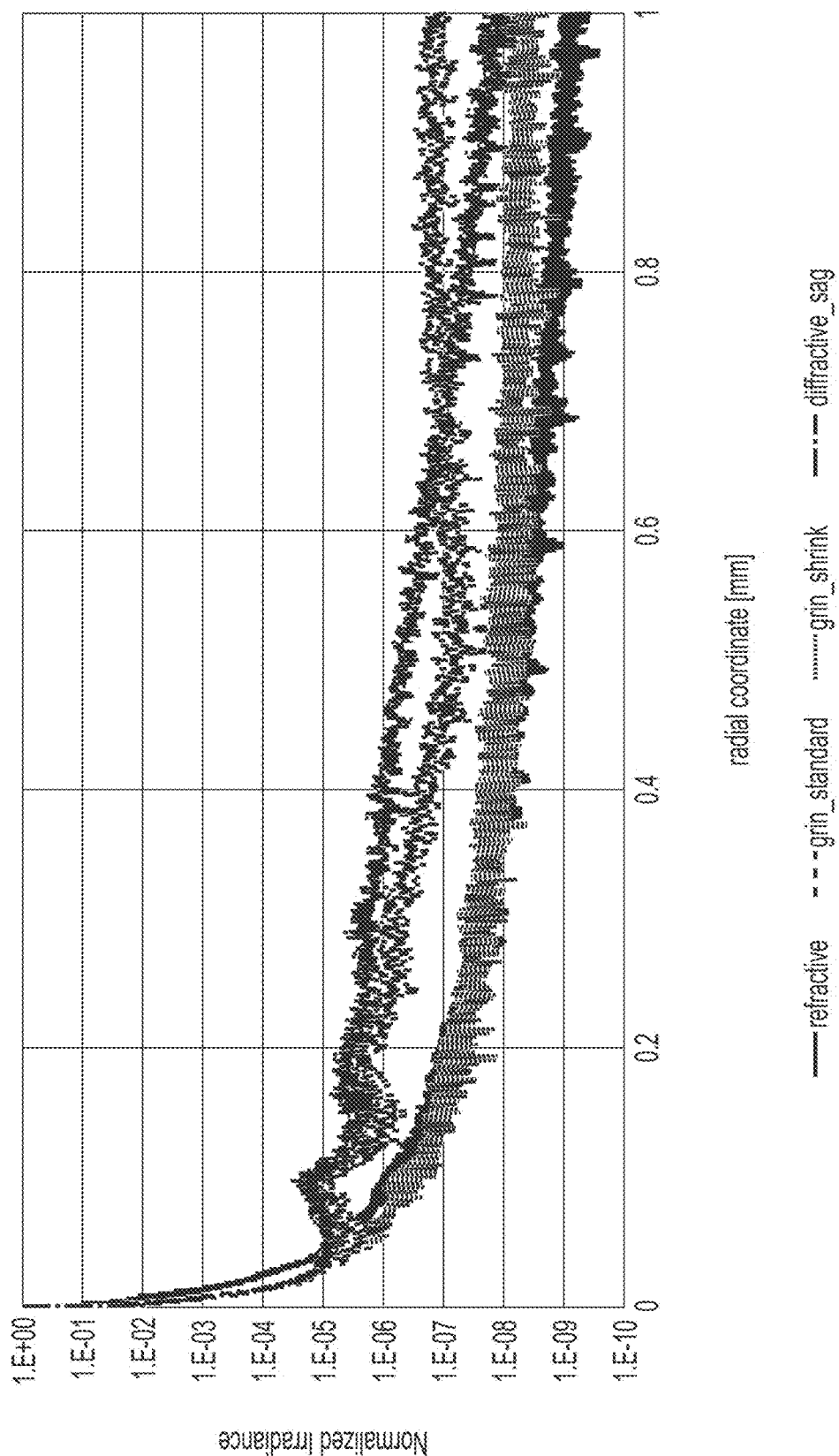
FIGS. 18 and 19 show results illustrating a similar comparison for normalized polychromatic PSF (FIG. 18) and polychromatic halo simulation (FIG. 19).
Figure 19:
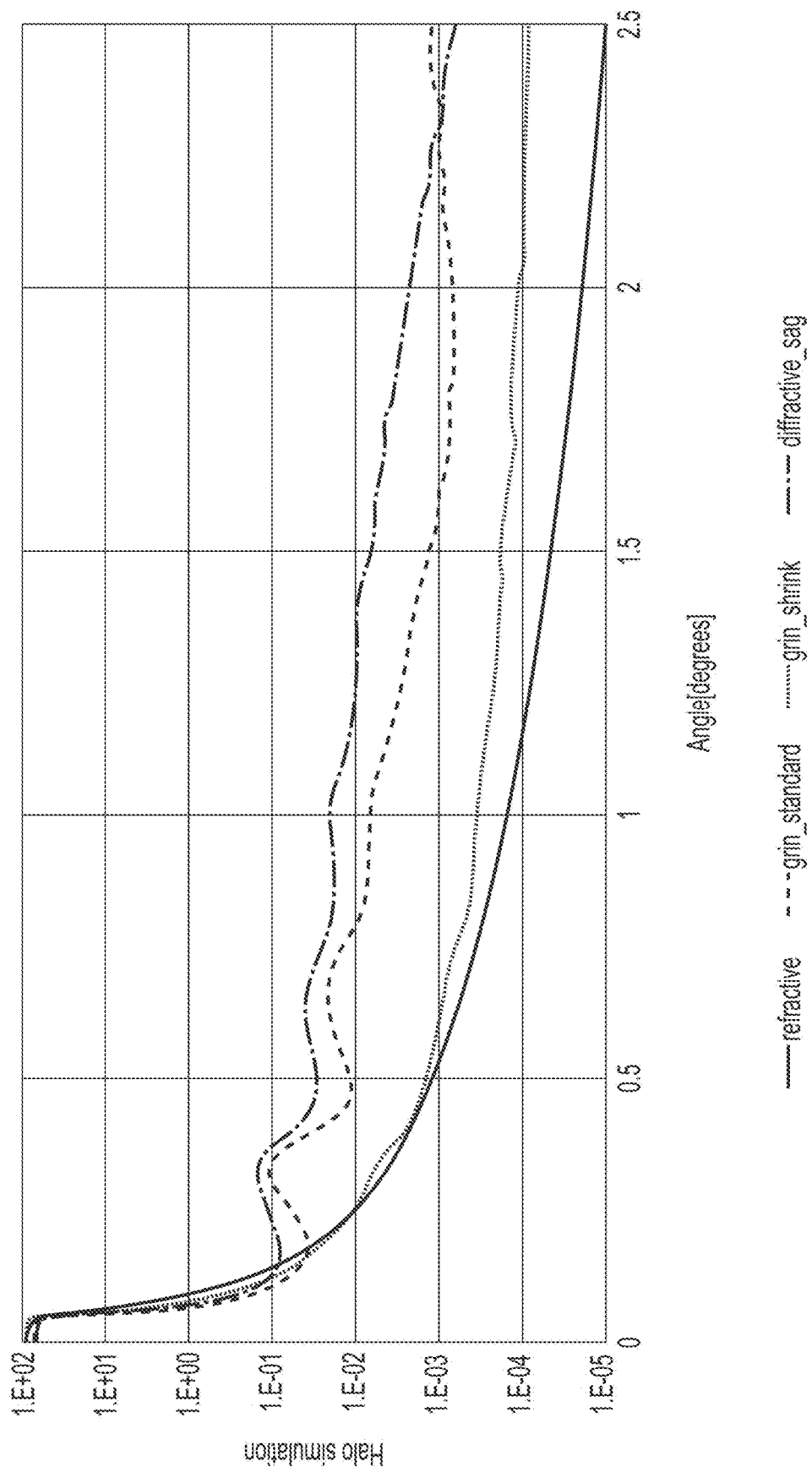
Figure 20:
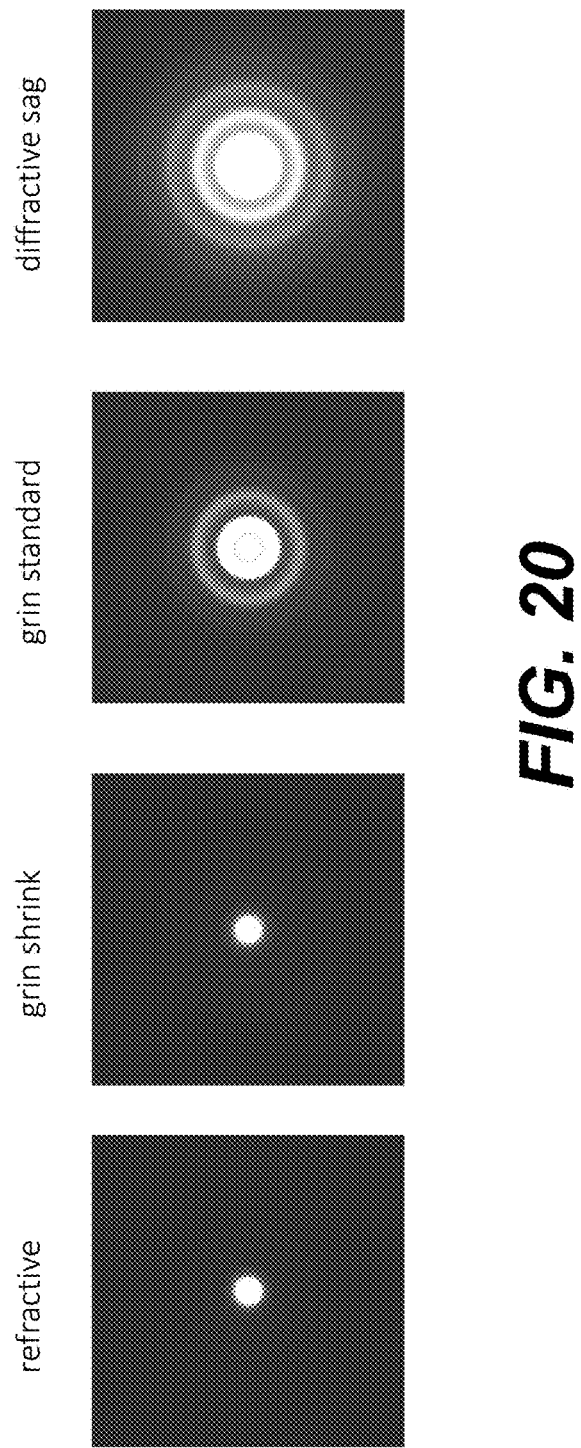
FIG. 20 shows simulated halo performance for a number of different designs: that of a standard refractive IOL ("refractive"), that of an extended depth of focus embodiment with vergence matching ("grin shrink"), that of an extended depth of focus embodiment IOL implemented with normal refractive index writing ("grin standard"), and the same extended depth of focus embodiment achieved by standard methods of elevated posterior surface ("diffractive sag").

FIGS. 18 and 19 show results illustrating a similar comparison for normalized polychromatic point spread function (PSF) (FIG. 18) and polychromatic halo simulation (FIG. 19). Rather than describing the optical quality, as measured by MTF, these Figures show simulated aspects of the perception of visual symptoms (e.g., halo). As a PSF, an ideal would be to have all energy go to a single point, that of 0; it is desired to have a high up peak to the left of the curve, and then immediately the intensity going down; so for the rest of the curve, higher and higher up means a worse and worse perceived halo; "refractive" is lower than others. As further shown, "grin shrink" is particularly good in this aspect. FIG. 20 shows simulated halo performance for a number of different designs: that of a standard refractive IOL ("refractive"), that of an extended depth of focus embodiment with vergence matching ("grin shrink"), that of an extended depth of focus embodiment IOL implemented with normal refractive index writing (grin standard), and the same extended depth of focus embodiment achieved by standard methods of elevated posterior surface (diffractive sag).

Multi-Layer IOL

According to certain aspects, the present disclosure relates to post-surgically improving vision in a subject with an implanted intraocular lens (IOL) through the use of refractive index writing and a flexible, multi-layered gradient index approach, such as to produce an effect like that produced by a GRIN lens. In some embodiments, the multi-layered approach is not diffractive; rather, it is purely refractive, without transition steps; the multi-layered approach can create a long series of transitions rather than a single surface. A power shift can occur not only at anterior and posterior sides of an IOL, but multiple times inside the lens, and without relying on diffractive aspects. In various embodiments, the multiple layers are induced inside the lens at different depths by focusing applied laser radiation at particular selected depths, through changing, e.g., settings and exposure times. The laser can be used to directly reach the desired state, going directly from a starting index of refraction to the desired index of refraction for a particular layer. Accordingly, there is not a restriction on a particular sequence in terms of depths or other progression that must be followed; for instance, one can start with an innermost layer, outermost, or any in between.

In accordance with some embodiments, in order to induce a layer in the IOL, a voxel-based treatment of the IOL is applied, wherein as one goes sequentially through each voxel, the desired shift in refractive index is applied, determined by total amount of light energy focused in the particular area and the duration of focus time. Whereas in some other approaches, for each (x,y) coordinate on the IOL, a uniform shift in refractive index is created over the full range of z where it is applied (i.e., the depth, for example 100 microns, 200 microns, or 400 microns); instead, in accordance with aspects of the multi-layered approach according to embodiments of the present disclosure, there are uniform layers, but changes over z. The depth at which a uniform index of refraction change can be produced can be, for example 20 microns, 30 microns, or 50 microns.

As discussed above in some detail, factors that can limit a subject's visual performance post surgery, for example after cataract surgery, can include: incorrect IOL power, uncorrected astigmatism, IOL placement error, higher order aberrations, spectacle dependence, negative dysphotopsia, peripheral aberrations, and chromatic aberrations.

Figure 21:
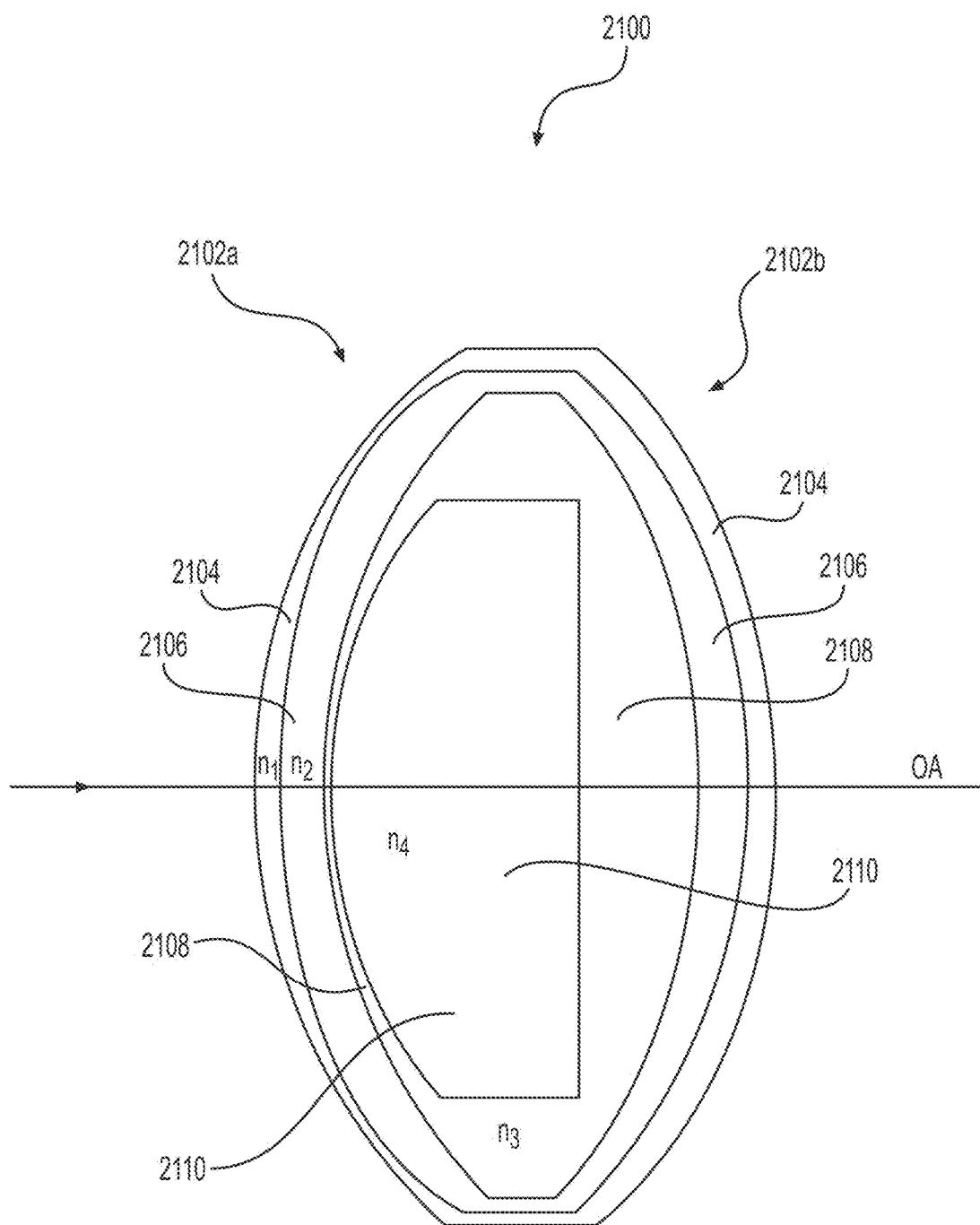
FIG. 21 illustrates an IOL with multiple layers produced by refractive index writing according to some embodiments of the present disclosure.

FIG. 21 illustrates a side, cross-sectional view of an IOL along an optical axis OA, showing the outline of an IOL 2100 (with an anterior side 2102a and posterior side 2102b), the index of refraction of the original IOL $n_1$ several layers 2104, 2016, 2108, 2110 with various shapes, and their associated index of refraction ($n_1$, $n_2$, $n_3$, and $n_4$). In particular, the illustration of FIG. 21 shows the cross-section of the IOL 2100 with the solution being rotationally symmetric. The constructed layers can also be rotationally asymmetric, allowing the correction of astigmatism, higher order aberrations, and other asymmetric errors. The illustration shows four different refractive index values ($n_1$, $n_2$, $n_3$, and $n_4$). In some embodiments, the change in refractive index writing can be 0.2, such that up to 40 different such layers are achievable. For purposes of clarity in the illustrated embodiment of FIG. 21, four layers 2104, 2016, 2108, 2110 are shown.

In some embodiments, the anterior and posterior sides can be of different shape, as is seen for the fourth layer 2110, wherein the anterior is curved and the posterior is flat. The thickness can be close to zero over parts of or all of the layers, as is the case in the anterior side of the interface for the third index change (see left side of layer 2108 proximate the intersection with the optical axis OA). Further, the potential asymmetry is illustrated by the interface of the second layer 2106, which is more curved on the left than on the right side. The described curves are convex. Alternatively, in some embodiments the curves can be concave as well, which induces a negative power change when the inner layers have a higher refractive index. Taken together, this multi-layered approach in refractive index writing allows control and alleviation of a number of the factors limiting post-surgical vision described above, and as will be specifically discussed below in further detail.

Regarding incorrect IOL power, the multi-layer approach according to some embodiments, described above, allows power changes to be made without compromising aberration correction. Furthermore, if the induced layers follow a toric pattern, astigmatic errors of the patient can be corrected; these include: corneal astigmatism (anterior and posterior cornea); surgically induced astigmatism; and/or astigmatism from decentration, tilt, and angle kappa. Negative effects of incorrect IOL placement may also be corrected through the multi-layer approach according to some embodiments. In one embodiment, the implementation the IOL position and tilt is measured, and the desired multi-layer solution compensating for these errors is implemented with refractive index writing. In particular, the patient can receive compensation for the tilt of the IOL by induction of a left-right asymmetry in the multi-layers that have a prismatic effect. This prismatic effect also can be applied to the case when the patient suffers from strabismus; using an internal prism, this approach does not suffer from the limitations that make external prisms unworkable for strabismus patients. With respect to higher order aberrations, even if lenses could be customized with an exact measurement of the higher order aberrations of the patient, such corrections would not be used; even small amounts of decentration, within the range of normal uncertainty of IOL placement (e.g., 0.1 mm) would induce a mismatch between the correction and the original aberration, losing the benefits of the correction and potentially worsening it instead. In a post-operative multi-layered approach according to certain embodiments, the position is controlled with a high accuracy, overcoming this obstacle.

Regarding spectacle independence, refractive multi-focal intraocular lenses are often not popular, as uptake is limited by the zonal nature of such designs. For example, if a lens has a high add power in the center, but a patient has a very small pupil, the entire pupil of the patient would have the add power, inducing a loss in distance vision. Diffractive lenses, on the other hand, are pupil-independent but suffer from visual phenomena. In a multi-layered refractive index writing approach to multifocal design in accordance with some embodiments, a measurement of pupil dynamics under different conditions would precede the algorithmic construction of the different layers. This allows for customization of where add power is created, ensuring near and distance vision for the patient under all lighting conditions.

Some aspects of the present disclosure for construction of a peripheral attenuation zone that removes negative dysphotopsia have been described above. In some embodiments, such an attenuation zone, an outer peripheral area (e.g. the outer 0.5 mm) that gradually diminishes the deviation of the chief ray to zero, can be constructed using refractive index writing for the patients reporting negative dysphotopsia. A multi-layer gradient index approach according to some embodiments also allows the reduction of peripheral aberrations such as oblique astigmatism and coma. This may be a synergistic benefit, combined with the other approaches described above.

Regarding chromatic aberrations, the normal human eye has approximately one diopter of longitudinal chromatic aberrations. While this can be reduced by diffractive designs, doing so can lower image quality. An alternative approach, in accordance with some embodiments, is to utilize refractive designs, using a number of different refracting elements and Abbe numbers. The different powers and Abbe numbers are realized in the multiple layers created by refractive index writing. A desired feature of the implemented total state is that C/V0+F1/V1+F2/V2+F3/V3+ . . . =0, where C is the corneal power, V0 is the Abbe number of the cornea, (F1, F2, F3 . . . ) the power of the different layers and (V1, V2, V3 . . . ) the Abbe numbers.

Consistent with aspects described above, and in accordance with some embodiments of the present disclosure, a method for improving vision in a subject having an implanted intraocular lens (IOL) can include determining at least one modification to be made to an IOL implanted in a subject to improve the vision of the subject, wherein the IOL has a first index of refraction. The method can also include, based on the determination, applying laser radiation to at least one selected area of the IOL to form, within the IOL, at least one additional layer having a different index of refraction than the first index of refraction and a particular shape within the IOL configured to improve the vision of the subject.

In some embodiments, the applied laser radiation changes the index of refraction of the at least one selected area from the first refractive index to the different index of refraction in forming the at least one additional layer. The index of refraction of the at least one additional layer can be uniform throughout the respective layer. The at least one additional layer can be formed with a series of transitions within the IOL and/or formed to have a shape defined by portions having different depths within the IOL. The at least one additional layer can be formed to have a particular thickness and, when formed, at least one of the layers has a different thickness than another one of the layers.

In some embodiments, applied laser radiation can include one or more selected optical energies focused in the at least one selected area and one or more selected durations of exposure of the focused optical energy in the at least one selected area, determined at least in part based on the determined at least one modification to be made to the IOL. In some embodiments, the at least one additional layer can include more than two additional layers, and each of the more than two additional layers can have a respective index of refraction and be formed with a particular shape within the IOL. The more than two additional layers can include at least two different shapes.

In some embodiments, the at least one modification to be made to the IOL can correspond to correcting at least one of incorrect IOL power, uncorrected astigmatism, IOL placement error, higher order aberration, spectacle dependence, negative dysphotopsia, peripheral aberrations, and chromatic aberrations. Applying the laser radiation can include index writing with a plurality of focused laser pulses applied to the at least one selected area of the IOL according to a predetermined pattern. The predetermined pattern can be based at least in part on the determined at least one modification to be made to the IOL.

In another aspect, in some embodiments a method for forming a multi-layered intraocular lens (IOL) can include determining at least one modification to be made to an IOL to improve the visual performance of the IOL, where the IOL has a first index of refraction and, based on the determination, applying laser radiation to the IOL to form, within the IOL, at least one additional layer having a different index of refraction than the first index of refraction and a particular shape within the IOL configured to improve the visual performance of the IOL.

The applied laser radiation can change the index of refraction of the at least one selected area from the first refractive index to the different index of refraction in forming the at least one additional layer. The index of refraction of the at least one additional layer can be uniform throughout the respective layer. The at least one additional layer can be formed to have a shape defined by portions having different depths within the IOL, wherein at least one of the layers has a different thickness than another one of the layers.

In some embodiments, the applied laser radiation can include one or more selected optical energies focused in the at least one selected area of the IOL and one or more selected durations of exposure of the focused optical energy in the at least one selected area, determined at least in part based on the determined at least one modification to be made to the IOL. Applying the laser radiation can include refractive index writing with a plurality of laser pulses applied to the at lease one selected area of the IOL according to a predetermined pattern. The predetermined pattern can be based at least in part on the determined at least one modification to be made to the IOL.

In yet another aspect, in some embodiments a system for improving vision of a subject can include at least one sensor configured to determine a correction to be made to an intraocular lens (IOL) to improve the vision of a subject, wherein the IOL has a first index of diffraction. The system can also include a control system operatively coupled to the at least one sensor and configured to receive associated sensed data corresponding to the correction to be made to the IOL and to calculate, based on the sensed data, shape and/or index of refraction for at least one additional layer to be formed within the IOL. The additional layer can have a different index of refraction than the first index of refraction and a particular shape within the IOL configured to improve the vision of the subject. Additionally or alternatively, the the control system can calculate parameters for a pattern of laser radiation to be applied to at least one selected area of the IOL to form the at least one additional layer; and a radiation system operatively coupled to the control system and configured to, based on control by the control system, apply focused laser radiation according to the parameters and pattern of laser radiation to be applied to at least one selected area of the IOL, to form, within the IOL, the at least one additional layer having the different index of refraction and the particular shape.

The calculated parameters for the pattern of laser radiation can include one or more selected optical energies to be focused in the at least one selected area and one or more selected durations of exposure for the focused optical energy in the at least one selected area. The radiation system can be a pulsed laser system configured to apply the laser radiation by refractive index writing with a plurality of focused laser pulses applied to IOL according to the calculated parameters and pattern.

In some embodiments, the at least one sensor corresponds to an optical coherence tomography (OCT) system configured to determine biometric data associated with the correction to be made to the IOL. The applied laser radiation can change the index of refraction of the at least one area of the IOL from the first refractive index to the different index of refraction in forming the at least one additional layer. The index of refraction of the formed at least one additional layer can be uniform throughout the respective layer. The at least one additional layer can be formed with a series of transitions within the IOL. The at least one additional layer can be formed to have a shape defined by portions having different depths within the IOL. The at least one additional layer can be formed to have a particular thickness, and wherein, when formed, at least one of the layers can have a different thickness than another one of the layers.

The various embodiments described above are provided by way of illustration only and should not be construed to limit the scope of the present disclosure. Those skilled in the art will readily recognize that various modifications and changes may be made to the present disclosure without following the example embodiments and implementations illustrated and described herein, and without departing from the spirit and scope of the disclosure and claims here appended and those which may be filed in non-provisional patent application(s). Therefore, other modifications or embodiments as may be suggested by the teachings herein are particularly reserved.

What is claimed is:

1. A system for improving vision of a subject, the system comprising:
 a pulsed laser system configured to modify a refractive index of at least one selected area of an intraocular lens (IOL) through refractive index writing, wherein the IOL is implanted in an eye of a subject, the pulsed laser system comprising a light source for generating and emitting a plurality of laser pulses, wherein the refractive index writing comprises applying the plurality of laser pulses emitted by the light source to the at least one selected area of the IOL, wherein the at least one selected area of the IOL defines an optical profile induced by the refractive index writing, the optical profile being an internal portion of the IOL that affects a transmission of light through the IOL;
 a control system coupled to the pulsed laser system, the control system comprising a processor and memory, the memory having instructions stored thereon that, when executed by the processor, cause the control system to:
 determine a direction of a plurality of rays associated with a vergence of a wavefront between a cornea of the eye of the subject and the IOL, wherein the plurality of rays are associated with incident light entering the eye of the subject;
 determine a ray direction and a ray height of the plurality of rays at a first location of the optical profile corresponding to where the plurality of rays enter the optical profile of the IOL;
 determine the refractive index of the optical profile at the first location; and
 calculate a pattern in which to apply the plurality of laser pulses to the IOL by, in part, using vergence matching to specify a volume and a shape of each of a plurality of voxels in a corresponding voxel-based vergence-matched three-dimensional phase map such that the volume and shape of each of the plurality of voxels is configured to match the wavefront as the wavefront moves along a direction of propagation of the plurality of rays at the first location of the optical profile of the IOL, in that the shape and volume of each of the plurality of voxels decreases for converging wavefronts and increases for diverging wavefronts, wherein the specifying of the volume and the shape of each of the plurality of voxels is determined from the ray direction, the ray height, and the refractive index at the first location; and
 operate the pulsed laser system to apply the plurality of laser pulses according to the calculated pattern.

2. The system of claim 1, wherein anterior and posterior surfaces of the optical profile are curved such that the plurality of rays have zero incidence with respect to an interface between a surface of at least one other portion of the IOL and a respective surface of the optical profile.

3. The system of claim 2, wherein the curve of the optical profile defines a non-zero curvature about an optical axis of the IOL.

4. The system of claim 1, wherein the instructions further cause the control system to determine, for each ray of the plurality of rays, a second location of the optical profile where the ray exits the optical profile changed by refractive index writing.

5. The system of claim 4, wherein the first location corresponds to a first plane parallel to a vertical axis of the IOL and the second location corresponds to a second plane parallel to the first plane.

6. The system of claim 4, wherein the first location is proximate to or corresponds to an anterior surface of the IOL and wherein the second location is proximate to or corresponds to a posterior surface of the IOL.

7. The system of claim 1, wherein the vergence matching further comprises creating a transformation function calculated by:
 imaging an object at infinity through the cornea of the eye of the subject;
 propagating the imaging of the object through the cornea to an anterior surface of the IOL based on a measured distance between the cornea of the eye of the subject and the anterior surface of the IOL, a shape of the anterior surface of the IOL, and a refractive index of the IOL;
 imaging the object through the anterior surface of the IOL; and
 propagating the imaging of the object through the anterior surface to the optical profile of the IOL.

* * * * *